United States Patent
Frenzel et al.

(10) Patent No.: US 10,104,892 B2
(45) Date of Patent: Oct. 23, 2018

(54) HERBICIDALLY AND FUNGICIDALLY ACTIVE 3-HETEROARYL-ISOXAZOLINE-5-CARBOXAMIDES AND 3-HETEROARYL-ISOXAZOLINE-5-THIOAMIDES

(71) Applicant: BAYER CROPSCIENCE AG, Monheim (DE)

(72) Inventors: Thomas Frenzel, Cologne (DE); Klaus Bernhard Haaf, Kelkheim (DE); Stephen David Lindell, Kelkheim (DE); Lothar Willms, Hofheim (DE); Hansjoerg Dietrich, Liederbach am Taunus (DE); Dirk Schmutzler, Hattersheim (DE); Elmar Gatzweiler, Bad Nauheim (DE); Christopher Hugh Rosinger, Hofheim (DE)

(73) Assignee: BAYER CROPSCIENCE AG, Monheim (DE)

( * ) Notice: Subject to any disclaimer, the term of this patent is extended or adjusted under 35 U.S.C. 154(b) by 391 days.

(21) Appl. No.: 14/429,914

(22) PCT Filed: Sep. 20, 2013

(86) PCT No.: PCT/EP2013/069613
§ 371 (c)(1),
(2) Date: Mar. 20, 2015

(87) PCT Pub. No.: WO2014/048853
PCT Pub. Date: Apr. 3, 2014

(65) Prior Publication Data
US 2015/0223461 A1    Aug. 13, 2015

(30) Foreign Application Priority Data

Sep. 25, 2012  (EP) ..................... 12185775

(51) Int. Cl.
*A01N 43/80*  (2006.01)
*C07D 413/04*  (2006.01)
*C07D 413/14*  (2006.01)
*C07F 9/6558*  (2006.01)
*C07D 417/04*  (2006.01)
*C07D 417/14*  (2006.01)

(52) U.S. Cl.
CPC ........... *A01N 43/80* (2013.01); *C07D 413/04* (2013.01); *C07D 413/14* (2013.01); *C07D 417/04* (2013.01); *C07D 417/14* (2013.01); *C07F 9/65583* (2013.01); *C07F 9/65586* (2013.01)

(58) Field of Classification Search
None
See application file for complete search history.

(56) References Cited

U.S. PATENT DOCUMENTS

| 5,332,175 | A | 7/1994 | Furomoto | |
|---|---|---|---|---|
| 9,078,442 | B2 | 7/2015 | Willms et al. | |
| 2012/0021903 | A1 | 1/2012 | Ahrens et al. | |
| 2014/0100108 | A1* | 4/2014 | Willms ................ | A01N 43/80 504/105 |
| 2015/0245615 | A1 | 9/2015 | Kuhn et al. | |
| 2015/0245616 | A1 | 9/2015 | Haaf et al. | |

FOREIGN PATENT DOCUMENTS

| DE | 4017665 A1 | 12/1991 |
|---|---|---|
| DE | 4026018 A1 | 2/1992 |
| EP | 0520371 A2 | 12/1992 |
| EP | 10170238 | 7/2010 |
| EP | 12185768.4 | 9/2012 |
| EP | 12185767 | 9/2013 |
| GB | 1162257 A | 8/1969 |
| JP | 2005314407 A | 11/2005 |
| WO | 2005021516 A1 | 3/2005 |
| WO | 2012130798 A1 | 10/2012 |

OTHER PUBLICATIONS

Patani, G. A. "Bioisosterism: A rational approach in drug design" Chemical Reviews, 1996, 96(8), 3147-3176.*
International Search Report from corresponding PCT/EP2013/069613, dated Oct. 23, 2013.
Gucma, et al., "Synthesis of 3-Substituted Isoxazolecarboxamides as Potential Fungicides", Letters in Organic Chemistry, 2010, 7, pp. 502-507.
Gucma, "Synthesis and fungicidal activity of substituted isoxazolecarboxamides", Pestycydy/Pesticides, Institute of Industrial Organic Chemistry, Warsaw, Poland, 2010, (1-4), pp. 21-31,XP008159982.
Knapp, "Expedient Synthesis of a 72-Membered Isoxazolino-β-ketoamide Library by a 2•3-Component Reaction", ACS Combinatorial Science, Department of Chemistry, Davis, California, ACS Publications, 2011 American Chemical Society, pp. 85-88.

(Continued)

*Primary Examiner* — Mina Haghighatian
*Assistant Examiner* — Erin Hirt
(74) *Attorney, Agent, or Firm* — McBee Moore Woodward & Vanik IP, LLC

(57) ABSTRACT

Herbicidally and fungicidally active 3-heteroarylisoxazoline-5-carboxamides and 3-heteroarylisoxazoline-5-thioamides of the formula (I) are described.

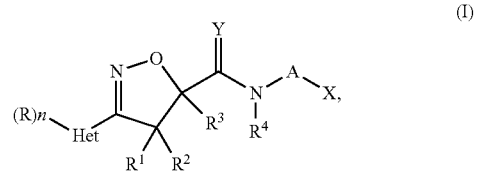

In this formula (I), R represents radicals such as hydrogen, halogen and organic radicals such as substituted alkyl. A is a bond or a divalent unit. Y is a chalcogen.

19 Claims, No Drawings

(56) References Cited

OTHER PUBLICATIONS

Gucma, et al.,"Synthesis and Biological activity of 3-substituted isoxazolecarboxamides", Monatash Chem (2010) 141:451-469, Springer, pp. 461-469.
Y. Iwakura et al., "1,3-Dipoloar cycloaddition reaction of thiophenecarbonitrile N-oxides with various dipolarophiles," Bulletin of the Chemical Society of Japan, vol. 41 (1968), pp. 2954-2959.

* cited by examiner

HERBICIDALLY AND FUNGICIDALLY ACTIVE 3-HETEROARYL-ISOXAZOLINE-5-CARBOXAMIDES AND 3-HETEROARYL-ISOXAZOLINE-5-THIOAMIDES

CROSS REFERENCE TO RELATED APPLICATIONS

This application is a § 371 National Stage Application of PCT/EP2013/069613, filed 20 Sep. 2013 which claims priority to EP 12185775.9 filed 25 Sep. 2012.

BACKGROUND

Field of the Invention

The invention relates to the technical field of herbicides and fungicides, especially that of herbicides for selective control of broad-leaved weeds and weed grasses in crops of useful plants.

Description of Related Art

Specifically, it relates to substituted 3-heteroarylisoxazoline-5-carboxamides and 3-heteroarylisoxazoline-5-thioamides, to processes for preparation thereof and to the use thereof as herbicides and fungicides.

DE 4026018 A1 and EP 520371 A2 and DE 4017665 disclose 3-phenylisoxazoline-5-carboxamides bearing a hydrogen atom in the 5 position of the isoxazoline ring. These compounds are described therein as agrochemically active safeners, i.e. as compounds which eliminate the unwanted herbicidal action of herbicides on crop plants. No herbicidal action of these compounds is disclosed. European patent application No. 10170238, which has an earlier priority date but was yet to be published at the priority date of the present application, discloses herbicidally and fungicidally active 3-phenylisoxazoline-5-carboxamides and 3-phenylisoxazoline-5-thioamides bearing a hydrogen atom in the 5 position of the isoxazoline ring. Monatshefte Chemie (2010) 141, 461, Pesticides (2010) 21-31 and Letters in Organic Chemistry (2010), 7, 502 also disclose 3-phenylisoxazoline-5-carboxamides bearing a hydrogen atom in the 5 position of the isoxazoline ring. Fungicidal action is disclosed for some of the compounds mentioned.

WO 2005/021516 discloses the compounds
3-({[3-(4-tert-butylpyridin-2-yl)-5-ethyl-4,5-dihydro-1,2-oxazol-5-yl]carbonyl}amino)-5-fluoro-4-oxopentanoic acid
3-({[3-(4-tert-butylpyridin-2-yl)-5-isopropyl-4,5-dihydro-1,2-oxazol-5-yl]carbonyl}amino)-5-fluoro-4-oxopentanoic acid,
3-({[3-(4-iso-butylpyridin-2-yl)-5-ethyl-4,5-dihydro-1,2-oxazol-5-yl]carbonyl}amino)-5-fluoro-4-oxopentanoic acid,
3-({[3-(4-acetylpyridin-2-yl)-5-ethyl-4,5-dihydro-1,2-oxazol-5-yl]carbonyl}amino)-5-fluoro-4-oxopentanoic acid,
3-({[5-ethyl-3-(pyridin-2-yl)-4,5-dihydro-1,2-oxazol-5-yl]carbonyl}amino)-5-fluoro-4-oxopentanoic acid and
3-({[5-ethyl-3-(4-isobutylpyridin-2-yl)-4,5-dihydro-1,2-oxazol-5-yl]carbonyl}amino)-5-fluoro-4-oxopentanoic acid,
each having pharmacological action.

SUMMARY

It is an object of the present invention to provide herbicidally and fungicidally active compounds.

It has been found that 3-heteroarylisoxazoline-5-carboxamides and 3-heteroarylisoxazoline-5-thioamides are of particularly good suitability as herbicides and fungicides. The present invention provides 3-heteroarylisoxazoline-5-carboxamides and 3-heteroarylisoxazoline-5-thioamides of the formula (I) and the N-oxides thereof in which

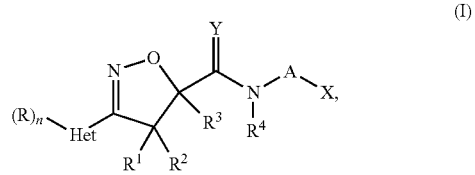

$R^1$ and $R^2$ are each independently hydrogen, fluorine, chlorine, bromine, iodine, cyano, or $(C_1$-$C_4)$-alkyl or $(C_1$-$C_4)$-alkoxy each substituted by m radicals from the group consisting of fluorine, chlorine, bromine, iodine and cyano, or $R^1$ and $R^2$ together with the carbon atom to which they are bonded form a saturated or partly or fully unsaturated three-, four- or five-membered ring formed from q carbon atoms and p oxygen atoms;

$R^3$ is fluorine, chlorine, cyano, $(C_1$-$C_3)$-alkylcarbonyloxy or $S(O)_nR^5$, or $(C_1$-$C_6)$-alkyl, $(C_3$-$C_6)$-cycloalkyl, $(C_2$-$C_6)$-alkenyl or $(C_2$-$C_6)$-alkynyl each substituted by m radicals from the group consisting of fluorine, chlorine, bromine, iodine, cyano, $(C_1$-$C_4)$-alkoxy and hydroxyl, or $(C_2$-$C_6)$-alkenylcarbonyl substituted by m radicals from the group consisting of fluorine, chlorine, bromine, iodine, cyano and $(C_1$-$C_6)$-alkoxy;

or $(C_1$-$C_6)$-alkoxy, $(C_3$-$C_6)$-cycloalkoxy, $(C_4$-$C_6)$-alkenyloxy or $(C_2$-$C_6)$-alkynyloxy each substituted by m radicals from the group consisting of fluorine, chlorine, bromine, iodine, cyano, $(C_1$-$C_4)$-alkoxy and hydroxyl;

$R^4$ is hydrogen, cyano, or $(C_1$-$C_8)$-alkyl, $(C_3$-$C_8)$-alkenyl, $(C_3$-$C_8)$-alkynyl or $(C_3$-$C_8)$-cycloalkyl each substituted by m radicals from the group consisting of fluorine, chlorine, bromine, iodine, cyano, hydroxyl and $(C_1$-$C_6)$-alkoxy;

A is a bond or a divalent unit from the group consisting of

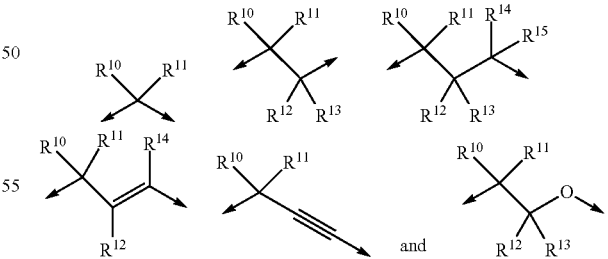

$R^{10}$, $R^{11}$, $R^{12}$, $R^{13}$, $R^{14}$ and $R^{15}$ are each independently hydrogen, fluorine, chlorine, bromine, iodine, hydroxyl, cyano, $CO_2R^8$, $CONR^6R^8$, $R^5$, or $(C_1$-$C_6)$-alkyl, $(C_3$-$C_5)$-cycloalkyl, $(C_2$-$C_6)$-alkenyl or $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

Y is oxygen or sulfur;

X is hydrogen, cyano, hydroxyl, $X^1$, or $(C_1$-$C_{12})$-alkyl, $(C_3$-$C_8)$-cycloalkyl, $(C_2$-$C_{12})$-alkenyl or $(C_2$-$C_{12})$-alkynyl each substituted by m radicals from the group consisting of fluorine, chlorine, bromine, iodine, cyano, hydroxyl, $OR^7$, $X^1$, $OX^1$, $NHX^1$, $S(O)_nR^5$, $SO_2NR^6R^7$, $SO_2NR^6COR^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6)$=$NOR^8$, or X, A and $R^4$ together with the nitrogen atom to which they are bonded form a saturated or partly or fully unsaturated five-, six- or seven-membered ring containing, as well as this nitrogen atom, k carbon atoms, n oxygen atoms, p sulfur atoms and p elements from the group consisting of $NR^7$ and $NCOR^7$ as ring atoms, where one carbon atom bears p oxo groups;

$X^1$ is a three-, four-, five- or six-membered saturated, partly unsaturated, fully unsaturated or aromatic ring which is formed from r carbon atoms, s nitrogen atoms, n sulfur atoms and n oxygen atoms, and which is substituted by s radicals from the group consisting of $R^6$, $R^{6a}$, $R^8$ and $R^9$, where the sulfur atoms and carbon atoms that form this ring each bear n oxo groups;

Het is a three-, four-, five- or six-membered saturated, partly unsaturated, fully unsaturated or aromatic ring which is formed from r carbon atoms, s nitrogen atoms, n sulfur atoms and t oxygen atoms, where the indices n, s and t should not all be zero at the same time, and where the sulfur atoms and carbon atoms that form this ring each bear n oxo groups;

R is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $S(O)_nR^5$, $SO_2NR^6R^8$, $OSO_2NR^6R^8$, or $(C_1$-$C_6)$-alkyl, $(C_2$-$C_6)$-alkenyl, $(C_2$-$C_6)$-alkynyl each substituted by m radicals from the group consisting of fluorine, chlorine, bromine, iodine, hydroxyl and cyano;

or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

$R^5$ is $(C_1$-$C_6)$-alkyl or $(C_3$-$C_6)$-cycloalkyl each substituted by m radicals from the group consisting of fluorine, chlorine, bromine, iodine, cyano and hydroxyl;

$R^6$ is hydrogen or $R^5$;

$R^{6a}$ is fluorine, chlorine, bromine, iodine, cyano, hydroxyl, $S(O)_nR^5$, or $(C_1$-$C_6)$-alkoxy, $(C_3$-$C_6)$-alkenyloxy or $(C_3$-$C_6)$-alkynyloxy each substituted by m radicals from the group consisting of fluorine, chlorine, bromine, cyano and $(C_1$-$C_2)$-alkoxy;

$R^7$ is hydrogen or $(C_1$-$C_6)$-alkyl, $(C_3$-$C_6)$-cycloalkyl, $(C_2$-$C_4)$-alkenyl or $(C_2$-$C_4)$-alkynyl each substituted by m radicals from the group consisting of fluorine, chlorine, bromine, cyano and $(C_1$-$C_2)$-alkoxy;

$R^8$ is $R^7$;

$R^9$ is $(C_1$-$C_3)$-alkyl or $(C_1$-$C_3)$-alkoxy;

k is 3, 4, 5 or 6;

m is 0, 1, 2, 3, 4 or 5;

n is 0, 1 or 2;

p is 0 or 1;

q is 3, 4 or 5;

r is 1, 2, 3, 4 or 5;

s is 0, 1, 2, 3 or 4;

t is 0, 1 or 2, excluding the compounds in which A-X is the 5-fluoro-4-oxopentan-3-yl acid radical.

DETAILED DESCRIPTION OF A PREFERRED EMBODIMENT

Alkyl means saturated straight-chain or branched hydrocarbyl radicals having the number of carbon atoms specified in each case, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogen-substituted alkyl means straight-chain or branched alkyl groups where some or all of the hydrogen atoms in these groups may be replaced by halogen atoms, e.g. $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl.

Alkenyl means unsaturated straight-chain or branched hydrocarbyl radicals having the number of carbon atoms specified in each case and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl means straight-chain or branched hydrocarbyl radicals having the number of carbon atoms specified in each case and one triple bond in any position, e.g. $C_2$-$C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Alkoxy means saturated straight-chain or branched alkoxy radicals having the number of carbon atoms specified in each case, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Halogen-substituted alkoxy means straight-chain or branched alkoxy radicals having the number of carbon atoms specified in each case, where some or all of the hydrogen atoms in these groups may be replaced by halogen atoms as specified above, e.g. $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro, 2-difluoroethoxy, 2,2-dichloro-2-fluoroethoxy, 2,2,2-trichloroethoxy, pentafluoroethoxy and 1,1,1-trifluoroprop-2-oxy.

According to the nature of the substituents and the way in which they are joined, the compounds of the formula (I) may be present as stereoisomers. If, for example, one or more asymmetrically substituted carbon atoms and/or sulfoxides are present, enantiomers and diastereomers may occur. Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all stereoisomers and mixtures thereof which are encompassed by the formula (I) but not defined specifically. For the sake of simplicity, however, reference is always made hereinafter to compounds of the formula (I), even though this means both the pure compounds and, if appropriate, mixtures having different proportions of isomeric compounds.

According to the nature of the substituents defined above, the compounds of the formula (I) have acidic properties and can form salts, and if appropriate also internal salts or adducts with inorganic or organic bases or with metal ions.

If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

If a group is polysubstituted by radicals, this means that this group is substituted by one or more identical or different radicals from those mentioned.

In all the formulae specified hereinafter, the substituents and symbols have the same meaning as described in formula (I), unless defined differently. Arrows in a chemical formula denote the points at which it is joined to the rest of the molecule.

Preference is given to 3-heteroarylisoxazoline-5-carboxamides and 3-heteroarylisoxazoline-5-thioamides of the formula (I) in which $R^1$ and $R^2$ are each independently hydrogen, fluorine, chlorine, bromine, iodine, cyano, or $(C_1$-$C_4)$-alkyl or $(C_1$-$C_4)$-alkoxy each substituted by m radicals from the group consisting of fluorine, chlorine, bromine, iodine and cyano, or $R^1$ and $R^2$ together with the carbon atom to which they are bonded form a saturated or partly or fully unsaturated three-, four- or five-membered ring formed from q carbon atoms and p oxygen atoms;

$R^3$ is $(C_1$-$C_6)$-alkyl, $(C_3$-$C_6)$-cycloalkyl, $(C_2$-$C_6)$-alkenyl or $(C_2$-$C_6)$-alkynyl each substituted by m radicals from the group consisting of fluorine, chlorine, bromine, iodine, cyano, $(C_1$-$C_4)$-alkoxy and hydroxyl, $R^4$ is hydrogen, cyano, or $(C_1$-$C_8)$-alkyl, $(C_3$-$C_8)$-alkenyl, $(C_3$-$C_8)$-alkynyl or $(C_3$-$C_8)$-cycloalkyl each substituted by m radicals from the group consisting of fluorine, chlorine, bromine, iodine, cyano, hydroxyl and $(C_1$-$C_6)$-alkoxy;

A is a bond or a divalent unit from the group consisting of

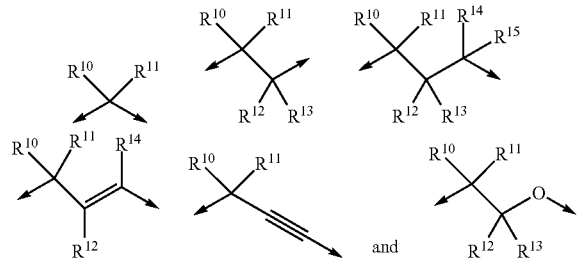

$R^{10}$, $R^{11}$, $R^{12}$, $R^{13}$, $R^{14}$ and $R^{15}$ are each independently hydrogen, fluorine, chlorine, bromine, iodine, hydroxyl, cyano, $CO_2R^8$, $CONR^6R^8$, $R^5$, or $(C_1$-$C_6)$-alkyl, $(C_3$-$C_5)$-cycloalkyl, $(C_2$-$C_6)$-alkenyl or $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

Y is oxygen or sulfur;

X is hydrogen, cyano, hydroxyl, $X^1$, or $(C_1$-$C_{12})$-alkyl, $(C_3$-$C_8)$-cycloalkyl, $(C_2$-$C_{12})$-alkenyl or $(C_2$-$C_{12})$-alkynyl each substituted by m radicals from the group consisting of fluorine, chlorine, bromine, iodine, cyano, hydroxyl, $OR^7$, $X^1$, $OX^1$, $NHX^1$, $S(O)_nR^5$, $SO_2NR^6R^7$, $SO_2NR^6COR^8$, $CO_2R^8$, $CONR^6R^8$, $COR^6$, CONR⁸SO₂R⁵, NR⁶R⁸, NR⁶COR⁸, NR⁸CONR⁸R⁸, NR⁶CO₂R⁸, NR⁶SO₂R⁸, NR⁶SO₂NR⁶R⁸, OCONR⁶R⁸, OCSNR⁶R⁸, POR⁹R⁹ and C(R⁶)=NOR⁸, or X, A and R⁴ together with the nitrogen atom to which they are bonded form a saturated or partly or fully unsaturated five-, six- or seven-membered ring containing, as well as this nitrogen atom, k carbon atoms, n oxygen atoms, p sulfur atoms and p elements from the group consisting of NR⁷ and NCOR⁷ as ring atoms, where one carbon atom bears p oxo groups;

X¹ is a ring which is substituted by s radicals from the group consisting of R⁶, R⁶ᵃ, R⁸ and R⁹ and is from the group consisting of

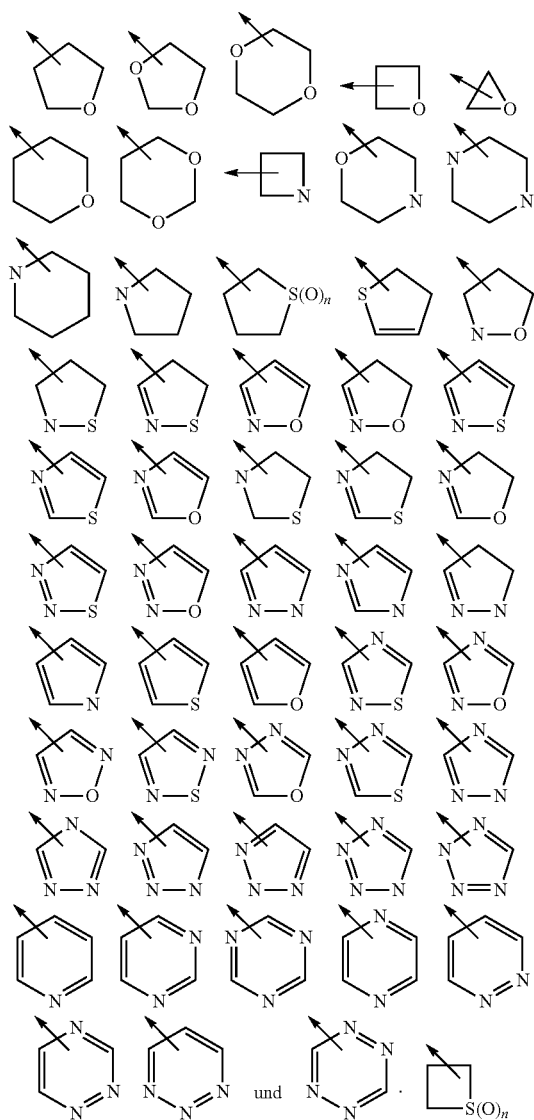

or X¹ is phenyl substituted by m radicals from the group consisting of R⁶, R⁶ᵃ, R⁸ and R⁹;

Het is pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,2,4-triazin-3-yl, 1,2,4-triazin-5-yl, 1,2,4-triazin-6-yl, 1,3,5-triazin-2-yl, 1,2,4,5-tetrazin-3-yl, pyrrol-1-yl, pyrrol-2-yl, pyrrol-3-yl, furan-2-yl, furan-3-yl, thiophen-2-yl, thiophen-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 2H-1,2,4-triazol-3-yl, 4H-1,2,4-triazol-3-yl, 4H-1,2,4-triazol-4-yl, 1,2,3-oxadiazol-4-yl, 1,2,3-oxadiazol-5-yl, 1,2,3-thiadiazol-4-yl, 1,2,3-thiadiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-thiadiazol-3-yl, 1,3,4-oxadiazol-2-yl, 1,3,4-thiadiazol-2-yl, 1H-tetrazol-5-yl, 2H-tetrazol-5-yl, 1,4,5,6-tetrahydropyrimidin-2-yl, 1,4,5,6-tetrahydropyridazin-3-yl, 5,6-dihydro-4H-1,3-oxazin-2-yl, 5,6-dihydro-4H-1,2-oxazin-3-yl, 5,6-dihydro-4H-1,3-thiazin-2-yl, 5,6-dihydro-4H-1,2-thiazin-3-yl, 4,5-dihydro-1H-imidazol-2-yl, 4,5-dihydro-1H-pyrazol-3-yl, 4,5-dihydro-1,3-oxazol-2-yl, 4,5-dihydro-1,2-oxazol-3-yl, 4,5-dihydro-1,3-thiazol-2-yl, 4,5-dihydro-1,2-thiazol-3-yl, azetidin-1-yl, azetidin-2-yl, azetidin-3-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, oxiran-2-yl, oxetan-2-yl, oxetan-3-yl, tetrahydrofuran-2-yl, tetrahydrofuran-3-yl, tetrahydro-2H-pyran-2-yl, tetrahydro-2H-pyran-3-yl, tetrahydro-2H-pyran-4-yl, 1,3-dioxolan-2-yl, 1,3-dioxolan-4-yl, 1,3-dioxan-2-yl, 1,3-dioxan-4-yl, 1,3-dioxan-5-yl, morpholin-2-yl, morpholin-3-yl or morpholin-4-yl;

R is fluorine, chlorine, bromine, iodine, hydroxyl, cyano, nitro, SF₅, CONR⁸SO₂R⁵, CONR⁶R⁸, COR⁶, CO₂R⁸, CONR⁶R⁸, C(R⁶)=NOR⁸, NR⁶COR⁸, NR⁶CONR⁸R⁸, NR⁶CO₂R⁸, NR⁶SO₂R⁸, NR⁶SO₂NR⁶R⁸, OCONR⁶R⁸, OSO₂R⁵, S(O)ₙR⁵, SO₂NR⁶R⁸, OSO₂NR⁶R⁸, or (C₁-C₆)-alkyl, (C₂-C₆)-alkenyl, (C₂-C₆)-alkynyl each substituted by m radicals from the group consisting of fluorine, chlorine, bromine, iodine, hydroxyl and cyano, or (C₁-C₆)-alkoxy, (C₃-C₆)-cycloalkoxy, (C₂-C₆)-alkenyloxy or (C₂-C₆)-alkynyloxy each substituted by m radicals from the group consisting of fluorine, chlorine, bromine, iodine, cyano and (C₁-C₂)-alkoxy;

R⁵ is (C₁-C₆)-alkyl or (C₃-C₆)-cycloalkyl each substituted by m radicals from the group consisting of fluorine, chlorine, bromine, iodine, cyano and hydroxyl;

R⁶ is hydrogen or R⁵;

R⁶ᵃ is fluorine, chlorine, bromine, iodine, cyano, hydroxyl, S(O)ₙR⁵, or (C₁-C₆)-alkoxy, (C₂-C₆)-alkenyloxy or (C₂-C₆)-alkynyloxy each substituted by m radicals from the group consisting of fluorine, chlorine, bromine, cyano and (C₁-C₂)-alkoxy;

R⁷ is hydrogen or (C₁-C₆)-alkyl, (C₃-C₆)-cycloalkyl, (C₂-C₄)-alkenyl or (C₂-C₄)-alkynyl each substituted by m radicals from the group consisting of fluorine, chlorine, bromine, cyano and (C₁-C₂)-alkoxy;

R⁸ is R⁷;

R⁹ is (C₁-C₃)-alkyl or (C₁-C₃)-alkoxy;

k is 3, 4, 5 or 6;
m is 0, 1, 2, 3, 4 or 5;
n is 0, 1 or 2;
p is 0 or 1;
q is 3, 4 or 5;
s is 0, 1, 2, 3 or 4;
t is 0, 1 or 2.

Particular preference is given to 3-heteroarylisoxazoline-5-carboxamides and 3-heteroarylisoxazoline-5-thioamides of the formula (I) in which $R^1$ and $R^2$ are each independently hydrogen, fluorine, chlorine, bromine, iodine, cyano, or $(C_1-C_4)$-alkyl substituted by m radicals from the group consisting of fluorine, chlorine, bromine, iodine and cyano;

$R^3$ is $(C_1-C_4)$-alkyl, $(C_3-C_4)$-cycloalkyl, $(C_2-C_3)$-alkenyl or $(C_2-C_3)$-alkynyl each substituted by m radicals from the group consisting of fluorine, chlorine, bromine, cyano and $(C_1-C_2)$-alkoxy, A is a bond or a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH=CH$, $C(CH_3)_2C\equiv C$, $CH(CF_3)CH_2$, $CH(CH_3)CH_2O$, $CH_2CH_2O$, $CH(cPr)CH_2O$, $CH(CH_2OCH_3)$, $CH(CH_2CH_2SCH_3)$, $CH(COOH)$, $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

$R^4$ is hydrogen or $(C_1-C_8)$-alkyl;

Y is oxygen or sulfur;

X is hydrogen, cyano, hydroxyl, $X^1$, or $(C_1-C_{12})$-alkyl, $(C_3-C_8)$-cycloalkyl, $(C_2-C_{12})$-alkenyl or $(C_2-C_{12})$-alkynyl each substituted by m radicals from the group consisting of fluorine, chlorine, cyano, hydroxyl, $OR^7$, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring which is substituted by s radicals from the group consisting of $R^6$, $R^{6a}$, $R^8$ and $R^9$ and is from the group consisting of

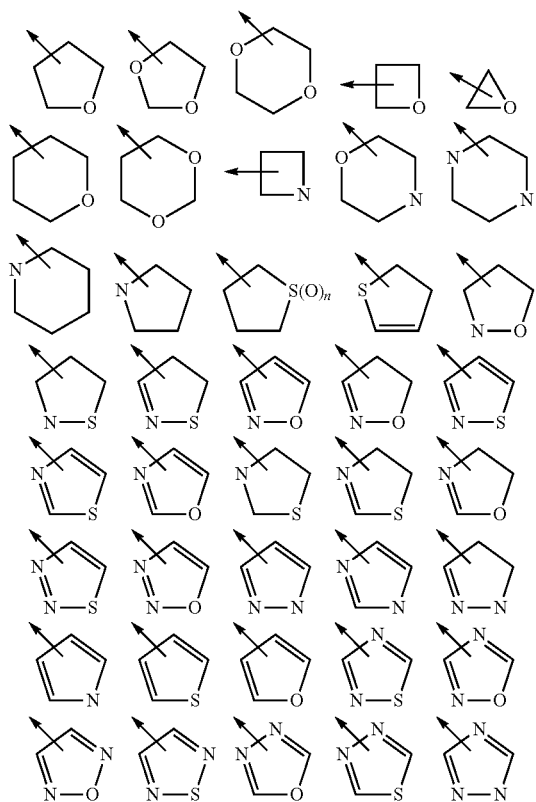

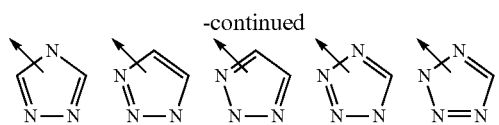

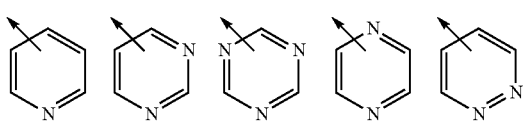

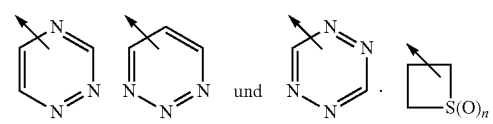

or $X^1$ is phenyl substituted by m radicals from the group consisting of $R^6$, $R^{6a}$, $R^8$ and $R^9$;

Het is pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,2,4-triazin-3-yl, 1,2,4-triazin-5-yl, 1,2,4-triazin-6-yl, 1,3,5-triazin-2-yl, pyrrol-3-yl, furan-2-yl, furan-3-yl, thiophen-2-yl, thiophen-3-yl, pyrazol-3-yl, pyrazol-4-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-4-yl, 2H-1,2,3-triazol-4-yl, 1H-1,2,4-triazol-3-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 2H-tetrazol-5-yl or 4,5-dihydro-1,2-oxazol-3-yl.

R is fluorine, chlorine, bromine, cyano, or $(C_1-C_6)$-alkyl each substituted by m radicals from the group consisting of fluorine and chlorine, or $(C_1-C_6)$-alkoxy substituted by m radicals from the group consisting of fluorine and chlorine;

$R^5$ is methyl or ethyl;

$R^6$ is hydrogen or $R^5$;

$R^{6a}$ is fluorine, chlorine, bromine, iodine, cyano, hydroxyl, $S(O)_nR^5$, or $(C_1-C_6)$-alkoxy, $(C_2-C_6)$-alkenyloxy or $(C_2-C_6)$-alkynyloxy each substituted by m radicals from the group consisting of fluorine, chlorine, bromine, cyano and $(C_1-C_2)$-alkoxy;

$R^7$ is hydrogen or $(C_1-C_6)$-alkyl each substituted by m radicals from the group consisting of fluorine and chlorine;

$R^8$ is $R^7$;

$R^9$ is $(C_1-C_3)$-alkoxy;

m is 0, 1, 2 or 3;

n is 0, 1 or 2;

s is 0, 1, 2, 3 or 4;

t is 0, 1 or 2.

The inventive compounds can be prepared by reactions known per se to those skilled in the art, for example according to the reaction sequence specified in scheme 1.

Scheme 1:

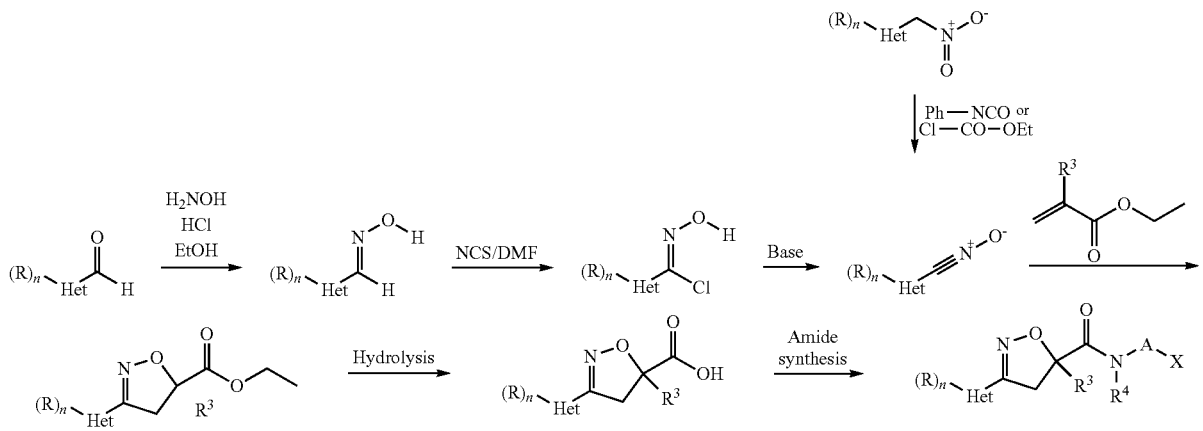

Such 1,3-dipolar cycloadditions of nitrile oxides with suitable dipolarophiles are described, for example, in Reviews: 1,3 dipolar Cycloaddition Chemistry, Padwa, ed. Wiley, New York, 1984; Kanemasa and Tsuge, Heterocycles 1990, 30, 719.

Inventive compounds substituted in the 4 and 5 positions of the isoxazoline ring system can likewise be prepared by 1,3-dipolar cycloaddition by using suitably 1,2-disubstituted olefins as dipolarophiles. In most cases, this reaction affords diastereomer mixtures which can be separated by column chromatography. Optically active isoxazolines can be obtained by chiral HPLC of suitable precursors or end products, and likewise by enantioselective reactions, for example enzymatic ester or amide cleavage or through the use of chiral auxiliaries on the dipolarophile, as described by Olssen (J. Org. Chem. 1988, 53, 2468).

Inventive compounds can also be prepared through the use of commercially available, suitably substituted alkenes as reactant. For instance, suitably substituted acrylic esters or acrylamides can be used.

Scheme 2:

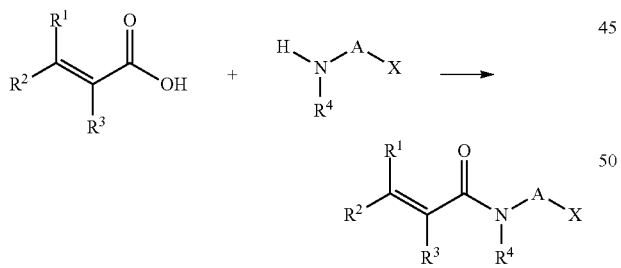

One option for activating the acrylic acid is carbodiimides, for example EDCI (Chen, F. M. F.; Benoiton, N. L. Synthesis 1979, 709). For preparation of acrylamides, see U.S. Pat. No. 2,521,902, JP60112746, J. of Polymer Science 1979, 17 (6), 1655. Suitably substituted acrylamides can be reacted in a 1,3-cycloaddition reaction with nitrile oxides to give the inventive compounds.

Scheme 3:

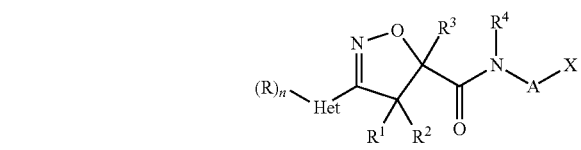

Transformations of the functional groups $R^3$ are possible either at the alkene stage or at the isoxazoline stage. Scheme 4 describes the route to various $R^3$-substituted isoxazolines.

Scheme 4:

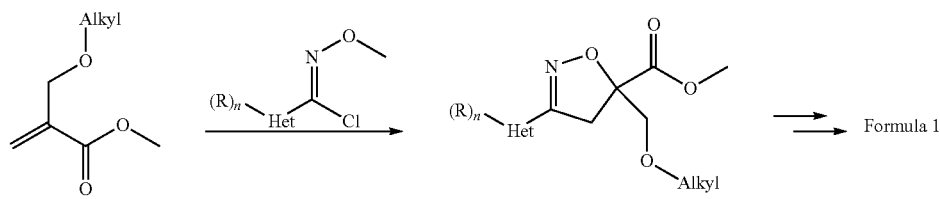

-continued

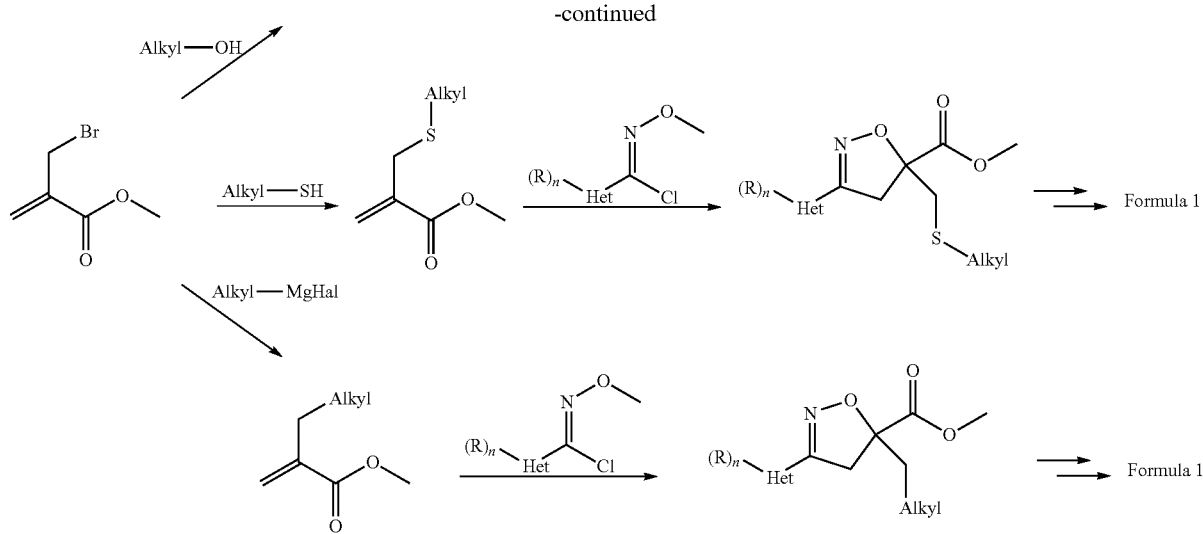

Inventive compounds having a vinyl group as the $R^3$ substituent can be prepared from the inventive compounds having a hydroxymethyl group as $R^3$ substituent as illustrated in Scheme 5.

Scheme 5:

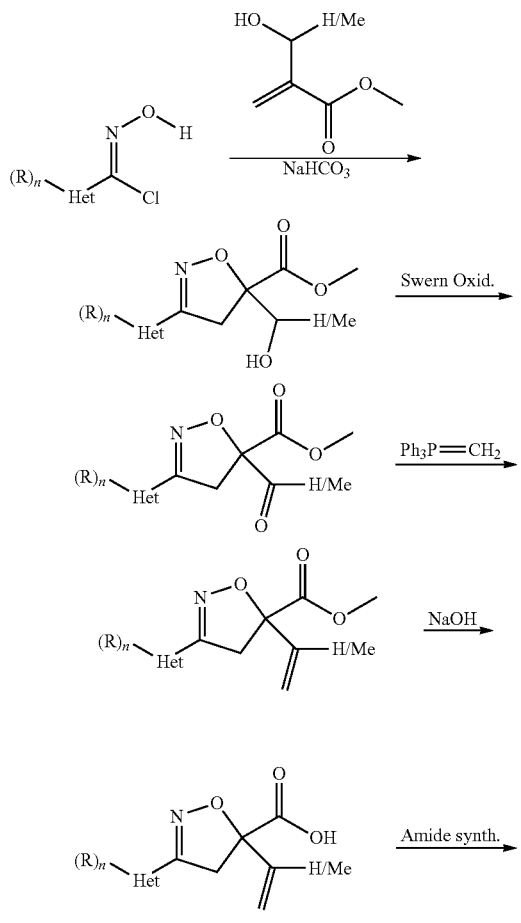

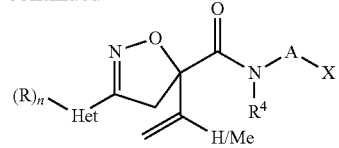

Inventive compounds having a cyano group as $R^3$ substituent can be formed analogously using suitable cyanoacrylates, for example ethyl 2-cyanoacrylate. Suitably substituted crotonic esters can be utilized for preparation of $R^2$- and $R^3$-disubstituted isoxazolines. Some crotonic esters are commercially available, and they can also be prepared from ethyl 3-bromoacrylate, for example, by nucleophilic substitution reactions. Such methods are described, for example, in Birkofer, L.; Hempel, K. Chem. Ber., 1963, 96, 1373; Tanoury, G. J.; Chen, M.; Dong, Y.; Forslund, R. E.; Magdziak, D.; Organic Letters, 2008, 10, 185.

The preparation of suitably substituted 2-alkoxyacrylic esters (if $R^3$ is alkoxy) is possible, for example, by conversion of alpha-keto esters to corresponding ketals (lit.: Wenkert, E; Alonso, M. E.; Buckwalter B. L., Sanchez E. L. J. Am. Chem. Soc. 1983, 105, 2021 and lit.: LaMattina, J. L.; Mularski, C. J., J. Org. Chem. 1984, 49, 4800), and the elimination thereof to give 2-alkoxyacrylic esters (analogously to lit.: Esswein A. et al., Helvetica Chimica Acta 1989, 72(2), 213).

Scheme 6 describes the route to 3-heteroarylisoxazoline-5-thioamides through conversion of the 3-heteroarylisoxazoline-5-carboxamides through the use of the Lawesson reagent (lit.: WYETH, WO2003/93277, lit.: Wishka D. G., Walker D. P., Tetrahedron Letters 2011, 52, 4713-4715).

Scheme 6:

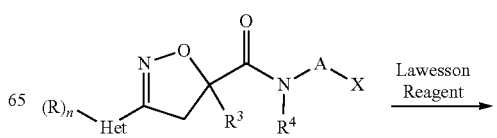

-continued

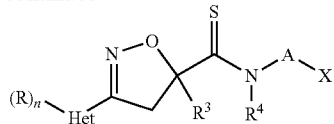

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor Gunther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the formula (I) and salts thereof can be prepared completely or partially by solid-phase supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Gunther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, individual or several synthesis steps may be supported by the use of microwave technology. The specialist literature describes a series of experimental protocols, for example in Microwaves in Organic and Medicinal Chemistry (editor: C. O . Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), referred to collectively as "inventive compounds" hereinafter, have excellent herbicidal efficacy against a broad spectrum of economically important monocotyledonous and dicotyledonous annual harmful plants. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the inventive compounds are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage of the time of application, or they die completely after a certain time, such that competition by the weeds, which is harmful to the crop plants, is thus eliminated very early and in a lasting manner.

Although the inventive compounds have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, will be damaged to a negligible extent only, if at all, depending on the structure of the particular inventive compound and its application rate. For these reasons, the present compounds are very suitable for selective control of unwanted plant growth in plant crops such as agriculturally useful plants or ornamental plants.

In addition, the inventive compounds (depending on their particular structure and the application rate deployed) have outstanding growth-regulating properties in crop plants. They intervene in the plants' own metabolism with regulatory effect, and can thus be used for controlled influencing of plant constituents and to facilitate harvesting, for example by triggering desiccation and stunted growth. In addition, they are also suitable for general control and inhibition of unwanted vegetative growth without killing the plants. Inhibition of vegetative growth plays a major role for many mono- and dicotyledonous plants since, for example, this can reduce or completely prevent lodging.

By virtue of their herbicidal and plant-growth-regulatory properties, the active ingredients can also be used to control harmful plants in crops of known genetically modified plants or genetically modified plants still to be developed. In general, transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate e.g. to the harvested material with regard to quantity, quality, storeability, composition and specific constituents. For instance, there are known transgenic plants with an elevated starch content or altered starch quality, or those with a different fatty acid composition in the harvested material. Further special properties may be tolerance or resistance to abiotic stress factors, for example heat, cold, drought, salinity and ultraviolet radiation.

Preference is given to the use of the inventive compounds of the formula (I) or salts thereof in economically important transgenic crops of useful plants and ornamental plants, for example of cereals such as wheat, barley, rye, oats, millet, rice, cassava and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP 0221044, EP 0131624). For example, there have been descriptions of several cases of genetic modifications of crop plants for the purpose of modifying the starch synthesized in the plants (e.g. WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soya with the trade name or the designation Optimum™ GAT™ (Glyphosate ALS Tolerant).

transgenic crop plants, for example cotton, capable of producing *Bacillus thuringiensis* toxins (Bt toxins), which make the plants resistant to particular pests (EP 0142924 A, EP 0193259 A), transgenic crop plants with a modified fatty acid composition (WO 91/013972 A), genetically modified crop plants having novel constituents or secondary metabolites, for example novel phytoalexins, which cause an increase in disease resistance (EP 0309862 A, EP 0464461 A), genetically modified plants having reduced photorespiration, which have higher yields and higher stress tolerance (EP 0305398 A), transgenic crop plants which produce pharmaceutically or diagnostically important proteins ("molecular pharming")

transgenic crop plants which feature higher yields or better quality, transgenic crop plants which feature a combination, for example, of the abovementioned novel properties ("gene stacking")

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim, 2nd edition, 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants. Thus, transgenic plants can be obtained whose properties are altered by overexpression, suppression or inhibition of homologous (=natural) genes or gene sequences or expression of heterologous (=foreign) genes or gene sequences.

The inventive compounds (I) can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients, or to any desired combinations of these active ingredients.

The inventive compounds can be used with particular preference in transgenic crop plants which are resistant to a combination of glyphosates and glufosinates, glyphosates and sulfonylureas or imidazolinones. Most preferably, the inventive compounds can be used in transgenic crop plants such as corn or soybean with the trade name or the designation Optimum™ GAT™ (glyphosate ALS tolerant), for example.

When the inventive active ingredients are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds of the formula (I) and/or of the compounds of the formula (Ia) as herbicides for control of harmful plants in transgenic crop plants.

The inventive compounds can be applied in the form of wettable powders, emulsifiable concentrates, sprayable solutions, dusting products or granules in the customary formulations. The invention therefore also provides herbicidal and plant-growth-regulating compositions which comprise the inventive compounds.

The inventive compounds are especially suitable as herbicides.

The inventive compounds can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in: Winnacker-Küchler, "Chemische Technologie", Band 7, C. Hanser Verlag München, 4. Aufl. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte" [Interface-active Ethylene Oxide Adducts], Wiss. Verlagsgesell., Stuttgart 1976, Winnacker-Küchler, "Chemische Technologie", Volume 7, C. Hanser Verlag Munich, 4th ed. 1986.

On the basis of these formulations, it is also possible to produce combinations with other active ingredients, for example insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyethoxylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatus such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active ingredient with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylates or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of inventive compounds. In wettable powders, the active ingredient concentration is, for example, about 10 to 90% by weight, the remainder to 100% by weight consisting of customary formulation constituents. In emulsifiable concentrates, the active ingredient concentration may be about 1 to 90% and preferably 5 to 80% by weight. Dust-type formulations contain from 1 to 30% by weight of active ingredient, preferably usually from 5 to 20% by weight of active ingredient; sprayable solutions contain from about 0.05 to 80% by weight, preferably from 2 to 50% by weight of active ingredient. In the case of water-dispersible granules, the active ingredient content depends partially on whether the active ingredient is present in liquid or solid form and on which granulation auxiliaries, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for scattering and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more of active substance, but it is preferably between 0.005 and 750 g/ha.

In addition to the herbicidal properties, the inventive compounds also have good fungicidal properties. The present invention thus also relates to a composition for controlling unwanted microorganisms, comprising the inventive active ingredients. Preference is given to fungicidal compositions comprising agriculturally usable auxiliaries, solvents, carriers, surfactants or extenders.

In addition, the invention also relates to a method for controlling unwanted microorganisms, which comprises applying the inventive active ingredients to the phytopathogenic fungi and/or their habitat.

According to the invention, a carrier is a natural or synthetic organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, corn cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide. In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Suitable liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

The inventive compositions may additionally comprise further components, for example surfactants. Useful surfactants are emulsifiers and/or foam formers, dispersants or wetting agents having ionic or nonionic properties, or mixtures of these surfactants. Examples thereof are salts of polyacrylic acid, salts of lignosulfonic acid, salts of phenolsulfonic acid or naphthalenesulfonic acid, polycondensates of ethylene oxide with fatty alcohols or with fatty acids or with fatty amines, substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolyzates, lignosulfite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition. It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes. In general, the inventive compositions and formulations contain between 0.05 and 99% by weight, 0.01 and 98% by weight, preferably between 0.1 and 95% by weight and more preferably between 0.5 and 90% active ingredient, most preferably between 10 and 70 percent by weight. The inventive active ingredients or compositions can be used as such or, depending on their respective physical and/or chemical properties, in the form of the formulations thereof or the use forms prepared therefrom, such as aerosols, capsule suspensions, cold-fogging concentrates, warm-fogging concentrates, encapsulated granules, fine granules, free-flowing concentrates for the treatment of seed, ready-to-use solutions, dustable powders, emulsifiable concentrates, oil-in-water emulsions, water-in-oil emulsions, macrogranules, microgranules, oil-dispersible powders, oil-miscible free-flowing concentrates, oil-miscible liquids, foams, pastes, pesticide-coated seed, suspension concentrates, suspoemulsion concentrates, soluble concentrates, suspensions, spray powders, soluble powders, dusts and granules, water-soluble granules or tablets, water-soluble powders for seed treatment, wettable powders, active ingredient-impregnated natural products and synthetic substances, and also microencapsulations in polymeric substances and in coating materials for seed, and also ULV cold-fogging and warm-fogging formulations.

The formulations mentioned can be produced in a manner known per se, for example by mixing the active ingredients with at least one customary extender, solvent or diluent, emulsifier, dispersant and/or binder or fixative, wetting agent, water repellent, optionally siccatives and UV stabilizers and optionally dyes and pigments, antifoams, preservatives, secondary thickeners, tackifiers, gibberellins and other processing auxiliaries.

The inventive compositions include not only formulations which are already ready for use and can be deployed with a suitable apparatus onto the plant or the seed, but also commercial concentrates which have to be diluted with water prior to use.

The inventive active ingredients may be present as such or in their (commercial standard) formulations, or else in the use forms prepared from these formulations as a mixture with other (known) active ingredients, such as insecticides, attractants, sterilants, bactericides, acaricides, nematicides, fungicides, growth regulators, herbicides, fertilizers, safeners or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

The invention further comprises a method for treating seed.

The invention further relates to seed which has been treated by one of the methods described in the previous paragraph. The inventive seeds are used in methods for protection of seed from unwanted microorganisms. In these methods, seed treated with at least one inventive active ingredient is used. The inventive active ingredients or compositions are also suitable for the treatment of seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has long been known and is the subject of constant improvements. Nevertheless, the treatment of seed gives rise to a series of problems which cannot always be solved in a satisfactory manner. For instance, it is desirable to develop methods for protecting the seed and the germinating plant which dispense with, or at least significantly reduce, the additional deployment of crop protection compositions after sowing or after emergence of the plants. It is additionally desirable to optimize the amount of active ingredient used so as to provide optimum protection for the seed and the germinating plant from attack by phytopathogenic fungi, but without damage to the plant itself by the active ingredient employed. In particular, methods for treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed for protection of the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions protects not only the seed itself but also the resulting plants after emergence from phytopathogenic fungi. In this way, the immediate treatment of the crop at the time of sowing or shortly thereafter can be dispensed with.

The inventive compositions are suitable for protecting seed of any plant cultivar which is used in agriculture, in greenhouses, in forests or in horticulture and viticulture. In particular, this is the seed of cereals (such as wheat, barley, rye, triticale, sorghum/millet and oats), corn, cotton, soybeans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular importance.

As also described below, the treatment of transgenic seed with the inventive active ingredients or compositions is of particular significance.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

In general, in the treatment of the seed, it has to be ensured that the amount of the inventive composition and/or further additives applied to the seed is selected such that the germination of the seed is not impaired and the plant which arises therefrom is not damaged. This has to be ensured particularly in the case of active ingredients which can exhibit phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417 A, U.S. Pat. No. 4,245,432 A, U.S. Pat. Nos. 4,808,430, 5,876,739, US 2003/0176428 A1, WO 2002/080675 A1, WO 2002/028186 A2.

The active ingredients usable in accordance with the invention can be converted to the customary seed dressing formulations, such as solutions, emulsions, suspensions, powders, foams, slurries or other coating compositions for seed, and also ULV formulations.

These formulations are produced in a known manner, by mixing the active ingredients with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients.

Preference is given to using alkyl naphthalenesulfonates, such as diisopropyl or diisobutyl naphthalenesulfonates.

Suitable dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ethers, and the phosphated or sulfated derivatives thereof. Suitable anionic dispersants are especially lignosulfonates, polyacrylic acid salts and arylsulfonate/formaldehyde condensates.

Antifoams which may be present in the seed dressing formulations usable in accordance with the invention are all foam-inhibiting substances conventionally used for the formulation of active agrochemical compounds. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Useful adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the seed dressing procedure is to place the seed into a mixer, to add the particular desired amount of seed dressing formulations, either as such or after prior dilution with water, and to mix them until the formulation is distributed homogeneously on the seed. If appropriate, this is followed by a drying operation.

The inventive active ingredients or compositions have potent microbicidal activity and can be used for control of unwanted microorganisms, such as fungi and bacteria, in crop protection and in the protection of materials.

Fungicides can be used in crop protection for control of Plasmodiophoromycetes, Oomycetes, Chytridiomycetes, Zygomycetes, Ascomycetes, Basidiomycetes and Deuteromycetes.

Bactericides can be used in crop protection for control of Pseudomonadaceae, Rhizobiaceae, Enterobacteriaceae, Corynebacteriaceae and Streptomycetaceae.

The inventive fungicidal compositions can be used for curative or protective control of phytopathogenic fungi. The invention therefore also relates to curative and protective methods for controlling phytopathogenic fungi through the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

The good plant tolerance of the active ingredients in the concentrations required for control of plant diseases allows treatment of above-ground parts of plants, of propagation stock and seeds, and of the soil.

All plants and parts of plants can be treated in accordance with the invention. Plants in this context are understood to include all plants and plant populations, such as desired and unwanted wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example cuttings, tubers, rhizomes, slips and seeds.

The inventive active ingredients, given good plant compatibility, favorable homeotherm toxicity and good environmental compatibility, are suitable for protection of plants and plant organs, for increasing harvest yields, and for improving the quality of the harvested crop. They can preferably be used as crop protection agents. They are effective against normally sensitive and resistant species and against all or some stages of development.

Plants which can be treated in accordance with the invention include the following main crop plants: corn, soybean, cotton, Brassica oil seeds such as *Brassica napus* (e.g. Canola), *Brassica rapa, B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example *Rosaceae* sp. (for example pome fruits such as apples and pears, but also stone fruits such as apricots, cherries, almonds and peaches, and berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes, potatoes, peppers, aubergines), *Liliaceae* sp., *Compositae* sp. (for example lettuce, artichokes and chicory—including root chicory, endive or common chicory), *Umbelliferae* sp. (for example carrots, parsley, celery and celeriac), *Cucurbitaceae* sp. (for example cucumbers—including gherkins, pumpkins, watermelons, calabashes and melons), *Alliaceae* sp. (for example leeks and onions), *Cruciferae* sp. (for example white cabbage, red cabbage, broccoli, cauliflower, Brussels sprouts, pak choi, kohlrabi, radishes, horseradish, cress and chinese cabbage), *Leguminosae* sp. (for example peanuts, peas, and beans—for example common beans and broad beans), *Chenopodiaceae* sp. (for example Swiss chard, fodder beet, spinach, beetroot), *Malvaceae* (for example okra), *Asparagaceae* (for example asparagus); useful plants and ornamental plants in the garden and woods; and in each case genetically modified types of these plants.

As mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

The inventive treatment method can be used for the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing (an)other gene(s) which is/are present in the plant (using for example antisense technology, cosuppression technology or RNAi technology [RNA interference]). A heterologous gene that is located in the genome is also called a transgene. A transgene that is defined by its specific presence in the plant genome is called a transformation or transgenic event.

Depending on the plant species or plant cultivars, their location and growth conditions (soils, climate, vegetation period, diet), the inventive treatment may also result in superadditive ("synergistic") effects. For example, the following effects which exceed the effects actually to be expected are possible: reduced application rates and/or widened spectrum of activity and/or increased efficacy of the active ingredients and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf colour, earlier flowering, higher quality and/or a higher nutritional value of the harvested products, higher sugar concentration within the fruits, better storage stability and/or processability of the harvested products.

At certain application rates, the inventive active ingredient combinations may also have a fortifying effect in plants. Accordingly, they are suitable for mobilizing the defence system of the plant against attack by unwanted phytopathogenic fungi and/or microorganisms and/or viruses. This may possibly be one of the reasons for the enhanced activity of the inventive combinations for example against fungi. Plant-fortifying (resistance-inducing) substances shall be understood to mean, in the present context, also those substances or combinations of substances which are capable of stimulating the defense system of plants in such a way that, when subsequently inoculated with unwanted phytopathogenic fungi, the plants treated display a substantial degree of resistance to these unwanted phytopathogenic fungi. The inventive substances can therefore be used for protection of plants from attack by the pathogens mentioned within a certain period of time after treatment. The period within which protection is achieved generally extends for from 1 to 10 days, preferably 1 to 7 days, after the treatment of the plants with the active ingredients.

Plants and plant varieties which are preferably treated in accordance with the invention include all plants which have genetic material which imparts particularly advantageous, useful traits to these plants (whether obtained by breeding and/or biotechnological means).

Plants and plant cultivars which are likewise preferably treated in accordance with the invention are resistant to one or more biotic stress factors, meaning that these plants have a better defense against animal and microbial pests, such as nematodes, insects, mites, phytopathogenic fungi, bacteria, viruses and/or viroids.

Examples of nematode-resistant plants are described, for example, in the following U.S. patent applications Ser. Nos. 11/765,491, 11/765,494, 10/926,819, 10/782,020, 12/032, 479, 10/783,417, 10/782,096, 11/657,964, 12/192,904, 11/396,808, 12/166,253, 12/166,239, 12/166,124, 12/166, 209, 11/762,886, 12/364,335, 11/763,947, 12/252,453, 12/209,354, 12/491,396 and 12/497,221.

Plants and plant cultivars which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or lack of shade.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and oil composition, nutritional value, reduction in antinutritional compounds, improved processability and better storage stability.

Plants that may be treated according to the invention are hybrid plants that already express the characteristics of heterosis, or hybrid effect, which results in generally higher yield, vigor, better health and resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for Brassica species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate by various methods. Thus, for example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science, 221, 370-371), the CP4 gene of the bacterium *Agrobacterium* sp. (Barry et al., 1992, Curr. Topics Plant Physiol. 7, 139-145), the genes encoding a *petunia* EPSPS (Shah et al., 1986, Science 233, 478-481), a tomato EPSPS (Gasser et al., 1988, J. Biol. Chem. 263, 4280-4289) or an Eleusine EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the abovementioned genes. Plants which express EPSPS genes which impart glyphosate tolerance have been described. Plants which express other genes which impart glyphosate tolerance, for example decarboxylase genes, have been described. Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such effective detoxifying enzyme is an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyse the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD inhibitors can also be obtained by transforming plants with genes encoding certain enzymes enabling the formation of homogentisate despite the inhibition of the native HPPD enzyme by the HPPD inhibitor. Such plants are described in WO 99/34008 and WO 02/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Other herbicide-resistant plants are plants which have been rendered tolerant to acetolactate synthase (ALS) inhibitors. Known ALS inhibitors include, for example, sulfonylurea, imidazolinone, triazolopyrimidines, pyrimidinyoxy(thio)benzoates, and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (Weed Science 2002, 50, 700-712). The production of sulfonylurea-tolerant plants and imidazolinone-tolerant plants has been described. Further sulfonylurea- and imidazolinone-tolerant plants have also been described.

Further plants tolerant to imidazolinone and/or sulfonylurea can be obtained by induced mutagenesis, by selection in cell cultures in the presence of the herbicide or by mutation breeding (cf., for example, for soybeans U.S. Pat. No. 5,084,082, for rice WO 97/41218, for sugar beet U.S. Pat. No. 5,773,702 and WO 99/057965, for lettuce U.S. Pat. No. 5,198,599 or for sunflower WO 01/065922).

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as, for example:

1) Transgenic plants which synthesize a modified starch which, in its physicochemical characteristics, in particular the amylose content or the amylose/amylopectin ratio, the degree of branching, the average chain length, the side chain distribution, the viscosity behavior, the gelling strength, the starch granule size and/or the starch granule morphology, is changed in comparison with the synthesized starch in wild-type plant cells or plants, so that this modified starch is better suited to specific applications.

2) Transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

4) Transgenic plants or hybrid plants such as onions with particular properties, such as "high soluble solids content", "low pungency" (LP) and/or "long storage" (LS).

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, containing an altered form of cellulose synthase genes;

b) plants, such as cotton plants, which contain an altered form of rsw2 or rsw3 homologous nucleic acids, such as cotton plants with an increased expression of sucrose phosphate synthase;
c) plants, such as cotton plants, with increased expression of sucrose synthase;
d) plants, such as cotton plants, wherein the timing of the plasmodesmatal gating at the basis of the fiber cell is altered, for example through downregulation of fiber-selective β-1,3-glucanase;
e) plants, such as cotton plants, which have fibers with altered reactivity, for example through expression of the N-acetylglucosaminetransferase gene, including nodC, and chitin synthase genes.

Plants or plant cultivars (obtained by plant biotechnology methods such as genetic engineering) which may also be treated according to the invention are plants, such as oilseed rape or related Brassica plants, with altered oil profile characteristics. Such plants can be obtained by genetic transformation, or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, producing oil having a low level of saturated fatty acids.

Plants or plant cultivars (which can be obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related Brassica plants, with altered seed shattering characteristics. Such plants can be obtained by genetic transformation, or by selection of plants containing a mutation imparting such altered characteristics, and include plants such as oilseed rape with retarded or reduced seed shattering.

Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, Md. 20737, USA), for example via the website http://www.aphis.usda.gov/brs/not_reg.html. At the filing date of this application, the petitions with the following information were either granted or pending at the APHIS:

Petition: Identification number of the petition. The technical description of the transformation event can be found in the specific petition document available from APHIS on the website via the petition number. These descriptions are hereby disclosed by reference.
Extension of a petition: Reference to an earlier petition for which an extension of scope or term is being requested.
Institution: Name of the person submitting the petition.
Regulated article: The plant species in question.
Transgenic phenotype: The trait imparted to the plant by the transformation event.
Transformation event or line: The name of the event(s) (sometimes also referred to as line(s)) for which non-regulated status is being requested.
APHIS documents: Various documents which have been published by APHIS with regard to the petition or can be obtained from APHIS on request.

Particularly useful transgenic plants which can be treated in accordance with the invention are plants which comprise one or more genes which code for one or more toxins are the transgenic plants which are sold under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which may be mentioned are maize varieties, cotton varieties and soya bean varieties which are available under the following trade names: Roundup Ready® (tolerance to glyphosates, for example corn, cotton, soybeans), Liberty Link® (tolerance to phosphinothricin, for example oilseed rape), IMI® (tolerance to imidazolinone) and SCS® (tolerance to sulfonylurea, for example corn). Herbicide-resistant plants (plants bred in a conventional manner for herbicide tolerance) which may be mentioned include the varieties sold under the name Clearfield® (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://cera-gm-c.org/index.php?evidcode=&hstIDXCode=&gType=&AbbrCode=&atCode=&stCode=&colDCode=&action=gm_crop_database&mode=Submit).

The inventive active ingredients or compositions can also be used in the protection of materials, for protection of industrial materials against attack and destruction by unwanted microorganisms, for example fungi and insects.

In addition, the inventive compounds can be used as antifouling compositions, alone or in combinations with other active ingredients.

Industrial materials in the present context are understood as meaning non-living materials which have been prepared for use in industry. For example, industrial materials which are to be protected by inventive active ingredients from microbial alteration or destruction may be adhesives, sizes, paper, wallpaper and cardboard, textiles, carpets, leather, wood, paints and plastic articles, cooling lubricants and other materials which can be infected with or destroyed by microorganisms. The range of materials to be protected also includes parts of production plants and buildings, for example cooling water circuits, cooling and heating systems, and ventilation and air conditioning systems, which may be impaired by the proliferation of microorganisms. Industrial materials within the scope of the present invention preferably include adhesives, sizes, paper and cardboard, leather, wood, paints, cooling lubricants and heat transfer fluids, particularly preferably wood. The inventive active ingredients or compositions may prevent adverse effects, such as rotting, decay, discoloration, decoloration or formation of mold. In addition, the inventive compounds can be used for protection of objects which come into contact with saltwater or brackish water, especially hulls, screens, nets, buildings, moorings and signaling systems, from fouling. The inventive method for controlling unwanted fungi can also be employed for protecting storage goods. Here, storage goods are to be understood as meaning natural substances of vegetable or animal origin or processing products thereof of natural origin, for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, whether unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mold.

Non-limiting examples of pathogens of fungal diseases which can be treated in accordance with the invention include: Diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*; diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondita* or *Puccinia triticina*; *Uromyces* species, for example *Uromyces appendiculatus*; diseases caused by pathogens from the group of the oomycetes, for example *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*; leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*); *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola* and *M. fijiensis*; *Phaeosphaeria* species, for example *Phaeosphaeria nodorum*; *Pyrenophora* species, for example *Pyrenophora teres*; *Ramularia* species, for example *Ramularia collo-cygni*; *Rhynchosporium* species, for example *Rhynchosporium secalis*; *Septoria* species, for example *Septoria apii*; *Typhula* species, for example *Typhula incarnata*; *Venturia* species, for example *Venturia inaequalis*; root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, for example *Rhizoctonia solani*; *Tapesia* species, for example *Tapesia acuformis*; *Thielaviopsis* species, for example *Thielaviopsis basicola*; ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example, *Septoria nodorum*; diseases caused by smut fungi, for example *Sphacelotheca* species, for example *Sphacelotheca reiliana*; *Tilletia* species, for example *Tilletia caries*; *T. controversa*; *Urocystis* species, for example *Urocystis occulta*; *Ustilago* species, for example *Ustilago nuda*; *U. nuda tritici*; fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*; seed- and soil-borne rot and wilt diseases, and also diseases of seedlings, caused, for example, by *Fusarium* species, for example *Fusarium culmorum*; *Phytophthora* species, for example *Phytophthora cactorum*; *Pythium* species, for example *Pythium ultimum*; *Rhizoctonia* species, for example *Rhizoctonia solani*; *Sclerotium* species, for example *Sclerotium rolfsii*; cancerous diseases, galls and witches' broom caused, for example, by *Nectria* species, for example *Nectria galligena*; wilt diseases caused, for example, by *Monilinia* species, for example *Monilinia laxa*; deformations of leaves, flowers and fruits caused, for example, by *Taphrina* species, for example *Taphrina deformans*; degenerative diseases of woody plants caused, for example, by *Esca* species, for example *Phaemoniella clamydospora* and *Phaeoacremonium aleophilum* and *Fomitiporia mediterranea*; diseases of flowers and seeds caused, for example, by *Botrytis* species, for example *Botrytis cinerea*; diseases of plant tubers caused, for example, by *Rhizoctonia* species, for example *Rhizoctonia solani*; *Helminthosporium* species, for example *Helminthosporium solani*; diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soybeans can be controlled with preference:

Fungal diseases on leaves, stems, pods and seeds caused, for example, by alternaria leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Microorganisms capable of degrading or altering the industrial materials include, for example, bacteria, fungi, yeasts, algae and slime organisms. The inventive active ingredients preferably act against fungi, especially molds, wood-discoloring and wood-destroying fungi (Basidiomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

In addition, the inventive active ingredients also have very good antimycotic activity. They have a very broad antimycotic activity spectrum, in particular against dermatophytes and yeasts, molds and diphasic fungi, (for example against *Candida* species, such as *Candida albicans, Candida glabrata*), and *Epidermophyton floccosum, Aspergillus* species, such as *Aspergillus niger* and *Aspergillus fumigatus*, *Trichophyton* species, such as *Trichophyton mentagrophytes, Microsporon* species such as *Microsporon canis* and *audouinii*. The enumeration of these fungi in no way constitutes a restriction of the mycotic spectrum that can be controlled, and is merely of illustrative character.

The inventive active ingredients can therefore be used both in medical and in non-medical applications.

In the case of use of the inventive active ingredients as fungicides, the application rates can be varied within a relatively wide range, depending on the kind of application. The application rate of the inventive active ingredients is
- in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);
- in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;
- in the case of soil treatment: from 0.1 to 10 000 g/ha, preferably from 1 to 5000 g/ha.

These application rates are merely illustrative and are not limiting for the purposes of the invention.

The inventive active ingredients or compositions can thus be used to protect plants from attack by the pathogens mentioned for a certain period of time after treatment. The period for which protection is brought about extends generally for 1 to 28 days, preferably for 1 to 14 days, more preferably for 1 to 10 days, even more preferably for 1 to 7 days, after the treatment of the plants with the active ingredients, or for up to 200 days after a seed treatment.

In addition, the inventive treatment can reduce the mycotoxin content in the harvested material and the foodstuffs and feedstuffs prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

If appropriate, the inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active ingredients.

The examples which follow illustrate the invention in detail.

A. CHEMICAL EXAMPLES

1. Preparation of 3-(5-chloropyridin-3-yl)-N-isopropyl-5-methyl-4,5-dihydro-1,2-oxazole-5-carboxamide (example 2.8)

Intermediate 1: 5-chloronicotinaldehyde (5-Chloropyridin-3-yl)methanol (6.3 g) was dissolved in dimethyl sulfoxide (12 ml), triethylamine (18.3 ml) was slowly added dropwise and the sulfur trioxide-pyridine complex (20.9 g) was added in portions (exothermicity: 50° C.). The reaction mixture was stirred for 3 h, adjusted to pH 3 with 2M hydrochloric acid and extracted by shaking twice with EtOAc. The organic phase was washed with saturated $NaHCO_3$ solution, dried over $MgSO_4$ and concentrated at 40° C. Yield: 4.3 g of 5-chloronicotinaldehyde.

Intermediate 2: 5-Chloronicotinaldehyde oxime

Hydroxylamine hydrochloride (2.3 g) and sodium acetate (2.7 g) were initially charged in ethanol (50 ml) under nitrogen (white suspension). 5-Chloronicotinaldehyde (4.3 g) were dissolved in ethanol (120 ml) (30° C., ultrasound bath) and added dropwise thereto within 15 minutes. The reaction mixture was stirred for 2 hours and concentrated at 40° C. Dichloromethane (550 ml) and water (250 ml) were added and the resulting precipitate is filtered off and dried. Yield: 2.1 g of 5-chloronicotinaldehyde oxime.

Intermediate 3: Ethyl 3-(5-chloropyridin-3-yl)-5-methyl-4,5-dihydro-1,2-oxazole-5-carboxylate 5-Chloronicotinaldehyde oxime (2.1 g) was initially charged in N,N-dimethylformamide (200 ml) under nitrogen, and N-chlorosuccinimide (1.9 g) was added (clear yellow solution). The temperature falls at first to 20° C., and then a temperature increase/exothermicity takes place (after 20 minutes: 21° C., after 40 minutes: 24° C., after 55 minutes: 28° C.), and the solution lost color again and was stirred for 4 h. Ethyl methacrylate (2.3 g) was added dropwise within 12 minutes and the reaction mixture was simultaneously cooled to 17° C. with an ice bath. Thereafter, triethylamine (2.8 ml) was added dropwise (a temperature increase takes place; the ice bath was used to keep the reaction mixture at 17° C.). After the addition of triethylamine, the ice bath was removed and the reaction mixture was stirred for a further 18 h and then concentrated at 55° C. The residue was taken up with dichloromethane (200 ml) and washed three times with saturated $NaHCO_3$ solution. The aqueous phases were washed twice with dichloromethane. All the organic phases were collected and washed with saturated NaCl solution and dried over $MgSO_4$. The organic phase was concentrated at 40° C. Yield: 3.9 g of ethyl 3-(5-chloropyridin-3-yl)-5-methyl-4,5-dihydro-1,2-oxazole-5-carboxylate.

Intermediate 4: 3-(5-chloropyridin-3-yl)-5-methyl-4,5-dihydro-1,2-oxazole-5-carboxylic acid Ethyl 3-(5-chloropyridin-3-yl)-5-methyl-4,5-dihydro-1,2-oxazole-5-carboxylate (3.9 g) was taken up in methanol (24 ml) (brown suspension), and sodium hydroxide solution (2M solution, 10.7 ml) was slowly added dropwise while cooling with an ice bath.
Stirring of the reaction mixture while cooling continued for 10 minutes, followed by stirring at RT for another 2 h. The methanol was removed by rotary evaporation at 40° C. and the residue was taken up with water and washed twice with dichloromethane in a separating funnel. The aqueous phase was adjusted to pH 1 with 6M hydrochloric acid and then washed twice with EtOAc. The organic phase was dried with $MgSO_4$ and concentrated by rotary evaporation at 40° C. The oily residue solidified after a while. Yield: 2.6 g of 3-(5-chloropyridin-3-yl)-5-methyl-4,5-dihydro-1,2-oxazole-5-carboxylic acid Final Stage: 3-(5-chloropyridin-3-yl)-N-isopropyl-5-methyl-4,5-dihydro-1,2-oxazole-5-carboxamide 3-(5-Chloropyridin-3-yl)-5-methyl-4,5-dihydro-1,2-oxazole-5-carboxylic acid (100 mg) was initially charged in dichloromethane (10 ml), and 1-hydroxybenzotriazole (56 mg), isopropylamine (49 mg), diisopropylethylamine (107 mg) and 1-(3-dimethylaminopropyl)-3-ethylcarbodiimide hydrochloride (120 mg) were added, and the reaction mixture was stirred at RT for 16 h. Thereafter, $H_2SO_4$ (1 M, 82 µl) and water (1 ml) were added. The reaction mixture was stirred for 10 min and washed with EtOAc. The organic phase was washed with $NaHCO_3$ solution, dried with $MgSO_4$ and concentrated by rotary evaporation at 40° C. The crude product was chromatographed using silica gel. Yield: 80 mg of 3-(5-chloropyridin-3-yl)-N-isopropyl-5-methyl-4,5-dihydro-1,2-oxazole-5-carboxamide.

2. Preparation of: 3-(5-chloropyridin-3-yl)-N-isopropyl-5-methyl-4,5-dihydro-1,2-oxazole-5-carbothioamide (example 2.61)

3-(5-Chloropyridin-3-yl)-N-isopropyl-5-methyl-4,5-dihydro-1,2-oxazole-5-carboxamide (105 mg) was dissolved in toluene (17 ml), and 4-methoxyphenyldithiophosphonic anhydride (91 mg) was added. The reaction mixture was heated in an oil bath to 120° C. for 5 h and then concentrated at 40° C. The crude product was chromatographed using silica gel. Yield: 76 mg of 3-(5-chloropyridin-3-yl)-N-isopropyl-5-methyl-4,5-dihydro-1,2-oxazole-5-carbothioamide.

3. Preparation of: 3-(2-chloro-6-methylpyrimidin-4-yl)-N-[(2-chlorpyridin-4-yl)methyl]-5-methyl-4,5-dihydro-1,2-oxazole-5-carboxamide (example 7.13)

Intermediate 1: (2-Chloro-6-methylpyrimidin-4-yl)methanol

Methyl 2-chloro-6-methylpyrimidine-4-carboxylate (4.0 g) was dissolved in ethanol (46 ml) and cooled with ice, and sodium borohydride (8.0 g) was added in portions. After 30 min, the ice bath was removed and the reaction mixture was stirred for a further 15 min. The reaction mixture was admixed with ice and water, concentrated, extracted with EtOAc, dried over $MgSO_4$ and concentrated at 40° C. The crude product was purified by means of HPLC. Yield: 1.4 g of (2-chloro-6-methylpyrimidin-4-yl)methanol.

Intermediate 2: 2-chloro-6-methylpyrimidine-4-carbaldehyde (2-Chloro-6-methylpyrimidin-4-yl)methanol (1.6 g) was dissolved in dimethyl sulfoxide (150 ml), triethylamine (4.2 ml) was slowly added dropwise and the sulfur trioxide-pyridine complex (4.9 g) was added in portions. The reaction mixture was stirred for 5 h, adjusted to pH 3 with 2M hydrochloric acid and extracted by shaking twice with EtOAc. The organic phase was washed with saturated $NaHCO_3$ solution, dried over $MgSO_4$ and concentrated at 40° C. Yield: 2.0 g of 2-chloro-6-methylpyrimidine-4-carboxaldehyde.

Intermediate 3: 2-Chloro-6-methylpyrimidine-4-carbaldehyde oxime

Hydroxylamine hydrochloride (0.72 g) and sodium acetate (0.85 g) were initially charged in ethanol (50 ml) under nitrogen (white suspension). 2-Chloro-6-methylpyrimidine-4-carboxaldehyde (1.6 g) was dissolved in ethanol (150 ml) and added dropwise thereto within 45 minutes. The reaction mixture was stirred for 20 hours and concentrated at 40° C. Water (100 ml) was added and the mixture was extracted three times with EtOAc. The organic phase was dried over $MgSO_4$ and the crude product was purified via column chromatography. Yield: 0.31 g of 2-chloro-6-methylpyrimidine-4-carbaldehyde oxime.

Intermediate 4: 2-chloro-N-hydroxy-6-methylpyrimidine-4-carboximidoyl chloride

2-Chloro-6-methylpyrimidine-4-carbaldehyde oxime (0.31 g) was initially charged in N,N-dimethylformamide (12 ml) under nitrogen, and N-chlorosuccinimide (0.31 g) was added. After 2 h, the reaction solution was poured onto ice-water (33 ml) and extracted three times with diethyl ether. The organic phase was washed with 0.5 M HCl solution and with sat. NaCl solution, dried over MgSO$_4$ and concentrated at 40° C. Yield: 0.37 g of 2-chloro-N-hydroxy-6-methylpyrimidine-4-carboximidoyl chloride.

Intermediate 5: methyl 3-(2-chloro-6-methylpyrimidin-4-yl)-5-methyl-4,5-dihydro-1,2-oxazole-5-carboxylate 2-Chloro-N-hydroxy-6-methylpyrimidine-4-carboximidoyl chloride (0.37 g) was dissolved in 2-propanol (15 ml), and methyl methacrylate (1.9 g) was added. Sodium hydrogencarbonate (1.6 g) was added and the reaction mixture was heated to 40° C. for 2 h. The reaction mixture was filtered and concentrated at 40° C. The crude product was purified via column chromatography. Yield: 0.37 g of methyl 3-(2-chloro-6-methylpyrimidin-4-yl)-5-methyl-4,5-dihydro-1,2-oxazole-5-carboxylate.

Intermediate 6: 3-(2-chloro-6-methylpyrimidin-4-yl)-5-methyl-4,5-dihydro-1,2-oxazole-5-carboxylic acid Methyl 3-(2-chloro-6-methylpyrimidin-4-yl)-5-methyl-4,5-dihydro-1,2-oxazole-5-carboxylate (0.37 g) was dissolved in THF (320 ml) and water (14 ml), and aqueous 2M LiOH (0.66 ml) was added. The reaction mixture was stirred at RT for a further 3 h and then concentrated at 40° C. The residue was taken up with water and washed twice with EtOAc in a separating funnel. The aqueous phase was adjusted to pH 1 with 2M hydrochloric acid and then extracted twice with EtOAc. The organic phase was dried with MgSO$_4$ and concentrated by rotary evaporation at 40° C. Yield: 0.29 g of 3-(2-chloro-6-methylpyrimidin-4-yl)-5-methyl-4,5-dihydro-1,2-oxazole-5-carboxylic acid.

Final Stage: 3-(2-chloro-6-methylpyrimidin-4-yl)-N-[(2-chlorpyridin-4-yl)methyl]-5-methyl-4,5-dihydro-1,2-oxazole-5-carboxamide 3-(5-Chloropyridin-3-yl)-5-methyl-4,5-dihydro-1,2-oxazole-5-carboxylic acid (87 mg) and N-hydroxysuccinimide (41 mg) were dissolved in dichloromethane (5 ml), and 1-(3-dimethylaminopropyl)-3-ethylcarbodiimide hydrochloride (71 mg) was added. After 2 h, triethylamine (0.2 ml) and 1-(2-chloropyridin-4-yl)methanamine hydrochloride (73 mg) were added and the reaction mixture was stirred at RT for a further 65 h. The reaction mixture was diluted with EtOAc and washed with 2M HCl and sat. NaHCO$_3$ solution. The organic phase was dried with MgSO$_4$ and concentrated by rotary evaporation at 40° C. The crude product was chromatographed using silica gel. Yield: 34 mg of 3-(2-chloro-6-methylpyrimidin-4-yl)-N-[(2-chlorpyridin-4-yl)methyl]-5-methyl-4,5-dihydro-1,2-oxazole-5-carboxamide.

TABLE A

Definitions of the "A—X" radicals in formula (I) which are used for preparation of the inventive compounds in tables 1 to 28

| No. | A—X |
|---|---|
| A.1 | —H |
| A.2 | —CH$_2$—CHF$_2$ |
| A.3 | —CH(CH$_3$)—CH$_2$—O—CH$_3$ |
| A.4 | —CH$_3$ |
| A.5 | —CH$_2$—CF$_2$—CF$_3$ |
| A.6 | —CH(CH$_3$)—CH$_2$—CN |
| A.7 | —CH$_2$—CH(CH$_3$)$_2$ (isobutyl) |
| A.8 | —CH(CF$_3$)$_2$ |
| A.9 | —CH(CH$_3$)—CH(CH$_3$)—O—CH$_3$ |
| A.10 | —CH$_2$—CH$_2$—CH$_2$—CH$_3$ |
| A.11 | —CH$_2$—CH$_2$—CH$_2$—Cl |
| A.12 | —CH$_2$—CH$_2$—CH$_2$—S— |
| A.13 | —CH(CH$_3$)$_2$ |

TABLE A-continued

Definitions of the "A—X" radicals in formula (I) which are used for preparation of the inventive compounds in tables 1 to 28

| No. | A—X |
|---|---|
| A.14 | —CH₂CH₂—Br |
| A.15 | —CH₂CH₂—S(=O)—CH₃ |
| A.16 | —CH₂—C(CH₃)₃ |
| A.17 | —CH₂CH₂—C≡N |
| A.18 | —CH₂CH₂—S(=O)₂—CH₃ |
| A.19 | —CH₂—CH(CH₃)—CH₂CH₃ |
| A.20 | —CH₂—CH=CH₂ |
| A.21 | —CH₂CH₂—S—CH₂CH₃ |
| A.22 | —CH(CH(CH₃)₂)—CH₃ |
| A.23 | —CH₂CH₂—OH |
| A.24 | —CH₂CH₂—S(=O)—CH₂CH₃ |
| A.25 | —CH₂CH₂—CF₃ |
| A.26 | —CH₂CH₂—O—CH₃ |
| A.27 | —CH₂CH₂—S(=O)₂—CH₂CH₃ |
| A.28 | —CH₂CH₂—P(=O)(OCH₂CH₃)₂ |
| A.29 | —CH₂CH₂—N(CH₃)—S(=O)₂—CF₃ |
| A.30 | —CH₂—CH(CH₃)—CF₃ |
| A.31 | —CH₂CH₂—P(=O)(CH₃)₂ |
| A.32 | —CH₂CH₂—N(CH₃)—S(=O)₂—N(CH₃)₂ |
| A.33 | —CH(CH₃)—CF₃ |
| A.34 | —CH₂CH₂—O—C(=O)—NH—CH₂CH₃ |
| A.35 | —CH₂—C≡N |
| A.36 | —CH(CH(CH₃)₂)—CF₃ |
| A.37 | —CH₂CH₂—N(CH₃)—C(=O)—NH—CH₂CH₃ |

TABLE A-continued

Definitions of the "A—X" radicals in formula (I) which are used for preparation of the inventive compounds in tables 1 to 28

| No. | —A—X |
|---|---|
| A.38 | (structure: CH(CH3)CN) |
| A.39 | (structure: CH(CF3)-tetrahydrofuran-3-yl) |
| A.40 | (structure: CH2CH2-O-C(=O)-NH-CH2CF3) |
| A.41 | (structure: C(CH3)2CN) |
| A.42 | (structure: CH2-C≡CH) |
| A.43 | (structure: CH2CH2-NH-C(=O)CH3) |
| A.44 | (structure: CH(CH2CH3)CN) |
| A.45 | (structure: CH(CH3)-C≡CH) |
| A.46 | (structure: CH2CH2-NH-C(=O)CF3) |
| A.47 | (structure: CH(CH2CH3)CN, propyl) |
| A.48 | (structure: C(CH3)2-C≡CH) |
| A.49 | (structure: CH2CH2-N(H)-S(=O)2-CH3) |
| A.50 | (structure: C(CH2CH3)(CH3)CN) |
| A.51 | (structure: CH(CH3)-C≡C-CH3) |
| A.52 | (structure: CH2CH2-N(H)-S(=O)2-CF3) |
| A.53 | (structure: C(CH3)(CH2CH2CH3)CN) |
| A.54 | (structure: C(CH3)2-C≡C-CH3) |
| A.55 | (structure: CH2CH2-N(CH3)-S(=O)2-CH3) |
| A.56 | (structure: C(cyclopropyl)(CH3)CN) |
| A.57 | (structure: CH2-CH(OCH3)2) |

TABLE A-continued

Definitions of the "A—X" radicals in formula (I) which are used for preparation of the inventive compounds in tables 1 to 28

| No. | A—X |
|---|---|
| A.58 | CH(OMe)₂ on CH(CH₃)– |
| A.59 | oxetan-3-yl |
| A.60 | tetrahydropyran-4-yl |
| A.61 | CH(CH₃)C(O)CH₂CH₃ |
| A.62 | thietan-3-yl |
| A.63 | CH₂C(O)OCH₃ |
| A.64 | cyclopropyl |
| A.65 | thietan-3-yl S-oxide |
| A.66 | CH₂C(O)OH |
| A.67 | CH₂-cyclopropyl |
| A.68 | thietan-3-yl S,S-dioxide |
| A.69 | CH(CH₃)C(O)OCH₃ |
| A.70 | CH(CH₃)-cyclopropyl |
| A.71 | cyclopentyl |
| A.72 | C(CH₃)₂C(O)OCH₃ |
| A.73 | 1-methylcyclopropyl |
| A.74 | tetrahydrofuran-3-yl |
| A.75 | 1-(ethoxycarbonyl)cyclopropyl |
| A.76 | 1-cyanocyclopropyl |
| A.77 | CH₂-(tetrahydrofuran-3-yl) |
| A.78 | CH(iPr)C(O)OCH₃ |
| A.79 | 2-fluorocyclopropyl |
| A.80 | CH₂-(1,3-dioxolan-4-yl) |

TABLE A-continued

Definitions of the "A—X" radicals in formula (I) which are used for preparation of the inventive compounds in tables 1 to 28

| No. | —A—X |
|---|---|
| A.81 | methyl 2-methylbutanoate group |
| A.82 | 2-(trifluoromethyl)cyclopropyl group |
| A.83 | 3-methylpentyl group |
| A.84 | methyl 2-vinylbutanoate group |
| A.85 | cyclobutylmethyl group |
| A.86 | tetrahydropyran-3-yl group |
| A.87 | methyl 2-isobutylbutanoate group |
| A.88 | methyl 2-ethylbutanoate group (sec-butyl branch) |
| A.89 | ethyl 4,4,4-trifluoro-3-methylbutanoate group |
| A.90 | ethyl propanoate group |
| A.91 | dimethyl succinate branched group |
| A.92 | ethyl 3-isopropylbutanoate group |
| A.93 | pyridin-3-ylmethyl group |
| A.94 | dimethyl 2-substituted glutarate group |
| A.95 | ethyl 3-ethylbutanoate group |
| A.96 | (6-chloropyridin-3-yl)methyl group |
| A.97 | dimethyl branched diester group |
| A.98 | ethyl 2-methylbutanoate group |
| A.99 | (6-fluoropyridin-3-yl)methyl group |

TABLE A-continued
Definitions of the "A—X" radicals in formula (I) which are used for preparation of the inventive compounds in tables 1 to 28
| No. | —A—X |
|---|---|
| A.100 | 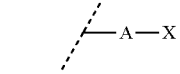 |
| A.101 | 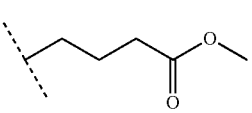 |
| A.102 | 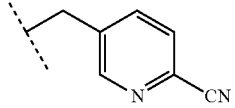 |
| A.103 | 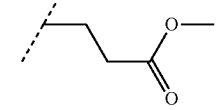 |
| A.104 | 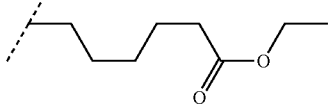 |
| A.105 | 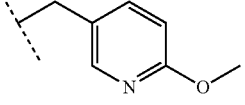 |
| A.106 | 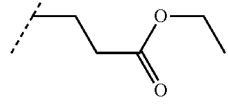 |
| A.107 | 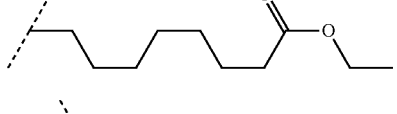 |
| A.108 | 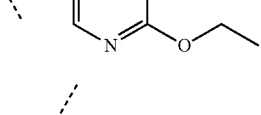 |
| A.109 |  |
| A.110 | 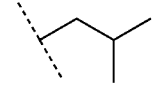 |
| A.111 | 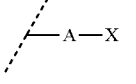 |
| A.112 | 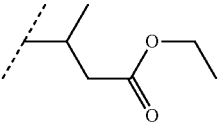 |
| A.113 | 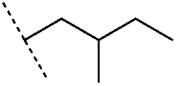 |
| A.114 | 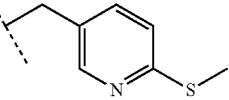 |
| A.115 | 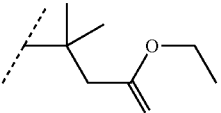 |
| A.116 | 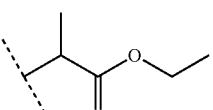 |
| A.117 | 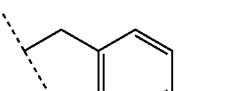 |
| A.118 |  |
| A.119 | 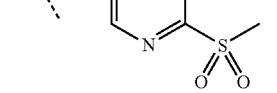 |
| A.120 | 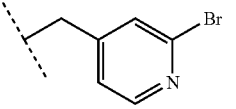 |

TABLE A-continued

Definitions of the "A—X" radicals in formula (I) which are used for preparation of the inventive compounds in tables 1 to 28

| No. | A—X |
|---|---|
| A.121 | 5-(pyridin-2-yl-CF₃)methyl |
| A.122 | 5-(2-methylthio-pyridin-3-yl)isopropyl |
| A.123 | 4-(2-methylthio-pyridin-3-yl)methyl |
| A.124 | 3-(4-chloropyridin-3-yl)methyl |
| A.125 | 5-(2-methylsulfinyl-pyridin-3-yl)isopropyl |
| A.126 | 4-(2-methylsulfinyl-pyridin-3-yl)methyl |
| A.127 | 3-(5-chloropyridin-3-yl)methyl |
| A.128 | 5-(2-methylsulfonyl-pyridin-3-yl)isopropyl |
| A.129 | 4-(2-methylsulfonyl-pyridin-3-yl)methyl |
| A.130 | 3-(pyridin-3-yl)isopropyl |
| A.131 | 5-(2-CF₃-pyridin-3-yl)isopropyl |
| A.132 | 4-(2-methoxy-pyridin-3-yl)methyl |
| A.133 | 5-(2-chloropyridin-3-yl)isopropyl |
| A.134 | 3-(4-chloropyridin-3-yl)isopropyl |
| A.135 | 4-(2-ethoxy-pyridin-3-yl)methyl |
| A.136 | 5-(2-fluoropyridin-3-yl)isopropyl |
| A.137 | 5-(3-chloropyridin-3-yl)isopropyl |
| A.138 | 4-(2-(2,2,2-trifluoroethoxy)-pyridin-3-yl)methyl |
| A.139 | 5-(2-cyanopyridin-3-yl)isopropyl |

TABLE A-continued

Definitions of the "A—X" radicals in formula (I) which are used for preparation of the inventive compounds in tables 1 to 28

| No. | A—X |
|---|---|
| A.140 | 4-pyridylmethyl |
| A.141 | 2-(difluoromethoxy)-4-pyridylmethyl |
| A.142 | 1-(6-methoxypyridin-3-yl)ethyl |
| A.143 | (2-chloropyridin-4-yl)methyl |
| A.144 | (2-trifluoromethoxypyridin-4-yl)methyl |
| A.145 | 1-(6-ethoxypyridin-3-yl)ethyl |
| A.146 | (2-fluoropyridin-4-yl)methyl |
| A.147 | (2-methylpyridin-4-yl)methyl |
| A.148 | (2-ethylpyridin-4-yl)methyl |
| A.149 | 1-(2-fluoropyridin-4-yl)ethyl |
| A.150 | 1-(2-methylpyridin-4-yl)ethyl |
| A.151 | 1-(2-cyclopropylpyridin-4-yl)ethyl |
| A.152 | 1-(2-bromopyridin-4-yl)ethyl |
| A.153 | 1-(2-ethylpyridin-4-yl)ethyl |
| A.154 | (2-propylpyridin-4-yl)methyl |
| A.155 | 1-(2-methylthiopyridin-4-yl)ethyl |
| A.156 | 1-(2-cyclopropylpyridin-4-yl)ethyl |
| A.157 | 1-(2-tert-butylpyridin-4-yl)ethyl |
| A.158 | 1-(2-methylsulfinylpyridin-4-yl)ethyl |
| A.159 | 1-(2-propylpyridin-4-yl)ethyl |

TABLE A-continued

Definitions of the "A—X" radicals in formula (I) which are used for preparation of the inventive compounds in tables 1 to 28

| No. | A—X |
|---|---|
| A.160 | 4-(CH2)-pyridine, 2-CF3 |
| A.161 | 4-(CH(CH3))-pyridine, 2-S(O)2CH3 |
| A.162 | 4-(CH(CH3))-pyridine, 2-C(CH3)3 |
| A.163 | 4-(CH2)-pyridine, 2-CHF2 |
| A.164 | 4-(CH(CH3))-pyridine, 2-OCH3 |
| A.165 | 4-(CH(CH3))-pyridine, 2-CF3 |
| A.166 | 4-(CH2)-pyridine, 2-CN |
| A.167 | 4-(CH(CH3))-pyridine, 2-OEt |
| A.168 | 4-(CH(CH3))-pyridine, 2-CHF2 |
| A.169 | 4-(CH2)-pyridine, 2-C≡CH |
| A.170 | 4-(CH(CH3))-pyridine, 2-OCH2CF3 |
| A.171 | 4-(CH(CH3))-pyridine, 2-CN |
| A.172 | 4-(CH(CH3))-pyridine |
| A.173 | 4-(CH(CH3))-pyridine, 2-OCHF2 |
| A.174 | 4-(CH(CH3))-pyridine, 2-C≡CH |
| A.175 | 4-(CH(CH3))-pyridine, 2-Cl |
| A.176 | 4-(CH(CH3))-pyridine, 2-OCF3 |
| A.177 | 2-(CH2)-pyridine |
| A.178 | 2-(CH2)-pyridine, 3-F, 5-F |
| A.179 | 2-(CH2)-pyrimidine, 4-Cl, 6-Cl |

TABLE A-continued

Definitions of the "A—X" radicals in formula (I) which are used for preparation of the inventive compounds in tables 1 to 28

| No. | A—X |
|---|---|
| A.180 | 1-(2-methyloxazol-4-yl)ethyl |
| A.181 | (3-chloro-5-(trifluoromethyl)pyridin-2-yl)methyl |
| A.182 | (4,6-dimethylpyrimidin-2-yl)methyl |
| A.183 | isoxazol-4-ylmethyl |
| A.184 | 2-(3-chloro-5-(trifluoromethyl)pyridin-2-yl)ethyl |
| A.185 | (4-methoxypyrimidin-2-yl)methyl |
| A.186 | (5-methylisoxazol-4-yl)methyl |
| A.187 | (5-fluoropyridin-2-yl)methyl |
| A.188 | (4,6-dimethoxypyrimidin-2-yl)methyl |
| A.189 | (3,5-dimethylisoxazol-4-yl)methyl |
| A.190 | (5-chloropyridin-2-yl)methyl |
| A.191 | (4-ethoxypyrimidin-2-yl)methyl |
| A.192 | (3-methylisoxazol-5-yl)methyl |
| A.193 | (5-methoxypyridin-2-yl)methyl |
| A.194 | (2-chloropyrimidin-4-yl)methyl |
| A.195 | (3,5-diethylisoxazol-4-yl)methyl |
| A.196 | (6-chloropyridin-2-yl)methyl |
| A.197 | pyrimidin-4-ylmethyl |
| A.198 | (3-methoxy-5-methylisoxazol-4-yl)methyl |
| A.199 | (6-cyanopyridin-2-yl)methyl |

TABLE A-continued

Definitions of the "A—X" radicals in formula (I) which are used for preparation of the inventive compounds in tables 1 to 28

| No. | A—X |
|---|---|
| A.200 | 4-chloropyrimidin-6-yl-methyl (pyrimidine with Cl) |
| A.201 | (1-methyl-1H-pyrazol-4-yl)methyl |
| A.202 | pyrimidin-2-ylmethyl |
| A.203 | (2-methyl-1,3-oxazol-4-yl)methyl |
| A.204 | (1-ethyl-1H-pyrazol-4-yl)methyl |
| A.205 | (4-chloropyrimidin-2-yl)methyl |
| A.206 | (2,5-dimethyl-1,3-oxazol-4-yl)methyl |
| A.207 | [1-(2,2,2-trifluoroethyl)-1H-pyrazol-4-yl]methyl |
| A.208 | [1-(2,2-difluoroethyl)-1H-pyrazol-4-yl]methyl |
| A.209 | 1-[1-(2,2,2-trifluoroethyl)-1H-pyrazol-4-yl]-1-methylethyl |
| A.210 | 2-(1-ethyl-1H-pyrazol-4-yl)ethyl |
| A.211 | 2-(1-propyl-1H-pyrazol-4-yl)ethyl |
| A.212 | 1-[1-(2,2-difluoroethyl)-1H-pyrazol-4-yl]-1-methylethyl |
| A.213 | 3-[1-(2,2,2-trifluoroethyl)-1H-pyrazol-4-yl]propyl |
| A.214 | (1-cyclopropyl-1H-pyrazol-4-yl)methyl |
| A.215 | 1-(1-propyl-1H-pyrazol-4-yl)-1-methylethyl |
| A.216 | 3-[1-(2,2-difluoroethyl)-1H-pyrazol-4-yl]propyl |
| A.217 | (1,3-dimethyl-1H-pyrazol-4-yl)methyl |
| A.218 | 1-(1-cyclopropyl-1H-pyrazol-4-yl)-1-methylethyl |
| A.219 | 3-(1-propyl-1H-pyrazol-4-yl)propyl |

TABLE A-continued

Definitions of the "A—X" radicals in formula (I) which are used for preparation of the inventive compounds in tables 1 to 28

| No. | A—X |
|---|---|
| A.220 | (pyrazole, N-ethyl, 3-methyl, attached at 4-position via CH2) |
| A.221 | (pyrazole, N-methyl, 3-methyl, attached at 4-position via CH(CH3)) |
| A.222 | (pyrazole, N-cyclopropyl, attached at 4-position via CH2CH2) |
| A.223 | (pyrazole, N-ethyl, 3-Cl, attached at 4-position via CH2) |
| A.224 | (pyrazole, N-ethyl, 3-methyl, attached at 4-position via CH(CH3)) |
| A.225 | (pyrazole, N-methyl, 3-methyl, attached at 4-position via CH2CH2) |
| A.226 | (pyrazole, N-propyl, 3-Cl, attached at 4-position via CH2) |
| A.227 | (pyrazole, N-ethyl, 3-Cl, attached at 4-position via CH(CH3)) |
| A.228 | (pyrazole, N-ethyl, 3-methyl, attached at 4-position via CH2CH2) |
| A.229 | (pyrazole, N-propyl, 3-methyl, attached at 4-position via CH2) |
| A.230 | (pyrazole, N-propyl, 3-Cl, attached at 4-position via CH(CH3)) |
| A.231 | (pyrazole, N-ethyl, 3-Cl, attached at 4-position via CH2CH2) |
| A.232 | (pyrazole, N-methyl, attached at 4-position via CH(CH3)) |
| A.233 | (pyrazole, N-propyl, 3-methyl, attached at 4-position via CH(CH3)) |
| A.234 | (pyrazole, N-propyl, 3-Cl, attached at 4-position via CH2CH2) |
| A.135 | (pyrazole, N-ethyl, attached at 4-position via CH(CH3)) |
| A.236 | (pyrazole, N-methyl, attached at 4-position via CH2CH2) |
| A.237 | (pyrazole, N-propyl, 3-methyl, attached at 4-position via CH2CH2) |
| A.238 | (pyridine, 2-Cl, attached at 3-position via CH2) |

TABLE A-continued

Definitions of the "A—X" radicals in formula (I) which are used for preparation of the inventive compounds in tables 1 to 28

| No. | A—X |
|---|---|
| A.239 | 3-chloropyridin-4-ylmethyl |
| A.240 | 3,5-dimethylisoxazol-4-yl |

In analogy to the preparation of the abovementioned compounds and in accordance with the general details of the preparation, the compounds specified in the following tables are obtainable.

TABLE 1

| No. | $R^1$ | $R^2$ | $R^3$ | $R^4$ | $R^A$ | $R^B$ | $R^C$ | $R^D$ | Y | A—X |
|---|---|---|---|---|---|---|---|---|---|---|
| 1.1 | H | H | Me | H | Me | H | H | H | O | A.7 |
| 1.2 | H | H | Me | H | $CF_3$ | H | H | H | O | A.7 |
| 1.3 | H | H | Me | H | Me | H | H | H | O | A.13 |
| 1.4 | H | H | Me | H | $CF_3$ | H | H | H | O | A.13 |
| 1.5 | H | H | Me | H | Br | H | H | H | O | A.13 |
| 1.6 | H | H | Me | H | H | H | Cl | H | O | A.13 |
| 1.7 | H | H | Me | H | Me | H | H | H | O | A.25 |
| 1.8 | H | H | Me | H | $CF_3$ | H | H | H | O | A.25 |
| 1.9 | H | H | Me | H | Cl | H | H | H | O | A.25 |
| 1.10 | H | H | Me | H | Br | H | H | H | O | A.25 |
| 1.11 | H | H | Me | H | H | H | Cl | H | O | A.25 |
| 1.12 | H | H | Me | H | H | H | Cl | H | O | A.35 |
| 1.13 | H | H | Me | H | Me | H | H | H | O | A.64 |
| 1.14 | H | H | Me | H | $CF_3$ | H | H | H | O | A.64 |
| 1.15 | H | H | Me | H | OMe | H | H | H | O | A.64 |
| 1.16 | H | H | Me | H | Cl | H | H | H | O | A.64 |
| 1.17 | H | H | Me | H | Br | H | H | H | O | A.64 |
| 1.18 | H | H | Me | H | H | H | Cl | H | O | A.64 |
| 1.19 | H | H | Me | H | OMe | H | H | H | O | A.101 |
| 1.20 | H | H | Me | H | Me | H | H | H | O | A.103 |
| 1.21 | H | H | Me | H | OMe | H | H | H | O | A.103 |
| 1.22 | H | H | Me | H | Cl | H | H | H | O | A.103 |
| 1.23 | H | H | Me | H | Br | H | H | H | O | A.103 |
| 1.24 | H | H | Me | H | H | H | Cl | H | O | A.103 |
| 1.25 | H | H | Me | H | Me | H | H | H | O | A.109 |
| 1.26 | H | H | Me | H | Cl | H | H | H | O | A.109 |
| 1.27 | H | H | Me | H | Br | H | H | H | O | A.109 |
| 1.28 | H | H | Me | H | $CF_3$ | H | H | H | O | A.143 |
| 1.29 | H | H | Me | H | OMe | H | H | H | O | A.143 |
| 1.30 | H | H | Me | H | Cl | H | Cl | H | O | A.143 |
| 1.31 | H | H | Me | H | H | H | H | H | O | A.220 |
| 1.32 | H | H | Me | H | Me | H | H | H | O | A.220 |
| 1.33 | H | H | Me | H | $CF_3$ | H | H | H | O | A.220 |
| 1.34 | H | H | Me | H | OMe | H | H | H | O | A.220 |
| 1.35 | H | H | Me | H | Cl | H | H | H | O | A.220 |
| 1.36 | H | H | Me | H | Br | H | H | H | O | A.220 |
| 1.37 | H | H | Me | H | H | H | Cl | H | O | A.220 |
| 1.38 | H | H | Me | H | Cl | H | Cl | H | O | A.220 |
| 1.39 | H | H | OMe | H | OMe | H | H | H | O | A.64 |
| 1.40 | H | H | Vinyl | H | Me | H | H | H | O | A.64 |
| 1.41 | H | H | Me | H | Me | H | H | H | S | A.103 |
| 1.42 | H | H | Me | H | $CF_3$ | H | H | H | S | A.204 |

TABLE 2

| No. | $R^1$ | $R^2$ | $R^3$ | $R^4$ | $R^A$ | $R^B$ | $R^C$ | $R^D$ | Y | A—X |
|---|---|---|---|---|---|---|---|---|---|---|
| 2.1 | H | H | Me | H | H | H | Cl | H | O | A.2 |
| 2.2 | H | H | Me | H | H | H | H | H | O | A.4 |
| 2.3 | H | H | Me | H | H | Cl | H | H | O | A.4 |
| 2.4 | H | H | Me | H | H | H | F | H | O | A.7 |
| 2.5 | H | H | Me | H | H | H | Br | H | O | A.7 |
| 2.6 | H | H | Me | H | H | H | OMe | H | O | A.13 |
| 2.7 | H | H | Me | H | H | H | F | H | O | A.13 |
| 2.8 | H | H | Me | H | H | H | Cl | H | O | A.13 |
| 2.9 | H | H | Me | H | H | H | Br | H | O | A.13 |
| 2.10 | H | H | Me | H | H | OMe | H | H | O | A.25 |
| 2.11 | H | H | Me | H | H | H | CN | H | O | A.25 |
| 2.12 | H | H | Me | H | H | H | OMe | H | O | A.25 |
| 2.13 | H | H | Me | H | H | H | F | H | O | A.25 |
| 2.14 | H | H | Me | H | H | H | Cl | H | O | A.25 |
| 2.15 | H | H | Me | H | H | H | Br | H | O | A.25 |
| 2.16 | H | H | Me | H | H | H | F | H | O | A.35 |
| 2.17 | H | H | Me | H | H | H | Br | H | O | A.35 |
| 2.18 | H | H | Me | H | H | H | Cl | H | O | A.38 |
| 2.19 | H | H | Me | H | H | H | F | H | O | A.59 |
| 2.20 | H | H | Me | H | H | H | H | H | O | A.64 |
| 2.21 | H | H | Me | H | H | OMe | H | H | O | A.64 |
| 2.22 | H | H | Me | H | H | Cl | H | H | O | A.64 |
| 2.23 | H | H | Me | H | H | H | Me | H | O | A.64 |
| 2.24 | H | H | Me | H | H | H | CN | H | O | A.64 |
| 2.25 | H | H | Me | H | H | H | F | H | O | A.64 |
| 2.26 | H | H | Me | H | H | H | Cl | H | O | A.64 |
| 2.27 | H | H | Me | H | H | H | Br | H | O | A.64 |
| 2.28 | H | H | Me | H | H | H | Cl | H | O | A.74 |
| 2.29 | H | H | Me | H | H | H | H | H | O | A.101 |
| 2.30 | H | H | Me | H | H | H | H | H | O | A.103 |
| 2.31 | H | H | Me | H | H | H | CN | H | O | A.103 |
| 2.32 | H | H | Me | H | H | H | F | H | O | A.103 |
| 2.33 | H | H | Me | H | H | H | Cl | H | O | A.103 |
| 2.34 | H | H | Me | H | H | H | Br | H | O | A.103 |
| 2.35 | H | H | Me | H | H | OMe | H | H | O | A.106 |
| 2.36 | H | H | Me | H | H | OMe | H | H | O | A.109 |
| 2.37 | H | H | Me | H | H | H | Br | H | O | A.109 |
| 2.38 | H | H | Me | H | H | OMe | H | H | O | A.112 |
| 2.39 | H | H | Me | H | H | H | Cl | H | O | A.112 |
| 2.40 | H | H | Me | H | H | H | Cl | H | O | A.132 |
| 2.41 | H | H | Me | H | H | H | Cl | H | O | A.143 |
| 2.42 | H | H | Me | H | H | H | Cl | H | O | A.146 |
| 2.43 | H | H | Me | H | H | H | H | H | O | A.202 |
| 2.44 | H | H | Me | H | H | OMe | H | H | O | A.204 |
| 2.45 | H | H | Me | H | H | H | Cl | H | O | A.204 |

TABLE 2-continued

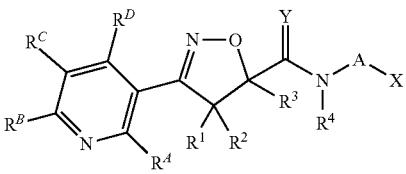

| No. | R¹ | R² | R³ | R⁴ | $R^A$ | $R^B$ | $R^C$ | $R^D$ | Y | A—X |
|---|---|---|---|---|---|---|---|---|---|---|
| 2.46 | H | H | Me | H | H | H | H | H | O | A.220 |
| 2.47 | H | H | Me | H | H | OMe | H | H | O | A.220 |
| 2.48 | H | H | Me | H | H | Cl | H | H | O | A.220 |
| 2.49 | H | H | Me | H | H | H | CN | H | O | A.220 |
| 2.50 | H | H | Me | H | H | H | OMe | H | O | A.220 |
| 2.51 | H | H | Me | H | H | H | F | H | O | A.220 |
| 2.52 | H | H | Me | H | H | H | Cl | H | O | A.220 |
| 2.53 | H | H | Me | H | H | H | Br | H | O | A.220 |
| 2.54 | H | H | Et | H | H | Cl | H | H | O | A.4 |
| 2.55 | H | H | OMe | H | H | H | H | H | O | A.64 |
| 2.56 | H | H | OMe | H | H | H | H | H | O | A.143 |
| 2.57 | H | H | OMe | H | H | H | H | H | O | A.202 |
| 2.58 | H | H | OMe | H | H | H | Cl | H | O | A.220 |
| 2.59 | H | H | Vinyl | H | H | H | Cl | H | O | A.64 |
| 2.60 | H | H | Vinyl | H | H | H | Cl | H | O | A.220 |
| 2.61 | H | H | Me | H | H | H | Cl | H | S | A.13 |
| 2.62 | H | H | Me | H | H | H | Cl | H | S | A.74 |
| 2.63 | H | H | Me | H | H | H | Cl | H | S | A.143 |
| 2.64 | H | H | Me | H | H | H | Cl | H | S | A.220 |
| 2.65 | H | H | Me | Me | H | Cl | H | H | O | A.4 |
| 2.66 | H | H | Me | Me | H | H | Cl | H | O | A.220 |

TABLE 3

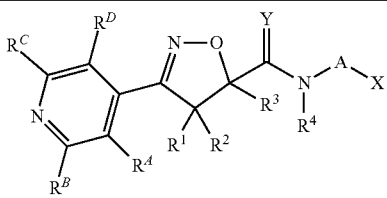

| No. | R¹ | R² | R³ | R⁴ | $R^A$ | $R^B$ | $R^C$ | $R^D$ | Y | A—X |
|---|---|---|---|---|---|---|---|---|---|---|
| 3.1 | H | H | Me | H | H | Cl | H | H | O | A.13 |
| 3.2 | H | H | Me | H | H | Cl | H | H | O | A.25 |
| 3.3 | H | H | Me | H | H | Cl | Cl | H | O | A.25 |
| 3.4 | H | H | Me | H | H | Cl | H | H | O | A.38 |
| 3.5 | H | H | Me | H | H | Cl | Cl | H | O | A.38 |
| 3.6 | H | H | Me | H | H | H | H | H | O | A.64 |
| 3.7 | H | H | Me | H | H | Cl | H | H | O | A.64 |
| 3.8 | H | H | Me | H | H | Cl | Cl | H | O | A.64 |
| 3.9 | H | H | Me | H | H | Cl | H | H | O | A.74 |
| 3.10 | H | H | Me | H | H | Cl | Cl | H | O | A.74 |
| 3.11 | H | H | Me | H | H | Cl | H | H | O | A.112 |
| 3.12 | H | H | Me | H | H | Cl | Cl | H | O | A.112 |
| 3.13 | H | H | Me | H | H | Cl | H | H | O | A.143 |
| 3.14 | H | H | Me | H | H | Cl | Cl | H | O | A.143 |
| 3.15 | H | H | Me | H | H | OMe | H | H | O | A.220 |
| 3.16 | H | H | Me | H | H | Me | H | H | O | A.220 |
| 3.17 | H | H | Me | H | H | CF₃ | H | H | O | A.220 |
| 3.18 | H | H | Me | H | H | Cl | H | H | O | A.220 |
| 3.19 | H | H | Me | H | H | Cl | Cl | H | O | A.220 |
| 3.20 | H | H | Me | H | H | Cl | H | H | S | A.220 |

TABLE 4

| No. | R¹ | R² | R³ | R⁴ | $R^A$ | $R^B$ | $R^C$ | Y | A—X |
|---|---|---|---|---|---|---|---|---|---|
| 4.1 | H | H | Me | H | H | Cl | H | O | A.13 |
| 4.2 | H | H | Me | H | H | H | H | O | A.64 |
| 4.3 | H | H | Me | H | H | Cl | H | O | A.64 |
| 4.4 | H | H | Me | H | H | Me | H | O | A.64 |
| 4.5 | H | H | Me | H | H | Cl | H | O | A.64 |
| 4.6 | H | H | Me | H | H | H | H | O | A.220 |
| 4.7 | H | H | Me | H | H | Me | H | O | A.220 |
| 4.8 | H | H | Me | H | H | Cl | H | O | A.220 |
| 4.9 | H | H | Me | H | H | H | H | S | A.220 |

TABLE 5

| No. | R¹ | R² | R³ | R⁴ | $R^A$ | $R^B$ | $R^C$ | Y | A—X |
|---|---|---|---|---|---|---|---|---|---|
| 5.1 | H | H | Me | H | H | H | H | O | A.13 |
| 5.2 | H | H | Me | H | H | H | H | O | A.64 |
| 5.3 | H | H | Me | H | H | Me | H | O | A.64 |
| 5.4 | H | H | Me | H | H | Cl | H | O | A.64 |
| 5.5 | H | H | Me | H | H | H | H | O | A.220 |
| 5.6 | H | H | Me | H | H | Me | H | O | A.220 |
| 5.7 | H | H | Me | H | H | Cl | H | O | A.220 |
| 5.8 | H | H | Me | H | H | H | H | S | A.64 |
| 5.9 | H | H | Me | H | H | H | H | S | A.220 |

TABLE 6

| No. | R¹ | R² | R³ | R⁴ | $R^A$ | $R^B$ | $R^C$ | Y | A—X |
|---|---|---|---|---|---|---|---|---|---|
| 6.1 | H | H | Me | H | OMe | H | OMe | O | A.7 |
| 6.2 | H | H | Me | H | Me | H | Me | O | A.13 |
| 6.3 | H | H | Me | H | OMe | H | OMe | O | A.13 |
| 6.4 | H | H | Me | H | OMe | H | OMe | O | A.25 |
| 6.5 | H | H | Me | H | Me | H | Me | O | A.38 |
| 6.6 | H | H | Me | H | Me | H | Me | O | A.64 |
| 6.7 | H | H | Me | H | OMe | H | OMe | O | A.64 |
| 6.8 | H | H | Me | H | Me | H | Me | O | A.74 |
| 6.9 | H | H | Me | H | Me | H | Me | O | A.103 |
| 6.10 | H | H | Me | H | OMe | H | OMe | O | A.103 |
| 6.11 | H | H | Me | H | OMe | H | OMe | O | A.109 |
| 6.12 | H | H | Me | H | Me | H | Me | O | A.112 |
| 6.13 | H | H | Me | H | Me | H | Me | O | A.143 |
| 6.14 | H | H | Me | H | Me | H | Me | O | A.146 |
| 6.15 | H | H | Me | H | Me | H | Me | O | A.204 |
| 6.16 | H | H | Me | H | Me | H | Me | O | A.220 |

TABLE 6-continued

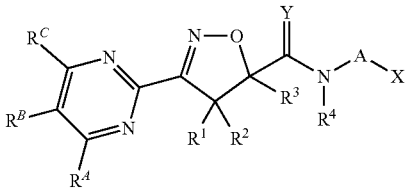

| No. | R¹ | R² | R³ | R⁴ | Rᴬ | Rᴮ | Rᶜ | Y | A—X |
|---|---|---|---|---|---|---|---|---|---|
| 6.17 | H | H | Me | H | OMe | H | OMe | O | A.220 |
| 6.18 | H | H | Me | H | Me | H | Me | O | A.223 |
| 6.19 | H | H | Me | H | Me | H | Me | S | A.74 |
| 6.20 | H | H | Me | H | Me | H | Me | S | A.220 |

TABLE 7

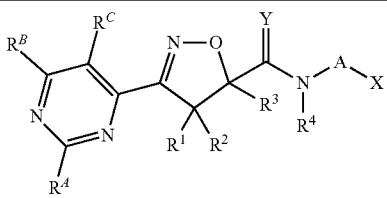

| No. | R¹ | R² | R³ | R⁴ | Rᴬ | Rᴮ | Rᶜ | Y | A—X |
|---|---|---|---|---|---|---|---|---|---|
| 7.1 | H | H | Me | H | Cl | Me | H | O | A.13 |
| 7.2 | H | H | Me | H | OMe | Me | H | O | A.13 |
| 7.3 | H | H | Me | H | Cl | Me | H | O | A.38 |
| 7.4 | H | H | Me | H | OMe | Me | H | O | A.38 |
| 7.5 | H | H | Me | H | Cl | Me | H | O | A.64 |
| 7.6 | H | H | Me | H | OMe | Me | H | O | A.64 |
| 7.7 | H | H | Me | H | Cl | Me | H | O | A.74 |
| 7.8 | H | H | Me | H | OMe | Me | H | O | A.74 |
| 7.9 | H | H | Me | H | Cl | Me | H | O | A.106 |
| 7.10 | H | H | Me | H | OMe | Me | H | O | A.106 |
| 7.11 | H | H | Me | H | Cl | Me | H | O | A.112 |
| 7.12 | H | H | Me | H | OMe | Me | H | O | A.112 |
| 7.13 | H | H | Me | H | Cl | Me | H | O | A.143 |
| 7.14 | H | H | Me | H | OMe | Me | H | O | A.143 |
| 7.15 | H | H | Me | H | Cl | Me | H | O | A.146 |
| 7.16 | H | H | Me | H | OMe | Me | H | O | A.146 |
| 7.17 | H | H | Me | H | Cl | Me | H | O | A.204 |
| 7.18 | H | H | Me | H | OMe | Me | H | O | A.204 |
| 7.19 | H | H | Me | H | Cl | Me | H | O | A.220 |
| 7.20 | H | H | Me | H | OMe | Me | H | O | A.220 |
| 7.21 | H | H | OMe | H | Cl | Me | H | O | A.64 |
| 7.22 | H | H | OMe | H | OMe | Me | H | S | A.64 |

TABLE 8

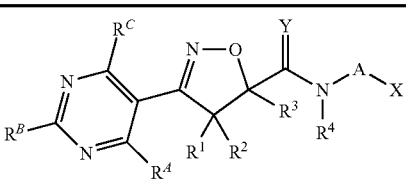

| No. | R¹ | R² | R³ | R⁴ | Rᴬ | Rᴮ | Rᶜ | Y | A—X |
|---|---|---|---|---|---|---|---|---|---|
| 8.1 | H | H | Me | H | H | H | H | O | A.13 |
| 8.2 | H | H | Me | H | H | Cl | H | O | A.13 |
| 8.3 | H | H | Me | H | H | H | H | O | A.38 |
| 8.4 | H | H | Me | H | H | Cl | H | O | A.38 |
| 8.5 | H | H | Me | H | H | H | H | O | A.64 |
| 8.6 | H | H | Me | H | H | Cl | H | O | A.64 |
| 8.7 | H | H | Me | H | H | H | H | O | A.74 |
| 8.8 | H | H | Me | H | H | Cl | H | O | A.74 |
| 8.9 | H | H | Me | H | H | H | H | O | A.103 |

TABLE 8-continued

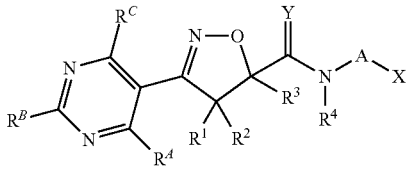

| No. | R¹ | R² | R³ | R⁴ | Rᴬ | Rᴮ | Rᶜ | Y | A—X |
|---|---|---|---|---|---|---|---|---|---|
| 8.10 | H | H | Me | H | H | Cl | H | O | A.103 |
| 8.11 | H | H | Me | H | H | H | H | O | A.112 |
| 8.12 | H | H | Me | H | H | Cl | H | O | A.112 |
| 8.13 | H | H | Me | H | H | H | H | O | A.143 |
| 8.14 | H | H | Me | H | H | Cl | H | O | A.143 |
| 8.15 | H | H | Me | H | H | H | H | O | A.146 |
| 8.16 | H | H | Me | H | H | Cl | H | O | A.146 |
| 8.17 | H | H | Me | H | H | H | H | O | A.220 |
| 8.18 | H | H | Me | H | H | Cl | H | O | A.220 |
| 8.19 | H | H | OMe | H | H | H | H | O | A.64 |
| 8.20 | H | H | Me | H | H | H | H | S | A.64 |

TABLE 9

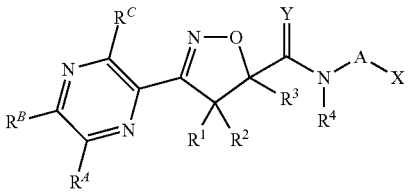

| No. | R¹ | R² | R³ | R⁴ | Rᴬ | Rᴮ | Rᶜ | Y | A—X |
|---|---|---|---|---|---|---|---|---|---|
| 9.1 | H | H | Me | H | Me | H | H | O | A.38 |
| 9.2 | H | H | Me | H | Cl | H | H | O | A.38 |
| 9.3 | H | H | Me | H | Me | H | H | O | A.64 |
| 9.4 | H | H | Me | H | Cl | H | H | O | A.64 |
| 9.5 | H | H | Me | H | Me | H | H | O | A.74 |
| 9.6 | H | H | Me | H | Cl | H | H | O | A.74 |
| 9.7 | H | H | Me | H | Me | H | H | O | A.103 |
| 9.8 | H | H | Me | H | Cl | H | H | O | A.103 |
| 9.9 | H | H | Me | H | Me | H | H | O | A.112 |
| 9.10 | H | H | Me | H | Cl | H | H | O | A.112 |
| 9.11 | H | H | Me | H | Me | H | H | O | A.143 |
| 9.12 | H | H | Me | H | Cl | H | H | O | A.143 |
| 9.13 | H | H | Me | H | Me | H | H | O | A.146 |
| 9.14 | H | H | Me | H | Cl | H | H | O | A.146 |
| 9.15 | H | H | Me | H | Me | H | H | O | A.204 |
| 9.16 | H | H | Me | H | Cl | H | H | O | A.204 |
| 9.17 | H | H | Me | H | Me | H | H | O | A.220 |
| 9.18 | H | H | Me | H | Cl | H | H | O | A.220 |
| 9.19 | H | H | OMe | H | Cl | H | H | O | A.64 |
| 9.20 | H | H | Me | H | Cl | H | H | S | A.204 |

TABLE 10

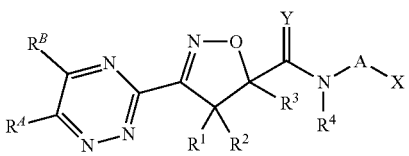

| No. | R¹ | R² | R³ | R⁴ | Rᴬ | Rᴮ | Y | A—X |
|---|---|---|---|---|---|---|---|---|
| 10.1 | H | H | Me | H | H | H | O | A.64 |
| 10.2 | H | H | Me | H | H | Me | O | A.64 |
| 10.3 | H | H | Me | H | H | H | O | A.74 |
| 10.4 | H | H | Me | H | H | Me | O | A.74 |
| 10.5 | H | H | Me | H | H | H | O | A.112 |
| 10.6 | H | H | Me | H | H | Me | O | A.112 |

TABLE 10-continued

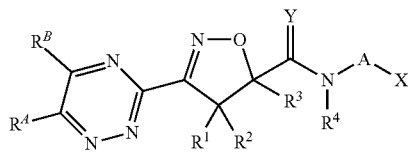

| No. | R¹ | R² | R³ | R⁴ | R^A | R^B | Y | A—X |
|---|---|---|---|---|---|---|---|---|
| 10.7 | H | H | Me | H | H | H | O | A.220 |
| 10.8 | H | H | Me | H | H | Me | O | A.220 |
| 10.9 | H | H | Me | H | H | H | S | A.220 |

TABLE 11

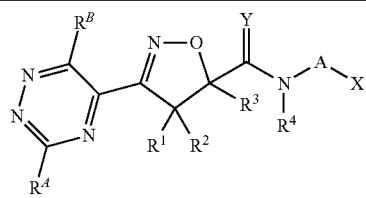

| No. | R¹ | R² | R³ | R⁴ | R^A | R^B | Y | A—X |
|---|---|---|---|---|---|---|---|---|
| 11.1 | H | H | Me | H | H | H | O | A.64 |
| 11.2 | H | H | Me | H | Me | H | O | A.64 |
| 11.3 | H | H | Me | H | H | H | O | A.74 |
| 11.4 | H | H | Me | H | Me | H | O | A.74 |
| 11.5 | H | H | Me | H | H | H | O | A.112 |
| 11.6 | H | H | Me | H | Me | H | O | A.112 |
| 11.7 | H | H | Me | H | H | H | O | A.143 |
| 11.8 | H | H | Me | H | Me | H | O | A.143 |
| 11.9 | H | H | Me | H | H | H | O | A.146 |
| 11.10 | H | H | Me | H | Me | H | O | A.146 |
| 11.11 | H | H | Me | H | H | H | O | A.204 |
| 11.12 | H | H | Me | H | Me | H | O | A.204 |
| 11.13 | H | H | Me | H | H | H | O | A.220 |
| 11.14 | H | H | Me | H | Me | H | O | A.220 |
| 11.15 | H | H | OMe | H | Me | H | O | A.13 |
| 11.16 | H | H | Et | H | Me | H | O | A.64 |
| 11.17 | H | H | Vinyl | H | Me | H | O | A.64 |
| 11.18 | H | H | Vinyl | H | Me | H | O | A.220 |
| 11.19 | H | H | Me | H | Me | H | S | A.64 |
| 11.20 | H | H | Me | H | Me | H | S | A.220 |

TABLE 12

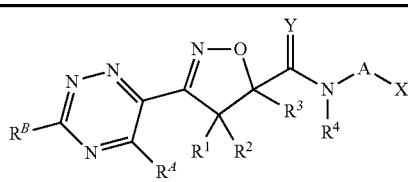

| No. | R¹ | R² | R³ | R⁴ | R^A | R^B | Y | A—X |
|---|---|---|---|---|---|---|---|---|
| 12.1 | H | H | Me | H | H | H | O | A.64 |
| 12.2 | H | H | Me | H | H | Me | O | A.64 |
| 12.3 | H | H | Me | H | H | H | O | A.74 |
| 12.4 | H | H | Me | H | H | Me | O | A.74 |
| 12.5 | H | H | Me | H | H | H | O | A.112 |
| 12.6 | H | H | Me | H | H | Me | O | A.112 |
| 12.7 | H | H | Me | H | H | H | O | A.220 |
| 12.8 | H | H | Me | H | H | Me | O | A.220 |
| 12.9 | H | H | Me | H | H | H | O | A.220 |

TABLE 13

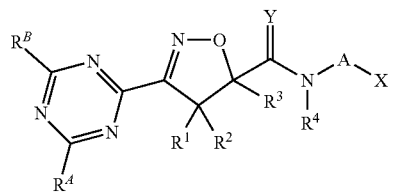

| No. | R¹ | R² | R³ | R⁴ | R^A | R^B | Y | A—X |
|---|---|---|---|---|---|---|---|---|
| 13.1 | H | H | Me | H | H | H | O | A.64 |
| 13.2 | H | H | Me | H | Me | H | O | A.64 |
| 13.3 | H | H | Me | H | H | H | O | A.74 |
| 13.4 | H | H | Me | H | Me | H | O | A.74 |
| 13.5 | H | H | Me | H | H | H | O | A.112 |
| 13.6 | H | H | Me | H | Me | H | O | A.112 |
| 13.7 | H | H | Me | H | H | H | O | A.220 |
| 13.8 | H | H | Me | H | Me | H | O | A.220 |
| 13.9 | H | H | Me | H | H | H | S | A.220 |

TABLE 14

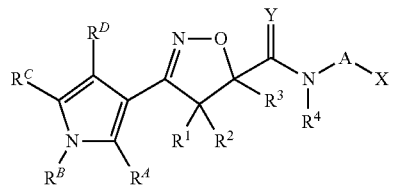

| No. | R¹ | R² | R³ | R⁴ | R^A | R^B | R^C | R^D | Y | A—X |
|---|---|---|---|---|---|---|---|---|---|---|
| 14.1 | H | H | Me | H | H | Me | H | H | O | A.64 |
| 14.2 | H | H | Me | H | H | Et | H | H | O | A.64 |
| 14.3 | H | H | Me | H | H | Me | H | H | O | A.74 |
| 14.4 | H | H | Me | H | H | Et | H | H | O | A.74 |
| 14.5 | H | H | Me | H | H | Me | H | H | O | A.112 |
| 14.6 | H | H | Me | H | H | Et | H | H | O | A.112 |
| 14.7 | H | H | Me | H | H | Me | H | H | O | A.220 |
| 14.8 | H | H | Me | H | H | Et | H | H | O | A.220 |
| 14.9 | H | H | Me | H | H | Me | H | H | S | A.220 |

TABLE 15

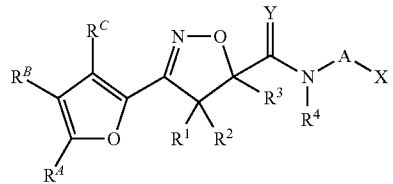

| No. | R¹ | R² | R³ | R⁴ | R^A | R^B | R^C | Y | A—X |
|---|---|---|---|---|---|---|---|---|---|
| 15.1 | H | H | Me | H | H | H | H | O | A.13 |
| 15.2 | H | H | Me | H | Cl | H | H | O | A.13 |
| 15.3 | H | H | Me | H | H | H | H | O | A.25 |
| 15.4 | H | H | Me | H | Cl | H | H | O | A.25 |
| 15.5 | H | H | Me | H | H | H | H | O | A.35 |
| 15.6 | H | H | Me | H | Cl | H | H | O | A.35 |
| 15.7 | H | H | Me | H | H | H | H | O | A.59 |
| 15.8 | H | H | Me | H | Cl | H | H | O | A.59 |
| 15.9 | H | H | Me | H | H | H | H | O | A.64 |
| 15.10 | H | H | Me | H | Cl | H | H | O | A.64 |
| 15.11 | H | H | Me | H | H | H | H | O | A.103 |
| 15.12 | H | H | Me | H | Cl | H | H | O | A.103 |
| 15.13 | H | H | Me | H | H | H | H | O | A.143 |
| 15.14 | H | H | Me | H | Cl | H | H | O | A.143 |
| 15.15 | H | H | Me | H | H | H | H | O | A.220 |
| 15.16 | H | H | Me | H | Cl | H | H | O | A.220 |

TABLE 15-continued

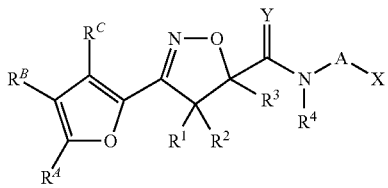

| No. | R¹ | R² | R³ | R⁴ | R^A | R^B | R^C | Y | A—X |
|---|---|---|---|---|---|---|---|---|---|
| 15.17 | H | H | Et | H | Cl | H | H | O | A.220 |
| 15.18 | H | H | OMe | H | Cl | H | H | O | A.220 |
| 15.19 | H | H | Me | H | H | H | H | S | A.64 |
| 15.20 | H | H | Me | H | Cl | H | H | S | A.64 |

TABLE 16

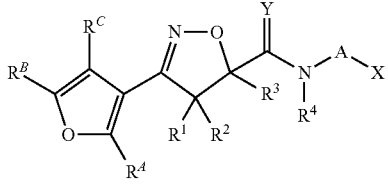

| No. | R¹ | R² | R³ | R⁴ | R^A | R^B | R^C | Y | A—X |
|---|---|---|---|---|---|---|---|---|---|
| 16.1 | H | H | Me | H | H | H | H | O | A.13 |
| 16.2 | H | H | Me | H | H | Cl | H | O | A.13 |
| 16.3 | H | H | Me | H | H | Br | H | O | A.13 |
| 16.4 | H | H | Me | H | H | H | H | O | A.35 |
| 16.5 | H | H | Me | H | H | Cl | H | O | A.35 |
| 16.6 | H | H | Me | H | H | Br | H | O | A.35 |
| 16.7 | H | H | Me | H | H | H | H | O | A.64 |
| 16.8 | H | H | Me | H | H | Cl | H | O | A.64 |
| 16.9 | H | H | Me | H | H | Br | H | O | A.64 |
| 16.10 | H | H | Me | H | H | H | H | O | A.103 |
| 16.11 | H | H | Me | H | H | Cl | H | O | A.103 |
| 16.12 | H | H | Me | H | H | Br | H | O | A.103 |
| 16.13 | H | H | Me | H | H | H | H | O | A.143 |
| 16.14 | H | H | Me | H | H | Cl | H | O | A.143 |
| 16.15 | H | H | Me | H | H | Br | H | O | A.143 |
| 16.16 | H | H | Me | H | H | H | H | O | A.220 |
| 16.17 | H | H | Me | H | H | Cl | H | O | A.220 |
| 16.18 | H | H | Me | H | H | Br | H | O | A.220 |
| 16.19 | H | H | Me | H | H | H | H | S | A.64 |
| 16.20 | H | H | Me | H | H | H | H | S | A.220 |

TABLE 17

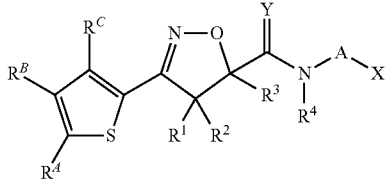

| No. | R¹ | R² | R³ | R⁴ | R^A | R^B | R^C | Y | A—X |
|---|---|---|---|---|---|---|---|---|---|
| 17.1 | H | H | Me | H | H | H | H | O | A.13 |
| 17.2 | H | H | Me | H | Cl | H | H | O | A.13 |
| 17.3 | H | H | Me | H | H | Br | H | O | A.13 |
| 17.4 | H | H | Me | H | H | H | H | O | A.59 |
| 17.5 | H | H | Me | H | Cl | H | H | O | A.59 |
| 17.6 | H | H | Me | H | H | Br | H | O | A.59 |
| 17.7 | H | H | Me | H | H | H | H | O | A.64 |
| 17.8 | H | H | Me | H | Cl | H | H | O | A.64 |
| 17.9 | H | H | Me | H | H | Br | H | O | A.64 |
| 17.10 | H | H | Me | H | H | H | H | O | A.103 |

TABLE 17-continued

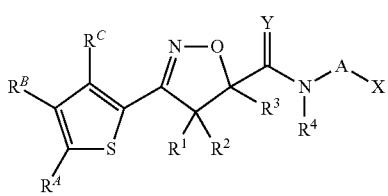

| No. | R¹ | R² | R³ | R⁴ | R^A | R^B | R^C | Y | A—X |
|---|---|---|---|---|---|---|---|---|---|
| 17.11 | H | H | Me | H | Cl | H | H | O | A.103 |
| 17.12 | H | H | Me | H | H | Br | H | O | A.103 |
| 17.13 | H | H | Me | H | H | H | H | O | A.132 |
| 17.14 | H | H | Me | H | Cl | H | H | O | A.132 |
| 17.15 | H | H | Me | H | H | Br | H | O | A.132 |
| 17.16 | H | H | Me | H | H | H | H | O | A.220 |
| 17.17 | H | H | Me | H | Cl | H | H | O | A.220 |
| 17.18 | H | H | Me | H | H | Br | H | O | A.220 |
| 17.19 | H | H | Me | H | H | H | H | S | A.64 |
| 17.20 | H | H | Me | H | H | H | H | S | A.220 |

TABLE 18

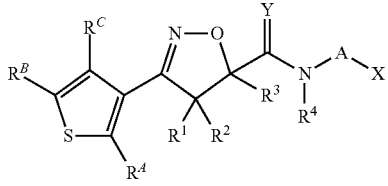

| No. | R¹ | R² | R³ | R⁴ | R^A | R^B | R^C | Y | A—X |
|---|---|---|---|---|---|---|---|---|---|
| 18.1 | H | H | Me | H | H | H | H | O | A.25 |
| 18.2 | H | H | Me | H | H | Cl | H | O | A.25 |
| 18.3 | H | H | Me | H | H | Br | H | O | A.25 |
| 18.4 | H | H | Me | H | H | H | H | O | A.35 |
| 18.5 | H | H | Me | H | H | Cl | H | O | A.35 |
| 18.6 | H | H | Me | H | H | Br | H | O | A.35 |
| 18.7 | H | H | Me | H | H | H | H | O | A.64 |
| 18.8 | H | H | Me | H | Cl | H | H | O | A.64 |
| 18.9 | H | H | Me | H | Br | H | H | O | A.64 |
| 18.10 | H | H | Me | H | H | Cl | H | O | A.64 |
| 18.11 | H | H | Me | H | H | Br | H | O | A.64 |
| 18.12 | H | H | Me | H | Br | Br | H | O | A.64 |
| 18.13 | H | H | Me | H | H | Cl | H | O | A.103 |
| 18.14 | H | H | Me | H | H | Br | H | O | A.103 |
| 18.15 | H | H | Me | H | H | H | H | O | A.103 |
| 18.16 | H | H | Me | H | Cl | H | H | O | A.112 |
| 18.17 | H | H | Me | H | H | Cl | H | O | A.112 |
| 18.18 | H | H | Me | H | H | Br | H | O | A.112 |
| 18.19 | H | H | Me | H | Br | Br | H | O | A.112 |
| 18.20 | H | H | Me | H | H | H | H | O | A.143 |
| 18.21 | H | H | Me | H | H | Cl | H | O | A.143 |
| 18.22 | H | H | Me | H | Br | H | H | O | A.143 |
| 18.23 | H | H | Me | H | H | Cl | H | O | A.143 |
| 18.24 | H | H | Me | H | H | Br | H | O | A.143 |
| 18.25 | H | H | Me | H | Br | Br | H | O | A.143 |
| 18.26 | H | H | Me | H | H | Cl | H | O | A.220 |
| 18.27 | H | H | Me | H | H | Br | H | O | A.220 |
| 18.28 | H | H | Me | H | Cl | H | H | O | A.220 |
| 18.29 | H | H | Me | H | Br | Br | H | O | A.220 |
| 18.30 | H | H | Me | H | H | H | H | O | A.220 |
| 18.31 | H | H | OMe | H | H | Br | H | O | A.220 |
| 18.32 | H | H | Vinyl | H | H | Br | H | O | A.143 |
| 18.33 | H | H | Vinyl | H | H | H | H | O | A.143 |
| 18.34 | H | H | Me | H | H | Br | H | S | A.64 |
| 18.35 | H | H | Me | H | H | Cl | H | S | A.64 |
| 18.36 | H | H | Me | H | H | H | H | S | A.64 |

TABLE 19

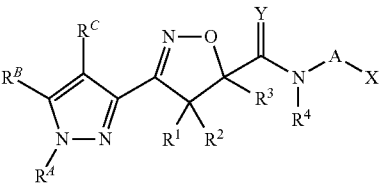

| No. | R¹ | R² | R³ | R⁴ | Rᴬ | Rᴮ | Rᶜ | Y | A—X |
|---|---|---|---|---|---|---|---|---|---|
| 19.1 | H | H | Me | H | Me | H | H | O | A.38 |
| 19.2 | H | H | Me | H | Me | Me | H | O | A.38 |
| 19.3 | H | H | Me | H | Et | H | H | O | A.38 |
| 19.4 | H | H | Me | H | Me | H | H | O | A.64 |
| 19.5 | H | H | Me | H | Me | Me | H | O | A.64 |
| 19.6 | H | H | Me | H | Et | H | H | O | A.64 |
| 19.7 | H | H | Me | H | Me | H | H | O | A.74 |
| 19.8 | H | H | Me | H | Me | Me | H | O | A.74 |
| 19.9 | H | H | Me | H | Et | H | H | O | A.74 |
| 19.10 | H | H | Me | H | Me | H | H | O | A.112 |
| 19.11 | H | H | Me | H | Me | Me | H | O | A.112 |
| 19.12 | H | H | Me | H | Et | H | H | O | A.112 |
| 19.13 | H | H | Me | H | Me | H | H | O | A.143 |
| 19.14 | H | H | Me | H | Me | Me | H | O | A.143 |
| 19.15 | H | H | Me | H | Et | H | H | O | A.143 |
| 19.16 | H | H | Me | H | Me | H | H | O | A.220 |
| 19.17 | H | H | Me | H | Me | Me | H | O | A.220 |
| 19.18 | H | H | Me | H | Et | H | H | O | A.220 |
| 19.19 | H | H | Me | H | Me | H | Cl | O | A.220 |
| 19.20 | H | H | Me | H | Me | H | H | S | A.64 |

TABLE 21

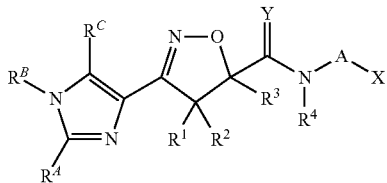

| No. | R¹ | R² | R³ | R⁴ | Rᴬ | Rᴮ | Rᶜ | Y | A—X |
|---|---|---|---|---|---|---|---|---|---|
| 21.1 | H | H | Me | H | H | Me | H | O | A.13 |
| 21.2 | H | H | Me | H | H | Et | H | O | A.13 |
| 21.3 | H | H | Me | H | H | Me | H | O | A.38 |
| 21.4 | H | H | Me | H | H | Et | H | O | A.38 |
| 21.5 | H | H | Me | H | H | Me | H | O | A.64 |
| 21.6 | H | H | Me | H | H | Et | H | O | A.64 |
| 21.7 | H | H | Me | H | H | Me | H | O | A.74 |
| 21.8 | H | H | Me | H | H | Et | H | O | A.74 |
| 21.9 | H | H | Me | H | H | Me | H | O | A.112 |
| 21.10 | H | H | Me | H | H | Et | H | O | A.112 |
| 21.11 | H | H | Me | H | H | Me | H | O | A.132 |
| 21.12 | H | H | Me | H | H | Et | H | O | A.132 |
| 21.13 | H | H | Me | H | H | Me | H | O | A.143 |
| 21.14 | H | H | Me | H | H | Et | H | O | A.143 |
| 21.15 | H | H | Me | H | H | Me | H | O | A.220 |
| 21.16 | H | H | Me | H | H | Et | H | O | A.220 |
| 21.17 | H | H | Me | H | Me | Me | H | O | A.220 |
| 21.18 | H | H | Me | H | Cl | Et | H | O | A.220 |
| 21.19 | H | H | Me | H | H | Me | H | S | A.13 |
| 21.20 | H | H | Me | H | H | Et | H | S | A.64 |

TABLE 20

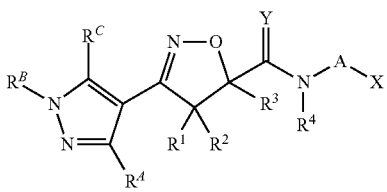

| No. | R¹ | R² | R³ | R⁴ | Rᴬ | Rᴮ | Rᶜ | Y | A—X |
|---|---|---|---|---|---|---|---|---|---|
| 20.1 | H | H | Me | H | H | Me | H | O | A.13 |
| 20.2 | H | H | Me | H | H | Et | H | O | A.13 |
| 20.3 | H | H | Me | H | H | Me | Cl | O | A.13 |
| 20.4 | H | H | Me | H | H | Me | H | O | A.64 |
| 20.5 | H | H | Me | H | H | Et | H | O | A.64 |
| 20.6 | H | H | Me | H | Me | Et | H | O | A.64 |
| 20.7 | H | H | Me | H | H | Me | H | O | A.112 |
| 20.8 | H | H | Me | H | H | Et | H | O | A.112 |
| 20.9 | H | H | Me | H | Me | Et | H | O | A.112 |
| 20.10 | H | H | Me | H | H | Me | H | O | A.143 |
| 20.11 | H | H | Me | H | H | Et | H | O | A.143 |
| 20.12 | H | H | Me | H | Me | Et | H | O | A.143 |
| 20.13 | H | H | Me | H | H | Me | H | O | A.214 |
| 20.14 | H | H | Me | H | H | Et | H | O | A.214 |
| 20.15 | H | H | Me | H | H | Me | H | O | A.220 |
| 20.16 | H | H | Me | H | H | Et | H | O | A.220 |
| 20.17 | H | H | Me | H | Me | Et | H | O | A.220 |
| 20.18 | H | H | Me | H | H | Me | H | S | A.220 |
| 20.19 | H | H | Me | H | H | Et | H | S | A.220 |
| 20.20 | H | H | Me | H | Me | Et | H | S | A.220 |

TABLE 22

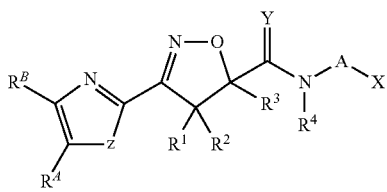

| No. | R¹ | R² | R³ | R⁴ | Rᴬ | Rᴮ | Y | Z | A—X |
|---|---|---|---|---|---|---|---|---|---|
| 22.1 | H | H | Me | H | H | H | O | O | A.64 |
| 22.2 | H | H | Me | H | H | Me | O | O | A.64 |
| 22.3 | H | H | Me | H | H | H | O | O | A.112 |
| 22.4 | H | H | Me | H | H | Me | O | O | A.112 |
| 22.5 | H | H | Me | H | H | H | O | O | A.143 |
| 22.6 | H | H | Me | H | H | Me | O | O | A.143 |
| 22.7 | H | H | Me | H | H | H | O | O | A.220 |
| 22.8 | H | H | Me | H | H | Me | O | O | A.220 |
| 22.9 | H | H | Me | H | H | H | S | O | A.64 |
| 22.10 | H | H | Me | H | H | Me | S | O | A.64 |
| 22.11 | H | H | Me | H | H | H | O | S | A.64 |
| 22.12 | H | H | Me | H | H | Me | O | S | A.64 |
| 22.13 | H | H | Me | H | H | H | O | S | A.112 |
| 22.14 | H | H | Me | H | H | Me | O | S | A.112 |
| 22.15 | H | H | Me | H | H | H | O | S | A.143 |
| 22.16 | H | H | Me | H | H | Me | O | S | A.143 |
| 22.17 | H | H | Me | H | H | H | O | S | A.220 |
| 22.18 | H | H | Me | H | H | Me | O | S | A.220 |
| 22.19 | H | H | Me | H | H | H | S | S | A.64 |
| 22.20 | H | H | Me | H | H | Me | S | S | A.64 |

TABLE 23

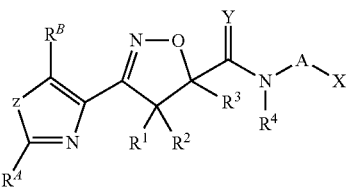

| No. | R¹ | R² | R³ | R⁴ | $R^A$ | $R^B$ | Y | Z | A—X |
|---|---|---|---|---|---|---|---|---|---|
| 23.1 | H | H | Me | H | Cl | H | O | O | A.64 |
| 23.2 | H | H | Me | H | Me | H | O | O | A.64 |
| 23.3 | H | H | Me | H | Cl | H | O | O | A.74 |
| 23.4 | H | H | Me | H | Me | H | O | O | A.74 |
| 23.5 | H | H | Me | H | Cl | H | O | O | A.112 |
| 23.6 | H | H | Me | H | Me | H | O | O | A.112 |
| 23.7 | H | H | Me | H | Cl | H | O | O | A.220 |
| 23.8 | H | H | Me | H | Me | H | O | O | A.220 |
| 23.9 | H | H | Me | H | Me | H | S | O | A.220 |
| 23.10 | H | H | OMe | H | Me | H | O | O | A.220 |
| 23.11 | H | H | Me | H | H | H | O | S | A.38 |
| 23.12 | H | H | Me | H | Me | H | O | S | A.38 |
| 23.13 | H | H | Me | H | H | H | O | S | A.74 |
| 23.14 | H | H | Me | H | Me | H | O | S | A.74 |
| 23.15 | H | H | Me | H | H | H | O | S | A.112 |
| 23.16 | H | H | Me | H | Me | H | O | S | A.112 |
| 23.17 | H | H | Me | H | H | H | O | S | A.143 |
| 23.18 | H | H | Me | H | Me | H | O | S | A.143 |
| 23.19 | H | H | Me | H | Cl | H | O | S | A.143 |
| 23.20 | H | H | Me | H | H | H | O | S | A.204 |
| 23.21 | H | H | Me | H | Me | H | O | S | A.204 |
| 23.22 | H | H | Me | H | Cl | H | O | S | A.204 |
| 23.23 | H | H | Me | H | H | H | S | S | A.204 |
| 23.24 | H | H | Me | H | Me | H | S | S | A.204 |

TABLE 24

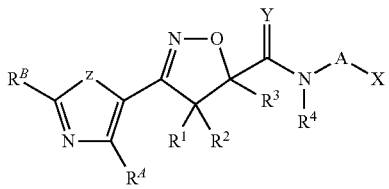

| No. | R¹ | R² | R³ | R⁴ | $R^A$ | $R^B$ | Y | Z | A—X |
|---|---|---|---|---|---|---|---|---|---|
| 24.1 | H | H | Me | H | H | H | O | O | A.64 |
| 24.2 | H | H | Me | H | H | Br | O | O | A.64 |
| 24.3 | H | H | Me | H | Cl | Br | O | O | A.64 |
| 24.4 | H | H | Me | H | H | Br | O | O | A.112 |
| 24.5 | H | H | Me | H | Cl | Br | O | O | A.112 |
| 24.6 | H | H | Me | H | H | Br | O | O | A.143 |
| 24.7 | H | H | Me | H | Cl | Br | O | O | A.143 |
| 24.8 | H | H | Me | H | H | Br | O | O | A.220 |
| 24.9 | H | H | Me | H | Cl | Br | O | O | A.220 |
| 24.10 | H | H | Me | H | H | H | S | O | A.64 |
| 24.11 | H | H | Me | H | H | H | O | S | A.64 |
| 24.12 | H | H | Me | H | H | Br | O | S | A.64 |
| 24.13 | H | H | Me | H | Cl | Br | O | S | A.64 |
| 24.14 | H | H | Me | H | H | Br | O | S | A.112 |
| 24.15 | H | H | Me | H | Cl | Br | O | S | A.112 |
| 24.16 | H | H | Me | H | H | Br | O | S | A.143 |
| 24.17 | H | H | Me | H | Cl | Br | O | S | A.143 |
| 24.18 | H | H | Me | H | H | Br | O | S | A.220 |
| 24.19 | H | H | Me | H | Cl | Br | O | S | A.220 |
| 24.20 | H | H | OMe | H | H | Br | O | S | A.64 |
| 24.21 | H | H | Et | H | H | Br | O | S | A.143 |
| 24.22 | H | H | Vinyl | H | H | Br | O | S | A.220 |
| 24.23 | H | H | Me | H | H | Br | S | S | A.64 |
| 24.24 | H | H | OMe | H | H | Br | S | S | A.220 |

TABLE 25

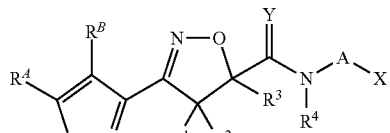

| No. | R¹ | R² | R³ | R⁴ | $R^A$ | $R^B$ | Y | Z | A—X |
|---|---|---|---|---|---|---|---|---|---|
| 25.1 | H | H | Me | H | H | H | O | O | A.64 |
| 25.2 | H | H | Me | H | H | H | O | O | A.74 |
| 25.3 | H | H | Me | H | H | H | O | O | A.112 |
| 25.4 | H | H | Me | H | H | H | O | O | A.220 |
| 25.5 | H | H | Me | H | H | H | O | S | A.64 |
| 25.6 | H | H | Me | H | H | H | O | S | A.74 |
| 25.7 | H | H | Me | H | H | H | O | S | A.112 |
| 25.8 | H | H | Me | H | H | H | O | S | A.220 |
| 25.9 | H | H | Me | H | H | H | S | S | A.64 |

TABLE 26

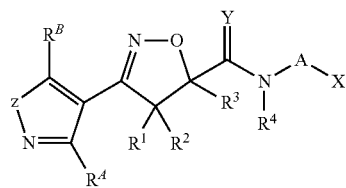

| No. | R¹ | R² | R³ | R⁴ | $R^A$ | $R^B$ | Y | Z | A—X |
|---|---|---|---|---|---|---|---|---|---|
| 26.1 | H | H | Me | H | H | H | O | O | A.64 |
| 26.2 | H | H | Me | H | H | H | O | O | A.74 |
| 26.3 | H | H | Me | H | H | H | O | O | A.112 |
| 26.4 | H | H | Me | H | H | H | O | O | A.220 |
| 26.5 | H | H | Me | H | H | H | O | S | A.64 |
| 26.6 | H | H | Me | H | H | H | O | S | A.74 |
| 26.7 | H | H | Me | H | H | H | O | S | A.112 |
| 26.8 | H | H | Me | H | H | H | O | S | A.220 |
| 26.9 | H | H | Me | H | H | H | S | S | A.64 |

TABLE 27

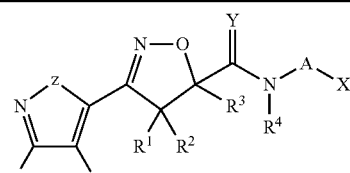

| No. | R¹ | R² | R³ | R⁴ | $R^A$ | $R^B$ | Y | Z | A—X |
|---|---|---|---|---|---|---|---|---|---|
| 27.1 | H | H | Me | H | H | H | O | O | A.64 |
| 27.2 | H | H | Me | H | H | H | O | O | A.74 |
| 27.3 | H | H | Me | H | H | H | O | O | A.112 |
| 27.4 | H | H | Me | H | H | H | O | O | A.220 |
| 27.5 | H | H | Me | H | H | H | O | S | A.64 |
| 27.6 | H | H | Me | H | H | H | O | S | A.74 |
| 27.7 | H | H | Me | H | H | H | O | S | A.112 |
| 27.8 | H | H | Me | H | H | H | O | S | A.220 |
| 27.9 | H | H | Me | H | H | H | O | S | A.64 |

TABLE 28

| No. | R¹ | R² | R³ | R⁴ | Rᴬ | Rᴮ | Y | A—X |
|---|---|---|---|---|---|---|---|---|
| 28.1 | H | H | Me | H | Me | H | O | A.64 |
| 28.2 | H | H | Me | H | Et | H | O | A.64 |
| 28.3 | H | H | Me | H | Me | H | O | A.112 |
| 28.4 | H | H | Me | H | Et | H | O | A.112 |
| 28.5 | H | H | Me | H | Me | H | O | A.143 |
| 28.6 | H | H | Me | H | Et | H | O | A.143 |
| 28.7 | H | H | Me | H | Me | H | O | A.220 |
| 28.8 | H | H | Me | H | Et | H | O | A.220 |
| 28.9 | H | H | Me | H | Me | H | O | A.64 |

TABLE 29

| No. | R¹ | R² | R³ | R⁴ | Rᴬ | Rᴮ | Rᶜ | Rᴰ | Y | A—X |
|---|---|---|---|---|---|---|---|---|---|---|
| 29.1 | H | H | Me | H | H | H | H | H | O | A.64 |
| 29.2 | H | H | Me | H | Me | H | H | H | O | A.64 |
| 29.3 | H | H | Me | H | Me | Me | H | H | O | A.64 |
| 29.4 | H | H | Me | H | H | H | H | H | O | A.112 |
| 29.5 | H | H | Me | H | Me | H | H | H | O | A.112 |
| 29.6 | H | H | Me | H | Me | Me | H | H | O | A.112 |
| 29.7 | H | H | Me | H | H | H | H | H | O | A.143 |
| 29.8 | H | H | Me | H | Me | H | H | H | O | A.143 |
| 29.9 | H | H | Me | H | Me | Me | H | H | O | A.143 |
| 29.10 | H | H | Me | H | Me | Me | H | H | O | A.217 |
| 29.11 | H | H | Me | H | H | H | H | H | O | A.220 |
| 29.12 | H | H | Me | H | Me | H | H | H | O | A.220 |
| 29.13 | H | H | Me | H | Me | Me | H | H | O | A.220 |
| 29.14 | H | H | Me | H | Me | Me | H | H | O | A.223 |
| 29.15 | H | H | Me | H | Me | Me | H | H | O | A.240 |
| 29.16 | H | H | OMe | H | Me | Me | H | H | O | A.64 |
| 29.17 | H | H | Vinyl | H | Me | Me | H | H | O | A.143 |
| 29.18 | H | H | Vinyl | H | Me | Me | H | H | O | A.220 |
| 29.19 | H | H | Me | H | Me | Me | H | H | S | A.220 |
| 29.20 | H | H | Vinyl | H | Me | Me | H | H | S | A.220 |

TABLE 30

| No. | R¹ | R² | R³ | R⁴ | Rᴬ | Rᴮ | Rᶜ | Rᴰ | Y | A—X |
|---|---|---|---|---|---|---|---|---|---|---|
| 30.1 | H | H | Me | H | H | H | H | H | O | A.64 |
| 30.2 | H | H | Me | H | Me | H | H | H | O | A.64 |
| 30.3 | H | H | Me | H | H | H | H | H | O | A.112 |
| 30.4 | H | H | Me | H | Me | H | H | H | O | A.112 |
| 30.5 | H | H | Me | H | H | H | H | H | O | A.143 |
| 30.6 | H | H | Me | H | Me | H | H | H | O | A.143 |
| 30.7 | H | H | Me | H | H | H | H | H | O | A.220 |
| 30.8 | H | H | Me | H | Me | H | H | H | O | A.220 |
| 30.9 | H | H | Me | H | H | H | H | S | S | A.220 |
| 30.10 | H | H | Me | H | Me | H | H | S | S | A.220 |

The abbreviations used mean:

| Ac | acetoxy | Bu | butyl | Et | ethyl | Me | methyl |
|---|---|---|---|---|---|---|---|
| Pr | propyl | Pen | pentyl | Hex | hexyl | Ph | phenyl |
| c | cyclo | s | secondary | i | iso | t | tertiary |
| THF | tetrahydrofuran | | | | | | |

The NMR data for the examples disclosed in tables 1.1 to 1.28 are noted in table B in the form of (δ values, number of hydrogen atoms, multiplet splitting). The δ value/signal intensity number pairs for different signal peaks are listed separated from one another by semicolons.

TABLE B

Analytical data

Example No. NMR (δ values): measured in CDCl₃, unless stated otherwise

| | |
|---|---|
| 1.2 | 1.19 (t, 3H); 1.72 (s, 3H); 3.30 (m, 2h); 3.41 (d, 1H); 4.00 (d, 1H); 6.73 (bm, 1H); 7.68 (d, 1H); 7.91 (t, 1H); 8.15 (d, 1H) |
| 1.4 | 1.13 (d, 3H); 1.18 (d, 3H); 1.70 (s, 3H); 3.41 (d, 1H); 3.97 (d, 1H); 4.04 (m, 1H); 6.59 (bd, 1H); 7.69 (d, 1H); 7.90 (t, 1H); 8.15 (d, 1H) |
| 1.5 | 1.13 (d, 3H); 1.18 (d, 3H); 1.70 (s, 3H); 3.38 (d, 1H); 3.92 (d, 1H); 4.03 (m, 1H); 6.58 (bd, 1H); 7.49 (d, 1H); 7.58 (t, 1H); 7.89 (d, 1H) |
| 1.7 | 1.74 (s, 3H); 2.54 (s, 3H); 3.43 (d, 1H); 3.80 (m, 1H); 3.96 (d, 1H); 4.03 (m, 1H); 7.15 (m, 2H); 7.61 (t, 1H); 7.70 (d, 1H) |
| 1.9 | 1.72 (s, 3H); 3.42 (d, 1H); 3.81 (m, 1H); 3.95 (d, 1H); 4.02 (m, 1H); 7.10 (bt, 1H); 7.37 (d, 1H); 7.71 (t, 1H); 7.88 (d, 1H) |
| 1.10 | 1.71 (s, 3H); 3.42 (d, 1H); 3.80 (m, 1H); 3.95 (d, 1H); 4.03 (m, 1H); 7.10 (bt, 1H); 7.51 (d, 1H); 7.60 (t, 1H); 7.90 (d, 1H) |
| 1.11 | 1.75 (s, 3H); 3.40 (d, 1H); 3.81 (m, 1H); 3.93 (d, 1H); 4.00 (m, 1H); 7.10 (bt, 1H); 7.33 (dd, 1H); 7.97 (d, 1H); 8.51 (d, 1H) |

TABLE B-continued

Analytical data

Example No. | NMR (δ values): measured in CDCl₃, unless stated otherwise
---|---
1.14 | 0.51 (m, 2H); 0.79 (m, 2H); 1.71 (s, 3H); 2.73 (m, 1H); 3.41 (d, 1H); 4.00 (d, 1H); 6.80 (bs, 1H); 7.69 (d, 1H); 7.90 (t, 1H); 8.12 (d, 1H)
1.16 | 0.50 (m, 2H); 0.79 (m, 2H); 1.70 (s, 3H); 2.73 (m, 1H); 3.38 (d, 1H); 3.95 (d, 1H); 6.79 (bs, 1H); 7.35 (d, 1H); 7.70 (t, 1H); 7.86 (d, 1H)
1.17 | [DMSO-d₆] 0.53 (m, 2H); 0.59 (m, 2H); 1.54 (s, 3H); 2.69 (m, 1H); 3.33 (d, 1H); 3.75 (d, 1H); 7.72 (d, 1H); 7.85 (t, 1H); 7.90 (d, 1H); 8.13 (bd, 1H)
1.20 | 1.70 (s, 3H); 2.53 (s, 3H); 2.54 (t, 2H); 3.39 (d, 1H); 3.55 (m, 2H); 3.68 (s, 3H); 3.95 (d, 1H); 7.17 (d, 1H); 7.24 (bm, 1H); 7.60 (t, 1H); 7.70 (d, 1H)
1.21 | 1.70 (s, 3H); 2.55 (t, 2H); 3.37 (d, 1H); 3.56 (m, 2H); 3.69 (s, 3H); 3.91 (s, 3H); 3.94 (d, 1H); 6.76 (d, 1H); 7.25 (bm, 1H); 7.51 (d, 1H); 7.60 (t, 1H)
1.22 | 1.71 (s, 3H); 2.55 (t, 2H); 3.38 (d, 1H); 3.54 (m, 2H); 3.70 (s, 3H); 3.92 (d, 1H); 7.20 (bm, 1H); 7.33 (d, 1H); 7.70 (t, 1H); 7.89 (d, 1H)
1.23 | 1.70 (s, 3H); 2.53 (t, 2H); 3.37 (d, 1H); 3.53 (m, 2H); 3.69 (s, 3H); 3.92 (d, 1H); 7.20 (bm, 1H); 7.49 (d, 1H); 7.58 (t, 1H); 7.90 (d, 1H)
1.25 | 1.70 (s, 3H); 2.55 (s, 3H); 2.60 (m, 2H); 3.38 (d, 1H); 3.55 (m, 2H); 3.95 (d, 1H); 7.15 (d, 1H); 7.49 (bt, 1H); 7.60 (t, 1H); 7.66 (d, 1H)
1.26 | [DMSO-d₆] 1.55 (s, 3H); 2.41 (t, 2H);3.30 (m, 2H); 3.36 (d, 1H); 3.70 (d, 1H); 7.61 (d, 1H); 7.88 (d, 1H); 7.95 (t, 1H); 8.11 (bt, 1H); 12.20 (bs, 1H)
1.27 | 1.70 (s, 3H); 2.61 (m, 2H); 3.38 (d, 1H); 3.56 (m, 2H); 3.93 (d, 1H); 7.25 (bm, 1H); 7.49 (d, 1H); 7.58 (t, 1H); 7.90 (d, 1H)
1.32 | 1.43 (t, 3H); 1.71 (s, 3H); 2.19 (s, 3H); 2.53 (s, 3H); 3.40 (d, 1H); 3.96 (d, 1H); 4.05 (q, 2H); 4.24 (m, 2H); 6.88 (bt, 1H); 7.16 (d, 1H); 7.24 (s, 1H); 7.60 (t, 1H); 7.77 (d, 1H)
1.33 | [DMSO-d₆] 1.26 (t, 3H); 1.59 (s, 3H); 2.05 (s, 3H); 3.40 (d, 1H); 3.79 (d, 1H); 3.95 (q, 2H); 4.07 (m, 2H); 7.40 (s, 1H); 7.99 (m, 1H); 8.19 (m, 2H); 8.38 (bt, 1H)
1.34 | 1.42 (t, 3H); 1.72 (s, 3H); 2.18 (s, 3H); 3.39 (d, 1H); 3.91 (s, 3H); 3.96 (d, 1H); 4.05 (q, 2H); 4.25 (m, 2H); 6.76 (d, 1H); 6.88 (bt, 1H); 7.22 (s, 1H); 7.49 (d, 1H); 7.59 (t, 1H)
1.35 | 1.45 (t, 3H); 1.72 (s, 3H); 2.19 (s, 3H); 3.39 (d, 1H); 3.95 (d, 1H); 4.06 (q, 2H); 4.25 (m, 2H); 6.81 (bt, 1H); 7.25 (s, 1H); 7.35 (d, 1H); 7.69 (t, 1H); 7.83 (d, 1H)
1.36 | 1.45 (t, 3H); 1.72 (s, 3H); 2.19 (s, 3H); 3.39 (d, 1H); 3.95 (d, 1H); 4.06 (q, 2H); 4.25 (m, 2H); 6.80 (bt, 1H); 7.25 (s, 1H); 7.49 (d, 1H); 7.58 (t, 1H); 7.88 (d, 1H)
1.37 | [DMSO-d₆] 1.26 (t, 3H); 1.57 (s, 3H); 2.04 (s, 3H); 3.36 (d, 1H); 3.76 (d, 1H); 3.95 (q, 2H); 4.06 (m, 2H); 7.40 (s, 1H); 7.63 (m, 1H); 7.91 (d, 1H); 8.31 (bt, 1H); 8.62 (d, 1H)
1.38 | 1.42 (t, 3H); 1.72 (s, 3H); 2.19 (s, 3H); 3.35 (d, 1H); 3.92 (d, 1H); 4.06 (q, 2H); 4.25 (m, 2H); 6.75 (bt, 1H); 7.26 (s, 1H); 7.38 (d, 1H); 7.85 (d, 1H)
2.1 | 1.76 (s, 3H); 3.26 (d, 1H); 3.59 (m, 1H); 3.73 (m, 1H); 3.83 (d, 1H); 5.85 (m, 1H); 7.06 (bm, 1H); 8.00 (m, 1H); 8.63 (d, 1H); 8.67 (d, 1H)
2.2 | 1.74 (s, 3H); 2.83 (d, 3H); 3.23 (d, 1H); 3.86 (d, 1H); 6.85 (bs, 1H); 7.36 (m, 1H); 7.98 (m, 1H); 8.66 (m, 1H); 8.82 (d, 1H)
2.4 | 1.18 (t, 3H); 1.74 (s, 3H); 3.21 (d, 1H); 3.30 (m, 2H); 3.85 (d, 1H); 6.77 (bs, 1H); 7.73 (m, 1H); 8.52 (m, 1H); 8.60 (m, 1H)
2.5 | 1.18 (t, 3H); 1.72 (s, 3H); 3.20 (d, 1H); 3.30 (m, 2H); 3.84 (d, 1H); 6.75 (bs, 1H); 8.14 (m, 1H); 8.71 (m, 2H)
2.7 | 1.13 (d, 3H); 1.19 (d, 3H); 1.72 (s, 3H); 3.21 (d, 1H); 3.83 (d, 1H); 4.02 (m, 1H); 6.60 (bd, 1H); 7.73 (m, 1H); 8.53 (m, 1H); 8.62 (m, 1H)
2.8 | 1.14 (d, 3H); 1.17 (d, 3H); 1.73 (s, 3H); 3.20 (d, 1H); 3.84 (d, 1H); 4.02 (m, 1H); 6.59 (bd, 1H); 8.00 (t, 1H); 8.62 (d, 1H); 8.68 (d, 1H)
2.9 | 1.13 (d, 3H); 1.19 (d, 3H); 1.72 (s, 3H); 3.20 (d, 1H); 3.82 (d, 1H); 4.02 (m, 1H); 6.60 (bd, 1H); 8.15 (m, 1H); 8.71 (m, 2H)
2.10 | 1.75 (s, 3H); 3.25 (d, 1H); 3.76 (m, 1H); 3.80 (d, 1H); 3.97 (s, 3H); 4.04 (m, 1H); 6.79 (d, 1H); 7.20 (bt, 1H); 7.96 (dd, 1H); 8.28 (d, 1H)
2.11 | 1.79 (s, 3H); 3.28 (d, 1H); 3.85 (m, 1H); 3.88 (d, 1H); 4.02 (m, 1H); 7.08 (bt, 1H); 8.25 (m, 1H); 8.92 (d, 1H); 9.00 (d, 1H)
2.13 | 1.78 (s, 3H); 3.28 (d, 1H); 3.81 (m, 1H); 3.84 (d, 1H); 4.03 (m, 1H); 7.11 (bt, 1H); 7.74 (m, 1H); 8.55 (m, 1H); 8.61 (m, 1H)
2.14 | 1.78 (s, 3H); 3.27 (d, 1H); 3.80 (m, 1H); 3.83 (d, 1H); 4.03 (m, 1H); 7.11 (bt, 1H); 7.98 (m, 1H); 8.64 (d, 1H); 8.69 (d, 1H)
2.15 | 1.78 (s, 3H); 3.26 (d, 1H); 3.80 (m, 1H); 3.82 (d, 1H); 4.02 (m, 1H); 7.11 (bt, 1H); 8.15 (m, 1H); 8.72 (d, 1H); 8.74 (d, 1H)
2.16 | 1.77 (s, 3H); 3.30 (d, 1H); 3.87 (d, 1H); 4.20 (m, 2H); 7.27 (bm, 1H); 7.75 (m, 1H); 8.57 (m, 1H); 8.61 (m, 1H)
2.17 | 1.78 (s, 3H); 3.28 (d, 1H); 3.82 (d, 1H); 4.21 (m, 2H); 7.23 (bm, 1H); 8.14 (m, 1H); 8.71 (d, 1H); 8.75 (d, 1H)
2.18 | 1.59 (m, 3H); 1.74 & 1.78 (2 × s, 3H); 3.26 & 3.28 (2 × d, 1H); 3.83 (d, 1H); 4.84 (m, 1H); 7.06 (bm, 1H); 8.00 (m, 1H); 8.64 (m, 1H); 8.68 (m, 1H)
2.19 | 1.75 (s, 3H); 3.24 (d, 1H); 3.81 (d, 1H); 4.53 (m, 2H); 4.92 (m, 2H); 5.03 (m, 1H); 7.33 (bd, 1H); 7.75 (m, 1H); 8.54 (m, 1H); 8.60 (m, 1H)
2.21 | 0.53 (m, 2H); 0.79 (m, 2H); 1.71 (s, 3H); 2.74 (m, 1H); 3.20 (d, 1H); 3.81 (d, 1H); 3.97 (s, 3H); 6.78 (d, 1H); 6.89 (bs, 1H); 7.95 (dd, 1H); 8.27 (d, 1H)
2.23 | 0.51 (m, 2H); 0.79 (m, 2H); 1.71 (s, 3H); 2.37 (s, 3H); 2.73 (m, 1H); 3.22 (d, 1H); 3.85 (d, 1H); 6.85 (bs, 1H); 7.79 (m, 1H); 8.49 (d, 1H); 8.62 (d, 1H)
2.25 | 0.51 (m, 2H); 0.80 (m, 2H); 1.71 (s, 3H); 2.37 (s, 3H); 2.74 (m, 1H); 3.22 (d, 1H); 3.85 (d, 1H); 6.80 (bs, 1H); 7.71 (m, 1H); 8.51 (m, 1H); 8.60 (m, 1H)

TABLE B-continued

Analytical data

Example No. | NMR (δ values): measured in CDCl₃, unless stated otherwise
---|---
2.27 | 0.51 (m, 2H); 0.79 (m, 2H); 1.71 (s, 3H); 2.72 (m, 1H); 3.20 (d, 1H); 3.84 (d, 1H); 6.79 (bs, 1H); 8.14 (m, 1H); 8.71 (m, 2H)
2.28 | 1.73 (s, 3H); 1.79 (m, 1H); 2.28 (m, 1H); 3.22 (2 × d, 1H); 3.67 (m, 1H); 3.81 (m, 3H); 3.95 (m, 1H); 4.47 (m, 1H); 6.92 (bs, 1H); 8.00 (m, 1H); 8.62 (m, 1H); 8.67 (m, 1H)
2.29 | 1.74 (s, 3H); 1.85 (m, 2H); 2.35 (t, 2H); 3.25 (1H, d); 3.32 (m, 2H); 3.67 (s, 3H); 3.86 (d. 1H); 6.96 (bt, 1H); 7.37 (m, 1H); 7.99 (m, 1H); 8.66 (m, 1H); 8.83 (d, 1H)
2.31 | 1.74 (s, 3H); 2.55 (t, 2H); 3.22 (d, 1H); 3.55 (m, 2H); 3.70 (s, 3H); 3.85 (d, 1H); 7.21 (bs, 1H); 8.25 (m, 1H); 8.90 (d, 1H); 9.00 (d, 1H)
2.32 | 1.72 (s, 3H); 2.55 (t, 2H); 3.22 (d, 1H); 3.65 (m, 2H); 3.69 (s, 3H); 3.83 (d, 1H); 7.24 (bs, 1H); 7.74 (m, 1H); 8.52 (m, 1H); 8.59 (m, 1H)
2.34 | 1.72 (s, 3H); 2.54 (t, 2H); 3.20 (d, 1H); 3.53 (m, 2H); 3.70 (s, 3H); 3.81 (d, 1H); 7.23 (bs, 1H); 8.15 (m, 1H); 8.71 (m, 2H)
2.37 | 1.70 (s, 3H); 2.55 (m, 2H); 3.20 (d, 1H); 3.55 (m, 2H); 3.85 (d, 1H); 7.40 (bs, 1H); 8.09 (m, 1H); 8.69 (m, 2H)
2.39 | 1.23 (m, 6H); 1.72 & 1.74 (2 × s; 3H); 2.47 & 2.53 (2 × d, 2H); 3.20 (d, 1H); 3.81 & 3.83 (2 × d, 1H); 4.07 & 4.15 (2 × q, 2H); 4.31 (m, 1H); 7.14 (bm, 1H); 8.00 (m, 1H); 8.61 (m, 1H); 8.68 (m, 1H)
2.40 | 1.80 (s, 3H); 3.26 (d, 1H); 3.87 (d, 1H); 3.90 (s, 3H); 4.42 (m, 2H); 6.56 (m, 1H); 6.72 (m, 1H); 7.19 (bm, 1H); 8.01 (m, 1H); 8.09 (d, 1H); 8.63 (m, 1H); 8.68 (m, 1H)
2.41 | 1.80 (s, 3H); 3.28 (d, 1H); 3.87 (d, 1H); 4.45 (m, 2H); 7.08 (m, 1H); 7.17 (s, 1H); 7.29 (bm, 1H); 8.01 (m, 1H); 8.32 (d, 1H); 8.64 (d, 1H); 8.69 (d, 1H)
2.42 | 1.80 (s, 3H); 3.28 (d, 1H); 3.87 (d, 1H); 4.49 (m, 2H); 6.78 (m, 1H); 7.03 (m, 1H); 7.33 (bt, 1H); 8.00 (m, 1H); 8.16 (d, 1H); 8.64 (d, 1H); 8.69 (d, 1H)
2.43 | 1.80 (s, 3H); 3.29 (d, 1H); 3.92 (d, 1H); 4.71 (m, 2H); 7.20 (m, 1H); 7.36 (m, 1H); 8.02 (m, 2H); 8.67 (m, 1H); 8.71 (m, 2H); 8.86 (m, 1H)
2.45 | 1.46 (t, 3H); 1.74 (s, 3H); 3.23 (d, 1H); 3.85 (d, 1H); 4.13 (q, 2H); 4.30 (m, 2H); 6.93 (bt, 1H); 7.34 (s, 1H); 7.42 (s, 1H); 7.98 (m, 1H); 8.62 (d, 1H); 8.67 (d, 1H)
2.46 | 1.47 (t, 3H); 1.75 (s, 3H); 2.28 (s, 3H); 3.29 (d, 1H); 3.38 (d, 1H); 4.18 (q, 2H); 4.27 (m, 2H); 6.96 (bt, 1H); 7.38 (s, 1H); 7.68 (m, 1H); 8.30 (m, 1H); 8.77 (m, 1H); 8.95 (s, 1H)
2.49 | 1.44 (t, 3H); 1.76 (s, 3H); 2.19 (s, 3H); 3.23 (d, 1H); 3.88 (d, 1H); 4.05 (q, 2H); 4.23 (m, 2H); 6.78 (bt, 1H); 7.27 (s, 1H); 8.24 (m, 1H); 8.91 (d, 1H); 9.00 (d, 1H)
2.50 | [DMSO-d₆] 1.25 (t, 3H); 1.56 (s, 3H); 2.04 (s, 3H); 3.40 (d, 1H); 3.87 (d, 1H); 3.87 (s, 3H); 3.95 (q, 2H); 4.07 (m, 2H); 7.40 (s, 1H); 7.58 (m, 1H); 8.31 (bt, 1H); 8.39 (d, 1H); 8.45 (d, 1H)
2.51 | 1.45 (t, 3H); 1.73 (s, 3H); 2.19 (s, 3H); 3.24 (d, 1H); 3.86 (d, 1H); 4.05 (q, 2H); 4.25 (m, 2H); 6.71 (bt, 1H); 7.27 (s, 1H); 7.72 (m, 1H); 8.53 (m, 1H); 8.60 (m, 1H)
2.53 | 1.44 (t, 3H); 1.74 (s, 3H); 2.20 (s, 3H); 3.23 (d, 1H); 3.85 (d, 1H); 4.05 (q, 2H); 4.25 (m, 2H); 6.81 (bt, 1H); 7.27 (s, 1H); 8.14 (m, 1H); 8.71 (m, 2H)
2.54 | 1.01 (t, 3H); 1.97 (m, 1H); 2.16 (m, 1H); 2.84 (d, 3H); 3.24 (d, 1H); 3.74 (d, 1H); 6.81 (bs, 1H); 7.39 (d, 1H); 7.97 (dd, 1H); 8.58 (d, 1H)
2.55 | 0.51 (m, 2H); 0.86 (m, 2H); 2.81 (m, 1H); 3.45 (d, 1H); 3.91 (d, 1H); 6.89 (bs, 1H); 7.46 (m, 1H); 8.16 (m, 1H); 8.68 (m, 1H); 8.85 (bs, 1H)
2.56 | 3.40 (s, 3H); 3.46 (d, 1H); 4.02 (d, 1H); 4.80 (m, 2H); 7.17 (m, 1H); 7.38 (m, 1H); 8.05 (m, 1H); 8.37 (m, 1H); 8.70 (m, 2H); 8.86 (m, 1H)
2.57 | 3.45 (s, 3H); 3.50 (d, 1H); 3.93 (d, 1H); 4.80 (m, 2H); 7.25 (m, 1H); 7.41 (m, 1H); 8.02 (bt, 1H); 8.11 (m, 1H); 8.68 (m, 1H); 8.74 (m, 2H); 8.86 (m, 1H)
2.61 | 1.25 (d, 3H); 1.30 (d, 3H); 1.88 s, 3H); 3.38 (d, 1H); 4.32 (d, 1H); 4.55 (m, 1H); 7.98 (d, 1H); 8.44 (bs, 1H); 8.62 (d, 1H); 8.70 (s, 1H)
3.1 | 1.14 (d, 3H); 1.20 (d, 3H); 1.73 (s, 3H); 3.17 (d, 1H); 3.80 (d, 1H); 4.04 (m, 1H); 6.57 (bd, 1H); 7.45 (d, 1H); 7.52 (s, 1H); 8.46 (d, 1H)
3.6 | 0.52 (m, "H); 0.79 (m, 2H); 1.72 (s, 3H); 2.73 (m, 1H); 3.20 (d, 1H); 3.82 (d, 1H); 6.81 (bs, 1H); 7.48 (d, 2H); 8.69 (d, 2H)
3.8 | 0.53 (m, 2H); 0.82 (m, 2H); 1.72 (s, 3H); 2.73 (m, 1H); 3.15 (d, 1H); 3.79 (d, 1H); 6.71 (bs, 1H); 7.46 (s, 2H)
3.18 | 1.47 (t, 3H); 1.74 (s, 3H); 2.19 (s, 3H); 3.19 (d, 1H); 3.81 (d, 1H); 4.07 (q, 2H); 4.25 (m, 1H); 6.78 (bt, 1H); 7.26 (s, 1H); 7.43 (d, 1H); 7.51 (s, 1H); 8.46 (d, 1H)
6.3 | [DMSO-d₆] 1.07 (m, 6H); 1.55 (s, 3H); 3.32 (d, 1H); 3.72 (d, 1H); 3.90 (m, 1H); 3.92 (s, 6H); 6.31 (s, 1H); 7.85 (bd, 1H)
6.4 | [DMSO-d₆] 1.60 (s, 3H); 3.42 (d, 1H); 3.73 (d, 1H); 3.89 (m, 2H); 3.92 (s, 6H); 6.31 (s, 1H); 8.82 (bt, 1H)
6.5 | 1.53 & 1.59 (2 × d, 3H); 1.74 & 1.78 (2 × s, 3H); 2.50 & 2.51 (2 × s, 6H); 3.43 & 3.48 (2 × d, 1H); 3.94 & 3.95 (2 × d, 1H); 4.82 (m, 1H); 7.04 (s, 1H); 7.11 (bd, 1H)
6.8 | 1.72 (s, 3H); 1.79 (m, 1H); 2.26 (m, 1H); 2.52 (s, 6H); 3.41 (2 × d, 1H); 3.61 (m, 1H); 3.88 (m, 4H); 4.45 (m, 1H); 6.99 (bs, 1H); 7.03 (s, 1H)
6.10 | [DMSO-d₆] 1.55 (s, 3H); 2.50 (m, 2H); 3.31 (m, 3H); 3.54 (m, 3H); 3.70 (d, 1H); 3.91 (s, 6H); 6.31 (s, 1H); 8.20 (bt, 1H)
6.14 | 1.78 (s, 3H); 2.51 (s, 6H); 3.46 (d, 1H); 3.97 (d, 1H); 4.47 (m, 2H); 6.78 (s, 1H); 7.04 (m, 2H); 7.36 (bt, 1H); 8.14 (d, 1H)
6.17 | [DMSO-d₆] 1.26 (t, 3H); 1.57 (s, 3H); 2.06 (s, 3H); 3.35 (d, 1H); 3.71 (d, 1H); 3.91 (s, 6H); 3.96 (q, 2H); 4.07 (m, 2H); 6.30 (s, 1H); 7.41 (s, 1H); 8.35 (bt, 1H)
6.19 | 1.89 & 1.90 (2 × s, 3H); 1.91 (m, 1H); 2.37 (m, 1H); 2.52 (s, 6H); 3.57 & 3.58 (2 × d, 1H); 3.61 (m, 1H); 3.80 (m, 2H); 3.96 (m, 2H); 4.32 & 4.36 (2 × d, 1H); 4.91 (m, 1H); 7.01 (s, 1H); 8.80 (bs, 1H)

TABLE B-continued

Analytical data

Example No. NMR (δ values): measured in CDCl₃, unless stated otherwise

| | |
|---|---|
| 7.5 | 0.52 (m, 2H); 0.80 (m, 2H); 1.71 (s, 3H); 2.58 (s, 3H); 2.73 (m, 1H); 3.32 (d. 1H); 3.90 (d, 1H); 6.70 (bs, 1H); 7.66 (s, 1H) |
| 7.6 | 0.51 (m, 2H); 0.79 (m, 2H); 1.70 (s, 3H); 2.49 (s, 3H); 2.73 (m, 1H); 3.32 (d. 1H); 3.90 (d, 1H); 3.99 (s, 3H); 6.74 (bs, 1H); 7.36 (s, 1H) |
| 7.7 | 1.72 (s, 3H); 1.80 (m, 1H); 2.29 (m, 1H); 2.58 (s, 3H); 3.34 6 3.35 (2 × d, 1H); 3.67 (m, 1H); 3.88 (m, 4H); 4.49 (m, 1H); 6.39 (bt, 1H); 7.68 (s, 1H) |
| 7.13 | 1.78 (s, 3H); 2.58 (s, 3H); 3.38 (d, 1H); 3.94 (d, 1H); 4.45 (m, 2H); 7.08 (d, 1H); 7.17 (s, 1H); 7.68 (s, 1H); 8.33 (d, 1H) |
| 7.16 | 1.78 (s, 3H); 2.51 (s, 3H); 3.39 (d, 1H); 3.94 (d, 1H); 4.01 (s, 3H); 4.49 (m, 2H); 6.78 (m, 1H); 7.04 (m, 1H); 7.22 (bm, 1H); 7.37 (s, 1H); 8.16 (d, 1H) |
| 7.17 | 1.47 (t, 3H); 1.73 (s, 3H); 2.57 (s, 3H); 3.33 (d. 1H); 3.90 (d, 1H); 4.11 (q, 2H); 4.30 (m, 2H); 6.82 (bs, 1H); 7.35 (s, 1H); 7.41 (s, 1H); 7.65 (s, 1H) |
| 7.20 | 1.44 (t, 3H); 1.72 (s, 3H); 2.19 (s, 3H); 2.49 (s, 3H); 3.34 (d, 1H); 3.92 (d, 1H); 4.00 (s, 3H); 4.05 (q, 2H); 4.25 (m, 2H); 6.77 (bt, 1H); 7.52 (s, 1H) |
| 8.5 | 0.54 (m, 2H), 0.79 (m, 2H); 1.74 (s, 3H); 2.74 (m, 1H); 3.22 (d, 1H); 3.88 (d, 1H); 6.81 (bs, 1H); 8.98 (s, 2H); 9.25 (s, 1H) |
| 8.9 | [DMSO-d₆] 1.57 (s, 3H); 2.50 (m, 2H); 3.31 (m, 2H); 3.42 (d, 1H); 3.54 (s, 3H); 3.79 (d, 1H); 8.18 (bt, 1H); 9.08 (s, 2H); 9.26 (s, 1H) |
| 8.17 | 1.44 (t, 3H); 1.75 (s, 3H); 2.20 (s, 3H); 3.23 (d, 1H); 3.88 (d, 1H); 4.05 (q, 2H); 4.25 (m, 2H); 6.81 (bm, 1H); 7.26 (s, 1H); 8.96 (s, 2H); 9.25 (s, 1H) |
| 9.1 | 1.57 & 1.62 (2 × d, 3H); 1.73 & 1.77 (2 × s, 3H); 2.57 & 2.58 (2 × s, 3H); 3.39 & 3.43 (2 × d, 1H); 3.95 & 3.96 (2 × d, 1H); 4.85 (m, 1H); 7.08 (bd, 1H); 8.46 & 8.47 (2 × s, 1H); 8.98 & 9.00 (2 × s, 1H) |
| 9.2 | 1.58 & 1.62 (2 × d, 3H); 1.74 & 1.77 (2 × s, 3H); 3.38 & 3.42 (2 × d, 1H); 3.94 & 3.95 (2 × d, 1H); 4.85 (m, 1H);7.02 (bd, 1H); 8.60 & 8.61 (2 × s, 1H); 9.10 & 9.12 (2 × s, 1H) |
| 9.3 | 0.52 (m, 2H), 0.79 (m, 2H); 1.72 (s, 3H); 2.57 (s, 3H); 2.73 (m, 1H); 3.34 (d, 1H); 3.95 (d, 1H); 6.81 (bs, 1H); 8.44 (s, 1H); 8.96 (s, 1H) |
| 9.4 | 0.53 (m, 2H), 0.80 (m, 2H); 1.72 (s, 3H); 2.73 (m, 1H); 3.33 (d, 1H); 3.94 (d, 1H); 6.75 (bs, 1H); 8.58 (s, 1H); 9.08 (s, 1H) |
| 9.11 | 1.80 (s, 3H); 2.58 (s, 3H); 3.42 (d, 1H); 3.99 (d, 1H); 4.45 (m, 2H); 7.08 (dd, 1H); 7.17 (d, 1H); 7.30 (bt, 1H); 8.32 (d, 1H); 8.46 (s, 1H); 8.99 (s, 1H) |
| 9.12 | 1.80 (s, 3H); 3.40 (d, 1H); 3.98 (d, 1H); 4.46 (m, 2H); 7.08 (dd, 1H); 7.17 (d, 1H); 7.24 (bt, 1H); 8.33 (d, 1H); 8.61 (s, 1H); 9.11 (s, 1H) |
| 9.14 | 1.80 (s, 3H); 3.40 (d, 1H); 3.98 (d, 1H); 4.48 (m, 2H); 6.79 (m, 1H); 7.05 (m, 1H); 7.24 (bs, 1H); 8.17 (m, 1H); 8.61 (s, 1H); 9.11 (s, 1H) |
| 9.16 | 1.47 (t, 3H); 1.74 (s, 3H); 3.35 (d, 1H); 3.94 (d, 1H); 4.13 (q, 2H); 4.30 (m, 2H); 6.90 (bt, 1H); 7.35 (s, 1H); 7.41 (s, 1H); 8.58 (s, 1H); 9.08 (s, 1H) |
| 9.18 | 1.44 (t, 3H); 1.74 (s, 3H); 2.20 (s, 3H); 3.35 (d, 1H); 3.95 (d, 1H); 4.06 (q, 2H); 4.26 (m, 2H); 6.78 (bm, 1H); 8.59 (s, 1H); 9.08 (s, 1H) |
| 9.20 | 1.49 (t, 3H); 1.91 (s, 3H); 3.53 (d, 1H); 4.16 (q, 2H); 4.36 (d, 1H); 4.64 (m, 2H); 7.45 (s, 1H); 7.49 (s, 1H); 8.58 (s, 1H); 9.06 (s, 1H) |
| 11.2 | 0.54 (m, 2H); 0.81 (m, 2H); 1.74 (s, 3H); 2.73 (m, 1H); 2.89 (s, 3H); 3.31 (d, 1H); 3.94 (d, 1H); 6.70 (bs, 1H); 9.60 (s, 1H) |
| 11.4 | 1.75 (s, 3H); 1.80 (m, 1H); 2.89 (s, 3H); 3.32 & 3.33 (2 × d, 1H); 3.66 (m, 1H); 3.87 (m, 4H); 4.48 (m, 1H); 6.82 (bm, 1H); 9.62 (s, 1H) |
| 11.6 | 1.24 (m, 6H); 1.73 & 1.74 (2 × s; 3H); 2.47 (m, 1H); 2.53 (m, 1H); 2.88 (s, 3H); 3.30 (d, 1H); 3.90 & 3.91 (2 × d, 1H); 4.08 & 4.17 (2 × q, 2H); 4.31 (m, 1H); 7.10 (bm, 1H); 8.62 (s, 1H) |
| 11.10 | 1.81 (s, 3H); 2.90 (s, 3H); 3.38 (d, 1H); 3.97 (d, 1H); 4.50 (m, 2H); 6.79 (m, 1H); 7.07 (m, 1H); 7.19 (bt, 1H); 8.17 (d, 1H); 9.63 (s, 1H) |
| 11.12 | 1.47 (t, 3H); 1.76 (S, 3H); 2.89 (s, 3H); 3.33 (d, 1H); 3.94 (d, 1H); 4.13 (q, 2H); 4.31 (m, 2H); 6.82 (bt, 1H); 7.35 (s, 1H); 7.42 (s, 1H); 9.60 (s, 1H) |
| 11.14 | 1.43 (t, 3H); 1.76 (S, 3H); 2.20 (s, 3H); 2.89 (s, 3H); 3.33 (d, 1H); 3.94 (d, 1H); 4.08 (q, 2H); 4.25 (m, 2H); 6.70 (bt, 1H); 7.25 (s, 1H); 9.60 (s, 1H) |
| 15.1 | 1.13 (d, 3H); 1.19 (d, 3H); 1.69 (s, 3H); 3.18 (d, 1H); 3.75 (d, 1H); 4.01 (m, 1H); 6.50 (m, 1H); 6.67 (bd, 1H); 6.70 (d, 1H); 7.52 (d, 1H) |
| 15.2 | [DMSO-d₆] 1.04 (d, 3H); 1.06 (d, 3H); 1.50 (s, 3H); 3.22 (d, 1H); 3.64 (d, 1H); 3.88 (m, 1H); 6.70 (d, 1H); 7.05 (d, 1H); 7.80 (bd, 1H) |
| 15.3 | 1.71 (s, 3H); 3.25 (d, 1H); 3.74 (m, 1H); 3.75 (d, 1H); 4.04 (m, 1H); 6.49 (m, 1H); 6.73 (d, 1H); 7.19 (bt, 1H); 7.53 (d, 1H) |
| 15.5 | 1.74 (s, 3H); 3.26 (d, 1H); 3.77 (d, 1H); 4.19 (m, 2H); 6.50 (m, 1H); 6.73 (d, 1H); 7.38 (bt, 1H); 7.56 (d, 1H) |
| 15.9 | 0.51 (m, 2H); 0.78 (m, 2H); 1.69 (s, 3H); 2.72 (m, 1H); 3.18 (d, 1H); 3.77 (d, 1H); 6.48 (m, 1H); 6.69 (d, 1H); 6.85 (bs, 1H); 7.51 (d, 1H) |
| 15.15 | 1.40 (t, 3H); 1.70 (s, 3H); 2.19 (s, 3H); 3.20 (d, 1H); 3.79 (d, 1H); 4.04 (q, 2H); 4.23 (m, 2H); 6.49 (m, 1H); 6.70 (d, 1H); 6.89 (bs, 1H); 7.24 (s, 1H); 7.52 (d, 1H) |
| 15.16 | [DMSO-d₆] 1.25 (t, 3H); 1.52 (s, 3H); 2.05 (s, 3H); 3.25 (d, 1H); 3.63 (d, 1H); 3.96 (q, 2H); 4.04 (m, 2H); 6.69 (d, 1H); 7.04 (d, 1H); 7.38 (s, 1H); 8.29 (bt, 1H) |
| 16.1 | 1.12 (d, 3H); 1.19 (d, 3H); 1.69 (s, 3H); 3.10 (d, 1H); 3.65 (d, 1H); 4.01 (m, 1H); 6.67 (bd, 1H); 6.72 (d, 1H); 7.46 (d, 1H); 7.61 (s, 1H) |
| 16.4 | 1.72 (s, 3H); 3.19 (d, 1H); 3.67 (d, 1H); 4.19 (m, 2H); 6.71 (d, 1H); 7.29 (bm, 1H); 7.47 (m, 1H); 7.62 (s, 1H) |
| 16.7 | 0.52 (m, 2H), 0.77 (m, 2H); 1.68 (s, 3H); 2.72 (m, 1H); 3.20 (d, 1H); 3.67 (d, 1H); 6.50 (d, 1H); 6.38 (bs, 1H); 6.46 (m, 1H); 7.62 (s, 1H) |

TABLE B-continued

Analytical data

Example No. NMR (δ values): measured in CDCl$_3$, unless stated otherwise

| | |
|---|---|
| 16.10 | 1.69 (s, 3H); 2.53 (t, 2H); 3.10 (d, 1H); 3.54 (m, 2H); 3.63 (d, 1H); 3.69 (s, 3H); 6.72 (d, 1H); 7.24 (bm, 1H); 7.46 (d, 1H); 7.61 (s, 1H) |
| 16.16 | 1.42 (t, 3H); 1.70 (s, 3H); 2.19 (s, 3H); 3.13 (d, 1H); 3.68 (d, 1H); 4.04 (q, 2H); 4.23 (m, 2H); 6.71 (d, 1H); 6.89 (bm, 1H); 7.23 (s, 1H); 7.45 (m, 1H); 7.52 (s, 1H) |
| 17.2 | 1.14 (d, 3H); 1.19 (d, 3H); 1.69 (s, 3H); 3.16 (d, 1H); 3.76 (d, 1H); 4.01 (m, 1H); 6.63 (bd, 1H); 6.89 (d, 1H); 6.94 (d, 1H) |
| 17.4 | 1.72 (s, 3H); 3.27 (d, 1H); 3.80 (d, 1H); 4.52 (m, 2H); 4.89 (m, 2H); 5.01 (m, 1H); 7.05 (m, 1H); 7.20 (d, 1H); 7.38 (bm, 1H); 7.44 (d, 1H) |
| 17.9 | 0.52 (m, 2H); 0.78 (m, 2H); 1.69 (s, 3H); 2.73 (m, 1H); 3.19 (d, 1H); 3.79 (d, 1H); 6.81 (bs, 1H); 7.09 (s, 1H); 7.29 (s, 1H) |
| 17.16 | [DMSO-d$_6$] 1.26 (t, 3H); 1.53 (s, 3H); 2.05 (s, 3H); 3.37 (d, 1H); 3.75 (d, 1H); 3.95 (q, 2H); 4.05 (m, 2H); 7.15 (m, 1H); 7.42 (d, 1H); 7.70 (d, 1H); 8.29 (bt, 1H) |
| 17.17 | 1.42 (t, 3H); 1.70 (s, 3H); 2.18 (s, 3H); 3.19 (d, 1H); 3.79 (d, 1H); 4.05 (q, 2H); 4.24 (m, 2H); 6.85 (bm, 1H); 6.89 (d, 1H); 6.95 (d, 1H); 7.23 (s, 1H) |
| 17.18 | 1.41 (t, 3H); 1.70 (s, 3H); 2.19 (s, 3H); 3.20 (d, 1H); 3.80 (d, 1H); 4.06 (q, 2H); 4.24 (m, 2H); 6.84 (bm, 1H); 7.10 (s, 1H); 7.24 (s, 1H); 7.29 (s, 1H) |
| 18.11 | 0.51 (m, 2H); 0.78 (m, 2H); 1.68 (s, 3H); 2.72 (m, 1H); 3.14 (d, 1H); 3.73 (d, 1H); 6.85 (bs, 1H); 7.31 (s, 1H); 7.41 (s, 1H) |
| 18.12 | 0.52 (m, 2H); 0.79 (m, 2H); 1.68 (s, 3H); 2.73 (m, 1H); 3.35 (d, 1H); 3.98 (d, 1H); 6.80 (bs, 1H); 7.29 (s, 1H) |
| 18.18 | 1.20 (t, 3H); 1.69 (d, 3H); 2.46 & 2.52 (2 × d, 2H); 3.13 & 3.14 (2 × d, 1H); 3.69 & 3.72 (2 × d, 1H); 4.07 & 4.14 (2 × q, 2H); 4.29 (m, 1H); 7.13 (bm, 1H); 7.31 (m, 1H); 7.42 (m, 1H) |
| 18.19 | 1.25 (m, 3H); 1.68 (d, 3H); 2.48 & 2.52 (2 × d, 2H); 3.32 & 3.37 (2 × d, 1H); 3.94 & 3.97 (2 × d, 1H); 4.12 & 4.15 (2 × q, 2H); 4.31 (m, 1H); 7.11 (bm, 1H); 7.27(s, 1H) |
| 18.21 | 1.77 (s, 3H); 3.42 (d, 1H);4.02 (d, 1H);4.45 (m, 2H); 7.08 (d, 1H); 7.14(d, 1H); 7.19 (bm, 1H); 7.25 (m, 2H); 8.31 (d, 1H) |
| 18.22 | 1.77 (s, 3H); 3.46 (d, 1H); 4.06 (d, 1H); 4.45 (m, 2H); 7.07 (m, 1H); 7.17 (m, 1H); 7.25 (m, 2H); 7.32 (bm, 1H); 8.31 (d, 1H) |
| 18.24 | 1.76 (s, 3H); 3.21 (d, 1H); 3.75 (d, 1H); 4.43 (m, 2H); 7.06 (m, 1H); 7.16 (m, 1H); 7.35 (m, 1H); 7.43 (m, 1H); 8.31 (m, 1H) |
| 18.25 | 1.76 (s, 3H); 3.41 (d, 1H); 4.01 (d, 1H); 4.45 (m, 2H); 7.07 (m, 1H); 7.17 (m, 1H); 7.25 (m, 2H); 8.33 (d, 1H) |
| 18.27 | 1.42 (t, 3H); 1.70 (s, 3H); 2.18 (s, 3H); 3.16 (d, 1H); 3.74 (d, 1H); 4.04 (q, 2H); 4.23 (m, 2H); 6.87 (bm, 1H); 7.23 (s, 1H); 7.32 (d, 1H); 7.40 (d, 1H) |
| 18.28 | 1.44 (t, 3H); 1.71 (s, 3H); 2.20 (s, 3H); 3.38 (d, 1H); 3.99 (d, 1H); 4.05 (q, 2H); 4.25 (m, 2H); 6.87 (bm, 1H); 7.11 (d, 1H); 7.26 (m, 2H) |
| 18.29 | 1.45 (t, 3H); 1.71 (s, 3H); 2.20 (s, 3H); 3.36 (d, 1H); 3.99 (d, 1H); 4.08 (q, 2H); 4.25 (m, 2H); 6.81 (bm, 1H); 7.25 (s, 1H); 7.30 (s, 1H) |
| 18.30 | 1.41 (t, 3H); 1.71 (s, 3H); 2.19 (s, 3H); 3.23 (d, 1H); 3.79 (d, 1H); 4.05 (q, 2H); 4.23 (m, 2H); 6.92 (bm, 1H); 7.25 (s, 1H); 7.38 (m, 1H); 7.44 (d, 1H);7.48 (d, 1H) |
| 19.19 | 1.43 (t, 3H); 1.71 (s, 3H); 2.19 (s, 3H); 3.31 (d, 1H); 3.89 (s + d, 4H); 4.05 (q, 2H); 4.23 (m, 2H); 6.91 (bt, 1H); 7.25 (s, 1H); 7.42 (s, 1H) |
| 20.1 | 1.11 (d, 3H); 1.18 (d, 3H); 1.78 (s, 3H); 3.12 (d, 1H); 3.69(d, 1H); 3.93 (s, 3H); 4.01 (m, 1H); 6.74 (bd, 1H); 7.62 (s, 1H); 7.72 (s, 1H) |
| 20.3 | 1.11 (d, 3H); 1.18 (d, 3H); 1.76 (s, 3H); 3.20 (d, 1H); 3.81 (d, 1H); 3.87 (s, 3H); 4.02 (m, 1H); 6.69 (bd, 1H); 7.74 (s, 1H) |
| 20.6 | 0.51 (m, 2H), 0.77 (m, 2H); 1.46 (t, 3H); 1.66 (s, 3H); 2.43 (s, 3H); 2.72 (m, 1H); 3.12 (d, 1H); 3.69 (d, 1H); 6.93 (bs, 1H); 7.44 (s, 1H) |
| 20.12 | 1.48 (t, 3H); 1.75 (s, 3H); 2.44 (s, 3H); 3.19 (d, 1H); 3.70 (d, 1H); 4.11 (q, 2H); 4.44 (m, 2H); 7.06 (d, 1H); 7.15 (s, 1H); 7.42 (bt, 1H); 7.46 (s, 1H); 8.30 (d, 1H) |
| 20.15 | 1.44 (m, 6H), 1.69 (s, 3H); 2.21 (s, 3H); 3.15 (d, 1H); 3.69 (d, 1H); 3.95 (s, 3H); 4.11 (q, 2H); 4.22 (m, 2H); 6.99 (bt, 1H); 7.29 (s, 1H); 7.52 (s, 1H); 7.70 (s, 2H) |
| 20.17 | 1.45 (m, 6H), 1.69 (s, 3H); 2.20 (s, 3H); 2.41 (s, 3H); 3.15 (d, 1H); 3.70 (d, 1H); 4.09 (m, 4H); 4.24 (m, 2H); 6.96 (bt, 1H); 7.23 (s, 1H); 7.44 (s, 1H) |
| 21.5 | 0.51 (m, 2H); 0.78 (m, 2H); 1.70 (s, 3H); 2.72 (m, 1H); 3.22 (d, 1H); 3.78 (d, 1H); 3.85 (s, 3H); 6.88 (bs, 1H); 7.28 (s, 1H); 8.19 (s, 1H) |
| 22.11 | [DMSO-d$_6$] 0.52 (m, 2H); 0.59 (m, 2H); 1.56 (s, 3H); 2.68 (m, 1H); 3.41 (d, 1H); 3.82 (d, 1H); 7.93 (d, 1H); 8.01 (d, 1H); 8.15 (bs, 1H) |
| 22.12 | 0.51 (m, 2H); 0.79 (m, 2H); 1.70 (s, 3H); 2.47 (s, 3H); 2.73 (m, 1H); 3.38 (d, 1H); 3.96 (d, 1H); 6.78 (bs, 1H); 6.98 (s, 1H) |
| 22.13 | 1.23 (t, 3H); 1.71 (d, 3H); 2.48 & 2.54 (2 × d, 2H); 3.40 & 3.41 (2 × d, 1H); 3.95 & 3.99 (2 × d, 1H); 4.09 & 4.16(2 × q, 2H); 4.31 (m, 1H); 7.11 (bm, 1H); 7.44 (d, 1H); 7.90 (d, 1H) |
| 22.17 | [DMSO-d$_6$] 1.27 (t, 3H); 1.57 (s, 3H); 2.05 (s, 3H); 3.44 (d, 1H); 3.78 (d, 1H); 3.95 (q, 2H); 4.06 (m, 2H); 7.40 (s, 1H); 7.93 (d, 1H); 8.01 (d, 1H); 8.37 (bt, 1H) |
| 23.2 | 0.50 (m, 2H); 0.77 (m, 2H); 1.69 (s, 3H); 2.50 (s, 3H); 2.71 (m, 1H); 3.15 (d, 1H); 3.71 (d, 1H); 6.85 (bs, 1H); 7.78 (s, 1H) |
| 23.8 | 1.44 (t, 3H); 1.71 (s, 3H); 2.18 (s, 3H); 2.49 (s, 3H); 3.18 (d, 1H); 3.72 (d, 1H); 4.05 (q, 2H); 4.22 (m, 2H); 6.88 (bt, 1H); 7.24 (s, 1H); 7.79 (s, 1H) |
| 23.12 | 1.55 & 1.61 (2 × d, 3H); 1.71 & 1.75 (2 × s, 3H); 2.74 & 2.75 (2 × s, 3H); 3.32 & 3.37 (2 × d, 1H); 3.83 & 3.84 (2 × d, 1H); 4.82 (m, 1H); 7.13 (bd, 1H); 7.49 & 7.51 (2 × s, 1H) |

TABLE B-continued

Analytical data

Example No. NMR (δ values): measured in CDCl₃, unless stated otherwise

| | |
|---|---|
| 23.14 | 1.71 (s, 3H); 1.79 (m, 1H); 2.28 (m, 1H); 2.75 (s, 3H); 3.29 (2 × d, 1H); 3.62 (m, 1H); 3.83 (m, 4H); 4.46 (m, 1H); 7.00 (bd, 1H); 7.46 & 7.47 (2 × s, 1H) |
| 23.16 | 1.22 (m, 6H); 1.69 & 1.70 (2 × s; 3H); 2.49 (m, 2H); 2.74 (s, 3H); 3.27 & 3.28 (2 × d, 1H); 3.81 & 3.84 (2 × d, 1H); 4.08 & 4.15 (2 × q, 2H); 4.30 (m, 1H); 7.10 & 7.15 (2 × bd, 1H); 7.45 & 7.46 (2 × s, 1H) |
| 23.18 | 1.78 (s, 3H); 2.75 (s, 3H); 3.35 (d, 1H); 3.87 (d, 1H); 4.43 (m, 2H); 7.07 (dd, 1H); 7.16 (d, 1H); 7.36 (bt, 1H); 7.50 (s, 1H); 8.30 (d, 1H) |
| 23.21 | 1.46 (t, 3H); 1.72 (s, 3H); 2.74 (s, 3H); 3.30 (d, 1H); 3.85 (d, 1H); 4.12 (q, 2H); 4.28 (m, 2H); 7.01 (bt, 1H); 7.33 (s, 1H); 7.40 (s, 1H); 7.45 (s, 1H) |
| 24.12 | 0.52 (m, 2H); 0.78 (m, 2H); 1.70 (s, 3H); 2.72 (m, 1H); 3.28 (d, 1H); 3.86 (d, 1H); 6.82 (bs, 1H); 7.61 (s, 1H) |
| 24.13 | 0.52 (m, 2H); 0.78 (m, 2H); 1.70 (s, 3H); 2.73 (m, 1H); 3.34 (d, 1H); 3.94 (d, 1H); 6.81 (bs, 1H) |
| 24.14 | 1.26 (m, 6H); 1.69 & 1.70 (2 × s, 3H); 2.50 (m, 2H); 3.27 & 3.28 (2 × d, 1H); 3.82 & 3.85 (2 × d, 1H); 4.11 (m, 2H); 4.31 (m, 1H); 7.12 (bm, 1H); 7.63 (s, 1H) |
| 24.15 | 1.27 (m, 6H); 1.69 & 1.70 (2 × s, 3H); 2.50 (m, 2H); 3.34 & 3.35 (2 × d, 1H); 3.89 & 3.92 (2 × d, 1H); 4.12 (m, 2H); 4.31 (m, 1H); 7.08 (bm, 1H) |
| 24.16 | 1.77 (s, 3H); 3.35 (d, 1H); 3.89 (d, 1H); 7.07 (dd, 1H); 7.16 (d, 1H); 7.30 (bt, 1H); 7.67 (s, 1H); 8.31 (d, 1H) |
| 24.18 | 1.44 (t, 3H); 1.72 (s, 3H); 2.19 (s, 3H); 3.30 (d, 1H); 3.86 (d, 1H); 4.05 (q, 2H); 4.24 (m, 2H); 6.84 (bt, 1H); 7.25 (s, 1H); 7.62 (s, 1H) |
| 24.19 | 1.44 (t, 3H); 1.72 (s, 3H); 2.20 (s, 3H); 3.36 (d, 1H); 3.95 (d, 1H); 4.05 (q, 2H); 4.24 (m, 2H); 6.83 (bt, 1H); 7.25 (s, 1H) |
| 29.13 | 1.45 (s, 6H); 1.46 (t, 3H); 1.68 (s, 3H); 2.20 (s, 3H); 2.97 (m, 2H); 3.18 (d, 1H); 3.74 (d, 1H); 4.07 (q, 2H); 4.25 (m, 2H); 6.71 (bt, 1H); 7.27 (s, 1H) |
| 30.5 | 1.70 (s, 3H); 3.00 (d, 1H); 3.45 (d, 1H); 4.01 (m, 4H) 4.44 (d, 2H); 5.63 (s, 1H); 7.08 (d, 1H); 7.19 (s, 1H); 7.28 (bm, 1H); 8.34 (d, 1H) |
| 30.8 | 1.31 (m, 3H); 1.46 (t, 3H); 1.65 & 1.66 (2 × s, 3H); 2.25 (s, 3H); 2.99 (m, 1H); 3.45 (m, 2H); 4.11 (m, 3H); 4.26 (m, 3H); 5.59, 5.60 & 5.72 (3 × s, 1H); 6.87 (bm, 1H); 7.29 (s, 1H) |

B. Formulation Examples

1. Dusting Products

A dusting product is obtained by mixing 10 parts by weight of a compound of the formula (I) and 90 parts by weight of talc as an inert substance and comminuting the mixture in a hammer mill.

2. Dispersible powder

A readily water-dispersible wettable powder is obtained by mixing 25 parts by weight of a compound of the formula (I), 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

3. Dispersion concentrate

A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

4. Emulsifiable concentrate

An emulsifiable concentrate is obtained from 15 parts by weight of a compound of the formula (I), 75 parts by weight of cyclohexanone as a solvent and 10 parts by weight of ethoxylated nonylphenol as an emulsifier.

5. Water-dispersible granules

Water-dispersible granules are obtained by mixing
75 parts by weight of a compound of the formula (I),
10 parts by weight of calcium lignosulfonate,
5 parts by weight of sodium laurylsulfate,
3 parts by weight of polyvinyl alcohol and
7 parts by weight of kaolin,
grinding the mixture in a pinned-disk mill, and granulating the powder in a fluidized bed by spray application of water as a granulating liquid.

Water-dispersible granules are also obtained by homogenizing and precomminuting, in a colloid mill,
25 parts by weight of a compound of the formula (I),
5 parts by weight of sodium 2,2'-dinaphthylmethane-6,6'-disulfonate,
2 parts by weight of sodium oleoylmethyltaurate,
1 part by weight of polyvinyl alcohol,
17 parts by weight of calcium carbonate and
50 parts by weight of water,
then grinding the mixture in a bead mill and atomizing and drying the suspension thus obtained in a spray tower by means of a one-phase nozzle.

C. Biological Examples

1. Pre-Emergence Herbicidal Action Against Harmful Plants

Seeds or rhizome pieces of mono- and dicotyledonous harmful plants are placed in sandy loam soil in pots having a diameter of 9 to 13 cm and covered with soil. The herbicides, formulated as emulsifiable concentrates or dusting products, are then applied to the surface of the covering soil in various dosages in the form of aqueous dispersions or suspensions or emulsions at an application rate equating to 300 to 800 l of water/ha. For further cultivation of the plants, the pots are then kept under optimal conditions in a greenhouse. After the test plants have been left to stand in the greenhouse for 3 to 4 weeks under optimal growth conditions, the activity of the inventive compounds is scored visually. For example, compound nos. 1.7, 1.38, 2.8, 2.9, 2.15, 2.16, 2.17, 2.27, 2.49, 2.53, 6.3, 6.17 and 17.18 at an application rate of 320 grams per hectare each show at least 80% efficacy against *Polygonum convolvulus* and *Veronica persica*. Compound nos. 1.33, 1.34, 1.36, 2.1, 2.8, 2.19, 2.26, 2.28, 2.41, 2.42, 2.45, 2.46, 2.49, 2.52, 3.8, 3.18, 15.16, 17.16 and 18.27 at an application rate of 320 grams per hectare each show at least 80% efficacy against *Alopecurus myosuroides* and *Lolium multiflorum*.

2. Post-Emergence Herbicidal Action Against Harmful Plants

Seeds of monocotyledonous and dicotyledonous harmful plants are laid out in sandy loam in cardboard pots, covered with soil and cultivated in a greenhouse under good growth conditions. Two to three weeks after sowing, the test plants are treated at the three-leaf stage. The inventive compounds, formulated as wettable powders or as emulsion concentrates, are sprayed onto the surface of the green parts of the plants at an application rate of water equating to 600 to 800 l/ha. After the test plants have been left to stand in the greenhouse for 3 to 4 weeks under optimal growth conditions, the activity of the inventive compounds is scored visually. For example, compound nos. 1.34, 1.38, 2.1, 2.18, 2.28, 2.29, 2.33, 2.41, 2.46, 2.49, 2.51, 2.52, 2.53, 6.17 and 18.27 at an application rate of 320 grams per hectare each show at least 80% efficacy against *Polygonum convolvulus* and *Veronica persica*. Compound nos. 2.39, 3.8, 18.11, 18.25, at an application rate of 320 grams per hectare each show at least 80% efficacy against *Pharbitis purpureum*.

The invention claimed is:

1. A 3-heteroarylisoxazoline-5-carboxamide and/or 3-heteroarylisoxazoline-5-thioamide of formula (I) and/or an N-oxide thereof

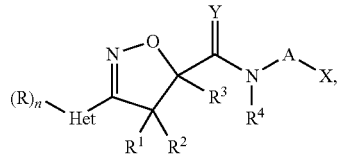

(I)

in which $R^1$ and $R^2$ are each independently selected from the group consisting of hydrogen, fluorine, chlorine, bromine, iodine, cyano, or $(C_1-C_4)$-alkyl substituted by m radicals from the group consisting of fluorine, chlorine, bromine, iodine and cyano;

$R^3$ is $(C_1-C_4)$-alkyl, $(C_3-C_4)$-cycloalkyl, $(C_2-C_3)$-alkenyl or $(C_2-C_3)$-alkynyl each substituted by m radicals from the group consisting of fluorine, chlorine, bromine, cyano, $(C_1-C_2)$-alkoxy, A is a bond or a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH=CH$, $C(CH_3)_2C\equiv C$, $CH(CF_3)CH_2$, $CH(CH_3)CH_2O$, $CH_2CH_2O$, $CH(cPr)CH_2O$, $CH(CH_2OCH_3)CH$ $(CH_2CH_2SCH_3)$, $CH(COOH)$, $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

$R^4$ is hydrogen or $(C_1-C_8)$-alkyl;

Y is oxygen or sulfur;

X is cyano, hydroxyl, $X^1$, or $(C_1-C_{12})$-alkyl, $(C_3-C_8)$-cycloalkyl, $(C_2-C_{12})$-alkenyl or $(C_2-C_{12})$-alkynyl each substituted by m radicals from the group consisting of fluorine, chlorine, cyano, hydroxyl, $OR^7$, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring which is substituted by s radicals from the group consisting of $R^6$, $R^{6a}$, $R^8$ and $R^9$ and is from the group consisting of

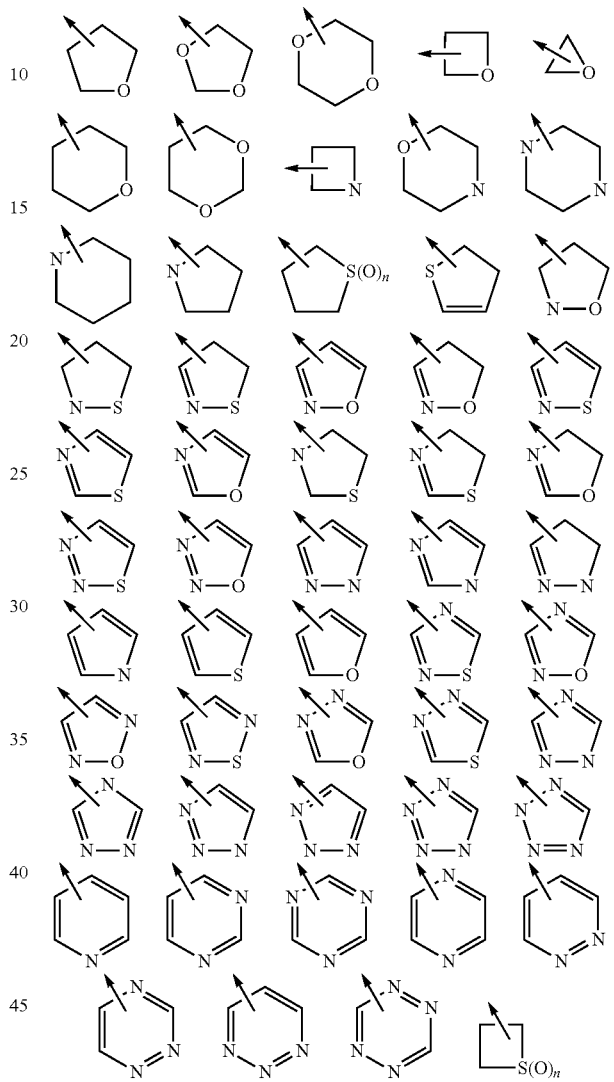

or $X^1$ is phenyl substituted by m radicals from the group consisting of $R^6$, $R^{6a}$, $R^8$ and $R^9$;

Het is pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,2,4-triazin-3-yl, 1,2,4-triazin-5-yl, 1,2,4-triazin-6-yl, 1,3,5-triazin-2-yl, pyrrol-3-yl, furan-2-yl, furan-3-yl, thiophen-2-yl, thiophen-3-yl, pyrazol-3-yl, pyrazol-4-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-4-yl, 2H-1,2,3-triazol-4-yl, 1H-1,2,4-triazol-3-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl or 2H-tetrazol-5-yl;

R is fluorine, chlorine, bromine, cyano, or $(C_1-C_6)$-alkyl each substituted by m radicals from the group consisting of fluorine and chlorine, or $(C_1-C_6)$-alkoxy substituted by m radicals from the group consisting of fluorine and chlorine;

$R^5$ is methyl or ethyl;

$R^6$ is hydrogen or $R^5$;

$R^{6a}$ is fluorine, chlorine, bromine, iodine, cyano, hydroxyl, $S(O)_nR^5$, or $(C_1-C_6)$-alkoxy, $(C_2-C_6)$-alkenyloxy or $(C_2-C_6)$-alkynyloxy each substituted by m radicals from the group consisting of fluorine, chlorine, bromine, cyano and $(C_1-C_2)$-alkoxy;

$R^7$ is hydrogen or $(C_1-C_6)$-alkyl substituted by m radicals from the group consisting of fluorine and chlorine;

$R^8$ is $R^7$, $R^9$ is $(C_1-C_3)$-alkoxy;

m is 0, 1, 2 or 3;

n is 0, 1 or 2;

s is 0, 1, 2, 3 or 4;

t is 0, 1 or 2.

2. A herbicidal composition comprising a herbicidally active content of at least one compound of the formula (I) and/or N-oxide thereof as claimed in claim 1.

3. The herbicidal composition as claimed in claim 2 in a mixture with one or more formulation auxiliaries.

4. The herbicidal composition as claimed in claim 2 which comprises at least one further pesticidally active substance from the group of insecticides, acaricides, herbicides, fungicides, safeners and growth regulators.

5. The herbicidal composition as claimed in claim 4, comprising a safener.

6. The herbicidal composition as claimed in claim 5, in which the safener is selected from the group consisting of mefenpyr-diethyl, cyprosulfamide, isoxadifen-ethyl, cloquintocet-mexyl, benoxacor and dichlormid.

7. The herbicidal composition as claimed in claim 4, comprising a further herbicide.

8. A method for controlling unwanted plants, comprising applying an effective amount of at least one compound of formula (I) and/or N-oxide thereof,

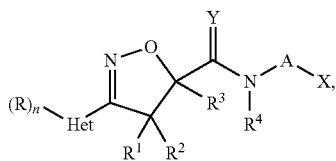

in which $R^1$ and $R^2$ are each independently selected from the group consisting of hydrogen, fluorine, chlorine, bromine, iodine, cyano, or $(C_1-C_4)$-alkyl or $(C_1-C_4)$-alkoxy each substituted by m radicals from the group consisting of fluorine, chlorine, bromine, iodine and cyano, or $R^1$ and $R^2$ together with the carbon atom to which they are bonded form a saturated or partly or fully unsaturated three-, four- or five-membered ring formed from q carbon atoms and p oxygen atoms;

$R^3$ is fluorine, chlorine, cyano, $(C_1-C_3)$-alkylcarbonyloxy or $S(O)_nR^5$, or $(C_1-C_6)$-alkyl, $(C_3-C_6)$-cycloalkyl, $(C_2-C_6)$-alkenyl or $(C_2-C_6)$-alkynyl each substituted by m radicals from the group consisting of fluorine, chlorine, bromine, iodine, cyano, $(C_1-C_4)$-alkoxy and hydroxyl, or $(C_2-C_6)$-alkenylcarbonyl substituted by m radicals from the group consisting of fluorine, chlorine, bromine, iodine, cyano and $(C_1-C_6)$-alkoxy;

or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano, $(C_1-C_2)$-alkoxy and hydroxyl;

$R^4$ is hydrogen, cyano, or $(C_1-C_8)$-alkyl or $(C_3-C_8)$-cycloalkyl each substituted by m radicals from the group consisting of fluorine, chlorine, bromine, iodine, cyano, hydroxyl and $(C_1-C_6)$-alkoxy;

A is a bond or a divalent unit from the group consisting of

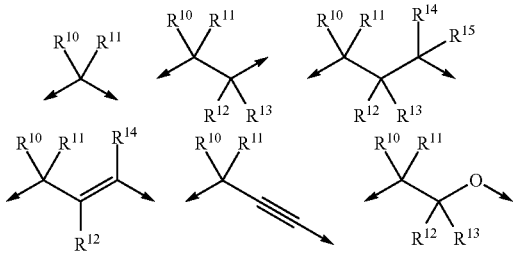

$R^{10}$, $R^{11}$, $R^{12}$, $R^{13}$, $R^{14}$ and $R^{15}$ are each independently hydrogen, fluorine, chlorine, bromine, iodine, hydroxyl, cyano, $CO_2R^8$, $CONR^6R^8$, $R^5$, or $(C_1-C_6)$-alkyl, $(C_3-C_5)$-cycloalkyl, $(C_2-C_6)$-alkenyl or $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

Y is oxygen or sulfur;

X is hydrogen, cyano, hydroxyl, $X^1$, or $(C_1-C_{12})$-alkyl, $(C_3-C_8)$-cycloalkyl, $(C_2-C_{12})$-alkenyl or $(C_2-C_{12})$-alkynyl each substituted by m radicals from the group consisting of fluorine, chlorine, bromine, iodine, cyano, hydroxyl, $OR^7$, $X^1$, $OX^1$, $NHX^1$, $S(O)_nR^5$, $SO_2NR^6R^7$, $SO_2NR^6COR^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6)=NOR^8$, or X, A and $R^4$ together with the nitrogen atom to which they are bonded form a saturated or partly or fully unsaturated five-, six- or seven-membered ring containing, as well as this nitrogen atom, k carbon atoms, n oxygen atoms, p sulfur atoms and p elements from the group consisting of $NR^7$ and $NCOR^7$ as ring atoms, where one carbon atom bears p oxo groups;

$X^1$ is a three-, four-, five- or six-membered saturated, partly unsaturated, fully unsaturated or aromatic ring which is formed from r carbon atoms, s nitrogen atoms, n sulfur atoms and n oxygen atoms, and which is substituted by s radicals from the group consisting of $R^6$, $R^{6a}$, $R^8$ and $R^9$, where the sulfur atoms and carbon atoms that form this ring each bear n oxo groups;

Het is a three-, four-, five- or six-membered saturated, partly unsaturated, fully unsaturated or aromatic ring which is formed from r carbon atoms, s nitrogen atoms, n sulfur atoms and t oxygen atoms, where the indices n, s and t should not all be zero at the same time, and where the sulfur atoms and carbon atoms that form this ring each bear n oxo groups;

R is fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $S(O)_nR^5$, $SO_2NR^6R^8$, $OSO_2NR^6R^8$, or $(C_1-C_6)$-alkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

$R^5$ is $(C_1-C_6)$-alkyl or $(C_3-C_6)$-cycloalkyl each substituted by m radicals from the group consisting of fluorine, chlorine, bromine, iodine, cyano and hydroxyl;

$R^6$ is hydrogen or $R^5$;

$R^{6a}$ is fluorine, chlorine, bromine, iodine, cyano, hydroxyl, $S(O)_nR^5$, or $(C_1-C_6)$-alkoxy, $(C_2-C_6)$-alkenyloxy or $(C_3-C_6)$-alkynyloxy each substituted by m radicals from the group consisting of fluorine, chlorine, bromine, cyano and $(C_1-C_2)$-alkoxy;

$R^7$ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;

$R^8$ is $R^7$;

$R^9$ is $(C_1-C_3)$-alkyl or $(C_1-C_3)$-alkoxy;

k is 3,4,5 or 6;

m is 0,1,2,3,4 or 5;

n is 0, 1 or 2;

P is 0 or 1;

q is 3,4 or 5;

r is 1, 2, 3, 4 or 5;

s is 0, 1, 2, 3 or 4;

t is 0, 1 or 2, excluding compounds in which A-X is the 5-fluoro-4-oxopentan-3-yl acid radical, to plants and/or to a site of unwanted vegetation.

9. The method as claimed in claim 8, wherein the compound is used for controlling one or more unwanted plants in one or more crops of one or more useful plants.

10. The method as claimed in claim 9, wherein the useful plants are one or more transgenic useful plants.

11. A fungicidal composition, comprising a fungicidally active amount of at least one compound of formula (I) and/or N-oxide as claimed in claim 1.

12. The fungicidal composition as claimed in claim 11 in a mixture with one or more formulation auxiliaries.

13. The fungicidal composition as claimed in claim 11, comprising at least one further pesticidally active substance from the group of insecticides, acaricides, herbicides, fungicides, safeners and growth regulators.

14. The 3-heteroarylisoxazoline-5-carboxamide according to claim 1, wherein the 3-heteroarylisoxazoline-5-carboxamide is 15. The 3-heteroarylisoxazoline-5-carboxamide according to claim 1, wherein at least one of $R^1$ and $R^2$ is other than hydrogen.

16. The 3-heteroarylisoxazoline-5-carboxamide according to claim 1, wherein

A is a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH=CH$, $C(CH_3)_2C\equiv C$, $CH(CF_3)CH_2$, $CH(CH_3)CH_2O$, $CH_2CH_2O$, $CH(cPr)CH_2O$, $CH(CH_2OCH_3),CH(CH_2CH_2SCH_3)$, $CH(COOH)$, $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$.

17. The 3-heteroarylisoxazoline-5-carboxamide according to claim 1, wherein

Y is oxygen.

18. The 3-heteroarylisoxazoline-5-carboxamide according to claim 1, wherein

X is $X^1$.

19. The method of claim 8, wherein $R^1$ and $R^2$ are each independently selected from the group consisting of hydrogen, fluorine, chlorine, bromine, iodine, cyano, or $(C_1-C_4)$-alkyl substituted by m radicals from the group consisting of fluorine, chlorine, bromine, iodine and cyano;

$R^3$ is $(C_1-C_4)$-alkyl, $(C_3-C_4)$-cycloalkyl, $(C_2-C_3)$-alkenyl or $(C_2-C_3)$-alkynyl each substituted by m radicals from the group consisting of fluorine, chlorine, bromine, cyano, $(C_1-C_2)$-alkoxy, A is a bond or a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH=CH$, $C(CH_3)_2C\equiv C$, $CH(CF_3)CH_2$, $CH(CH_3)CH_2O$, $CH_2CH_2O$, $CH(cPr)CH_2O$, $CH(CH_2OCH_3),CH(CH_2CH_2SCH_3)$, $CH(COOH)$, $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

$R^4$ is hydrogen or $(C_1-C_8)$-alkyl;

Y is oxygen or sulfur;

X is cyano, hydroxyl, $X^1$, or $(C_1-C_{12})$-alkyl, $(C_3-C_8)$-cycloalkyl, $(C_2-C_{12})$-alkenyl or $(C_2-C_{12})$-alkynyl each substituted by m radicals from the group consisting of fluorine, chlorine, cyano, hydroxyl, $OR^7$, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring which is substituted by s radicals from the group consisting of $R^6$, $R^{6a}$, $R^8$ and $R^9$ and is from the group consisting of

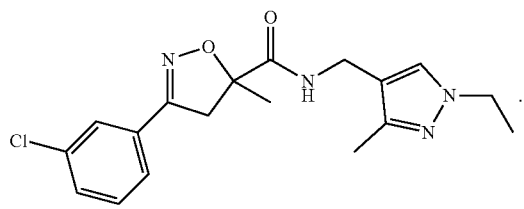 [SMILES: CCn1cc(CNC(=O)C2(C)CC(c3cccc(Cl)c3)=NO2)c(C)n1]

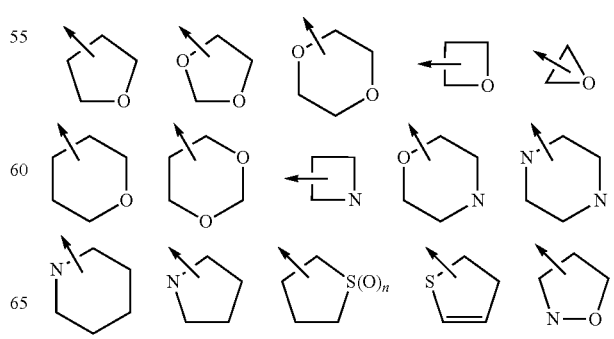

-continued

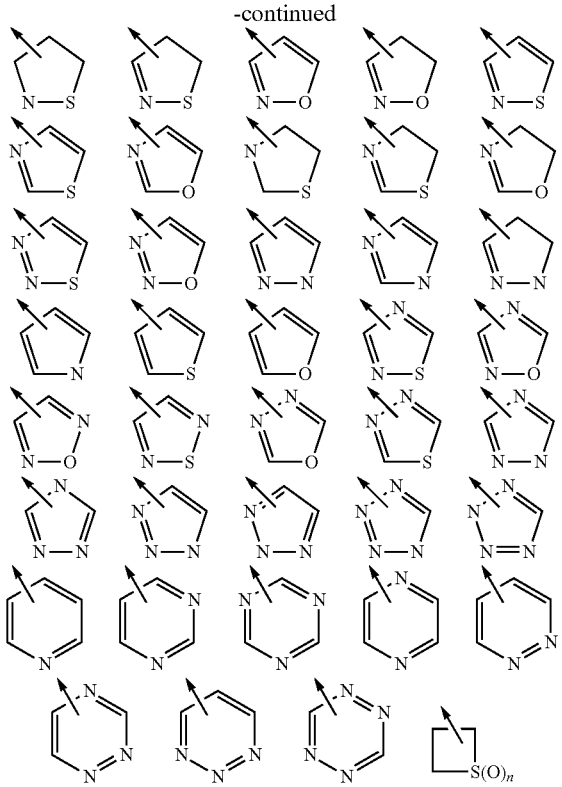

or X¹ is phenyl substituted by m radicals from the group consisting of R⁶, R⁶ᵃ, R⁸ and R⁹;

Het is pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,2,4-triazin-3-yl, 1,2,4-triazin-5-yl, 1,2,4-triazin-6-yl, 1,3,5-triazin-2-yl, pyrrol-3-yl, furan-2-yl, furan-3-yl, thiophen-2-yl, thiophen-3-yl, pyrazol-3-yl, pyrazol-4-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-4-yl, 2H-1,2,3-triazol-4-yl, 1H-1,2,4-triazol-3-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl or 2H-tetrazol-5-yl;

R is fluorine, chlorine, bromine, cyano, or $(C_1-C_6)$-alkyl each substituted by m radicals from the group consisting of fluorine and chlorine, or $(C_1-C_6)$-alkoxy substituted by m radicals from the group consisting of fluorine and chlorine;

$R^5$ is methyl or ethyl;

$R^6$ is hydrogen or $R^5$;

$R^{6a}$ is fluorine, chlorine, bromine, iodine, cyano, hydroxyl, $S(O)_n R^5$, or $(C_1-C_6)$-alkoxy, $(C_2-C_6)$-alkenyloxy or $(C_2-C_6)$-alkynyloxy each substituted by m radicals from the group consisting of fluorine, chlorine, bromine, cyano and $(C_1-C_2)$-alkoxy;

$R^7$ is hydrogen or $(C_1-C_6)$-alkyl substituted by m radicals from the group consisting of fluorine and chlorine;

$R^8$ is $R^7$, $R^9$ is $(C_1-C_3)$-alkoxy;

m is 0, 1, 2 or 3;

n is 0, 1 or 2;

s is 0, 1, 2, 3 or 4;

t is 0, 1 or 2.

* * * * *